United States Patent
Klughammer et al.

(10) Patent No.: US 9,873,913 B2
(45) Date of Patent: Jan. 23, 2018

(54) MUTATION TESTING

(71) Applicant: Roche Molecular Systems, Inc., Pleasanton, CA (US)

(72) Inventors: Barbara Klughammer, Rheinfelden (DE); Peter Meldgaard, Åbyhøj (DK); Boe Sorensen, Beder (DK); Julie Tsai, Newark, CA (US); Wei Wen, Santa Clara, CA (US); Lin Wu, Moraga, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 14/200,522

(22) Filed: Mar. 7, 2014

(65) Prior Publication Data
US 2014/0272953 A1 Sep. 18, 2014

Related U.S. Application Data

(60) Provisional application No. 61/774,946, filed on Mar. 8, 2013, provisional application No. 61/886,619, filed on Oct. 3, 2013.

(51) Int. Cl.
*C12Q 1/68* (2006.01)

(52) U.S. Cl.
CPC ......... *C12Q 1/6881* (2013.01); *C12Q 1/6886* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,210,015 | A | 5/1993 | Watson et al. |
| 5,804,375 | A | 9/1998 | Watson et al. |
| 5,972,602 | A | 10/1999 | Hyland et al. |
| 6,033,854 | A | 3/2000 | Chiang et al. |
| 6,127,155 | A | 10/2000 | Gelfand et al. |
| 6,180,349 | B1 | 1/2001 | Jensen et al. |
| 6,521,409 | B1 | 2/2003 | Benko et al. |
| 7,442,507 | B2 | 10/2008 | Chapman et al. |
| 7,960,118 | B2 | 6/2011 | Seshagiri |
| 7,964,349 | B2 | 6/2011 | Paez et al. |
| 8,067,175 | B2 | 11/2011 | Pao et al. |
| 2007/0020648 | A1 | 1/2007 | Liu et al. |
| 2008/0268449 | A1* | 10/2008 | Hoon ............... C12Q 1/6886 435/6.11 |
| 2008/0286785 | A1* | 11/2008 | Nishio ............. C12Q 1/6886 435/6.12 |
| 2010/0041048 | A1 | 2/2010 | Diaz et al. |
| 2014/0287417 | A1 | 9/2014 | Meldgaard et al. |

FOREIGN PATENT DOCUMENTS

| | | | |
|---|---|---|---|
| WO | 2002/088388 A1 | | 11/2002 |
| WO | WO 2007039705 | * | 4/2007 |
| WO | 2012/085229 A1 | | 6/2012 |
| WO | 2014/135669 A1 | | 9/2014 |

OTHER PUBLICATIONS

Didelot et al Experimental and Molecular Pathology. 2012. 92: 275-280.*
Koksal et al Genetic Testing. 2007. 11: 463-466.*
Pinzani et al (Clinica Chimica Acta. 2010. 411: 1419-1324.*
International Search Report and Written Opinion from International Application No. PCT/EP2014/054409, dated Jun. 27, 2014.
Written Opinion from International Application No. PCT/EP2014/054409, dated Feb. 11, 2015.
Bai et al., "Epidermal Growth Factor Receptor Mutations in Plasma DNA Samples Predict Tumor Response in Chinese Patients With Stages IIIB to IV Non-Small-Cell Lung Cancer," *J. Clin. Oncol.*, 2009, 27(16):2653-2659.
Brevet et al., "Detection of EGFR mutations in plasma DNA from lung cancer patients by mass spectrometry genotyping is predictive of tumor EGFR status and response to EGFR inhibitors," *Lung Cancer*, 2010, 73(1):96-102.
DeGraves et al., "High-sensitivity quantitative PCR platform," *Biotechniques*, 2003, 34(1): 106-115.
Deiman et al., "Characteristics and applications of nucleic acid sequence-based amplification (NASBA)," Mol. Biotechnol., 2002, 20(2):163-179.
Gibson et al., "A novel method for real time quantitative RT-PCR," *Genome Res.*, 1996, 6(10):995-1001.
He et al., "Detection of epidermal growth factor receptor mutations in plasma by mutant-enriched PCR assay for prediction of the response to gefitinib in patients with non-small-cell lung cancer," 2009, *Int. J. Cancer*, 125:2393-2399.
Heid et al., "Real Time Quantitative PCR," *Genome Res.*, 1996, 6(10):986-994.
Holland et al., "Detection of specific polymerase chain reaction product by utilizing the 5'->3' exonuclease activity of Thermus aquaticus DNA polymerase," *Proc. Natl. Acad. Sci. USA*, 1991, 88(16):7276-7280.
Karachaliou et al., "Association of EGFR L858R Mutation in Circulating Free DNA With Survival in the EURTAC Trial," 2015, *JAMA Oncol.*, pp. E1-E9. Published online Feb. 26, 2015 at doi:10.1001/jamaoncol.2014.257.
Kopreski et al., "Somatic Mutation Screening: Identification of Individuals Harboring K-ras Mutations With the Use of Plasma DNA," 2000 *J. Natl. Cancer Inst.*, 92:918-923.
Kuang et al., "Noninvasive Detection of EGFR T790M in Gefitinib or Erlotinib Resistant Non-Small Cell Lung Cancer," *Clin. Cancer Res.*, 2009, 15(8):2630-2636.
Lynch et al., "Activating Mutations in the Epidermal Growth Factor Receptor Underlying Responsiveness of Non-Small-Cell Lung Cancer to Gefitinib " *N. Engl. J. Med.*, 2004, 350:2129-2139.
Nygaard et al., "The correlation between cell-free DNA and tumour burden was estimated by PET/CT in patients with advanced NSCLC," 2014, *Br. J. Cancer*, 110:363-368.

(Continued)

*Primary Examiner* — Carla Myers
(74) *Attorney, Agent, or Firm* — Carol Johns

(57) ABSTRACT

Improved methods of assessing status of a solid tumor cancer in a subject involving detection of tumor-associated mutations in the subject's blood.

16 Claims, 27 Drawing Sheets

(56) References Cited

OTHER PUBLICATIONS

Paez et al., "EGFR Mutations in Lung Cancer: Correlation with Clinical Response to Gefitinib Therapy," *Science*, 2004, 304:1497-1500.

Pao et al., "Epidermal Growth Factor Receptor Mutations, Small-Molecule Kinase Inhibitors, and Non-Small-Cell Lung Cancer: Current Knowledge and Future Directions," 2005, *J. Clin. Oncol.*, 23:2556-2568.

Qin et al., "Comparison of three methods for detecting epidermal growth factor receptor mutations in plasma DNA samples of Chinese patients with advanced non-small cell lung cancer," *Chinese Medical Journal*, 2011, 124(6):887-891.

Rosell et al., "Epidermal Growth Factor ReceptorActivation: How Exon 19 and 21 Mutations Changed Our Understanding of the Pathway," *Clin. Cancer Res.*, 2006, 12(24):7222-7231.

Ryan et al., "A prospective study of circulating mutant KRAS2 in the serum of patients with colorectal neoplasia: strong prognostic indicator in postoperative follow up," 2003, *J. Clin. Pathol. Mol Pathol.*, 56: 172-179.

Sharma et al., "Epidermal growth factor receptor mutations in lung cancer," *Nat. Rev. Cancer*, 2007, 7(3): 169-181.

U.S. Appl. No. 14/200,744, Non-Final Office Action, dated Nov. 19, 2015, 13 pages.

U.S. Appl. No. 14/200,744, Restriction Requirement, dated Aug. 28, 2015, 5 pages.

U.S. Appl. No. 14/200,744, Response to Restriction Requirement, dated Oct. 28, 2015, 11 pages.

Qaigen. qPCR Somatic Mutation PCR Handbook, Aug. 2012.

\* cited by examiner

Case A

Case B

A.

B.

A.

B.

A.

B.

A.

B.

A.

B.

A.

B.

SEQUENCE LISTING

<160> NUMBER OF SEQ ID NOS: 1

<210> SEQ ID NO 1
<211> LENGTH: 11
<212> TYPE: DNA
<213> ORGANISM: Artificial Sequence
<220> FEATURE:
<223> OTHER INFORMATION: synthetic epidermal growth factor receptor
      (EGFR, Her-1, Erb-B1) mutation 2309_2310

<400> SEQUENCE: 1
ccagcgtgga t                                                          11

MUTATION TESTING

PRIOR RELATED APPLICATIONS

The present application claims the benefit of U.S. Provisional Patent Application Ser. No. 61/774,946, filed Mar. 8, 2013, and of U.S. Provisional Patent Application Ser. No. 61/886,619, filed Oct. 3, 2013, each of which is hereby incorporated by reference in its entirety.

BACKGROUND OF THE INVENTION

Germline and somatic mutations affecting various cell proliferation pathways can affect the development of cancer in patients. For example, the acquisition of somatic mutations that confer growth advantage on the cells possessing such mutations is considered an important factor in the emergence and progression of cancerous tumors. As a number of such mutations were identified, the therapies were developed that target the proteins encoded by the mutated genes, as well as the therapies targeting the signaling pathways in which these mutated genes are involved. As these targeted therapies were implemented into clinical practice, it was discovered that mutations conferring the resistance to the targeted therapies develop and accumulate in the patients' cancerous tumors, over time rendering the therapy ineffective and making it necessary to change the course of treatment.

One example of a solid tumor cancer in which somatic tumor mutations are known to play an important role is lung cancer, which is a leading cause of cancer-related mortality in many countries, including the United States. Approximately 75% of lung cancer cases belong to non-small cell lung cancer (NSCLC), which has an overall 5-year survival rate of approximately 12%. Standard surgical treatment, as well as chemotherapy and radiotherapies are available in the field of NSCLC. However, the majority of the NSCLC cases are initially diagnosed at the inoperable late stage, and relapse is common following surgery, chemotherapy, radiotherapy and other treatments. Accordingly, treatment and diagnosis of NSCLC is a challenging medical problem. One attempt at addressing the problem was the development of the targeted drug therapies that interfere with the signaling of epidermal growth factor receptor (EGFR). EGFR, which is a member of the growth factor receptor family of tyrosine kinases, is involved in signaling pathways related to cell division and is implicated in NSCLC development and progression.

Small molecule drugs erlotinib and gefitinib, which inhibit tyrosine kinase activity of EGFR, were evaluated and approved for treatment of late stage NSCLC. It was discovered, however, that these drugs were not effective in the majority of NSCLC patients, but are most effective in a subset of patients whose tumors contain somatic EGFR mutations that lead to an increase in the tyrosine kinase activity of EGFR. This type of mutations is often termed "activating." Somatic EGFR mutations that lead to resistance to tyrosine kinase inhibitor therapy in NSCLC patients were also discovered. This type of mutations is often termed "resistance." Resistance mutations in EGFR tend to arise in NSCLC patients during the course of tyrosine kinase inhibitor treatment. In the cases of NSCLC that cannot be effectively treated by tyrosine kinase inhibitor therapy, such as erlotinib and gefitinib, chemotherapy, or, possibly, other targeted therapies may be used to prolong survival. To improve the chances of selecting an effective treatment for NSCLC patients, it is therefore important to determine whether the patients' NSCLC tumors contain somatic EGFR mutations that confer sensitivity or resistance to tyrosine kinase inhibitor therapy.

BRIEF SUMMARY OF THE INVENTION

Described herein are improved methods of assessing status of a subject with a solid tumor cancer, comprising detecting presence or absence of one or more tumor nucleic acid mutations in a blood of the subject with the solid tumor cancer; and, assessing the status of the subject with the solid tumor cancer based on the detected presence or absence of the one or more tumor nucleic acid mutations. The improved methods may involve detection of the one or more tumor nucleic acid mutations by performing a quantitative real-time polymerase chain reaction (PCR) on a blood sample or on a total genomic DNA isolated from a blood sample, where the blood sample is obtained from a subject with a solid tumor cancer. Also described herein are improved methods of detecting presence or absence of a tumor mutation in a blood sample obtained from a subject with a solid tumor cancer, comprising performing a quantitative real-time polymerase chain reaction (PCR) on the blood sample using primers specific for a mutated nucleic acid sequence to generate a PCR cycle threshold. In some embodiments of the improved methods described herein, a metastatic status of the subjects' with a solid tumor cancer is taken into account in order to improve sensitivity of the detection of the mutated tumor nucleic acid sequences in the blood samples obtained from the subjects. In some other embodiments, detection of the presence or the absence of the one or more tumor nucleic acid mutations in the blood samples obtained from the subjects with the solid tumor cancers involves determining the amount of the mutated sequences circulating in the blood and monitoring the status of the subject's cancer based on the detected amount.

Described herein are methods of assessing status of a subject with distant metastasis NSCLC, comprising: detecting presence or absence of one or more mutated EGFR nucleic acid sequence in blood from the subject with distant metastasis stage NSCLC; and assessing the status of the subject with distant metastasis stage NSCLC based on the detected presence or absence of the one or more mutated EGFR nucleic acid sequence. Also described herein are methods of assessing status of a subject with NSCLC, comprising: detecting presence or absence of one or more mutated EGFR nucleic acid sequence in a blood of the subject; and assessing the status of the subject based on the detected presence or absence of the one or more mutated EGFR sequence. Also described herein are method of identifying a candidate NSCLC patient for a targeted drug therapy, comprising: detecting presence or absence of one or more mutated EGFR sequence in blood from the patient; assessing metastatic status of the NSCLC patient as M1a or M1b; and identifying the patient as a candidate for the targeted drug therapy based on at least the detected presence of the one or more mutated EGFR sequence in the blood of the patient, and the metastatic status of NSCLC in the patient. Also disclosed herein are methods of assessing status of a subject with a solid tumor cancer, comprising: detecting presence or absence of one or more tumor-associated mutated nucleic acid sequence in blood from the subject with the solid tumor cancer; and assessing the status of the subject with distant metastasis solid tumor cancer based on the detected presence or absence of the one or more mutated tumor-associated nucleic acid sequence. Furthermore, disclosed herein are methods of detecting presence or absence of a tumor-associated mutation in a blood sample, the methods comprising: performing a quantitative real-time polymerase chain reaction (PCR) on the blood sample using primers specific for a mutated nucleic sequence to generate a PCR cycle threshold; and comparing the cycle threshold to a control value, wherein the control value takes into account the concentration of genomic DNA in the sample, and wherein if the cycle threshold is below the control value the tumor-associated mutation is present in the sample and if the cycle threshold is above the control value the tumor-associated mutation is absent from the sample. Methods of treating patients or subjects with solid tumor cancers, such as NSCLC, are also envisioned and included within the scope of the methods described herein.

Some examples of the embodiments of the present invention are methods of assessing status of a human subject with a solid tumor cancer, comprising: quantifying an amount of one or more cancer-associated somatic mutation in a nucleic acid sequence in a sample obtained from the subject with the solid tumor cancer, wherein the subject has completed a cycle of cancer therapy. In some embodiments of the above methods, the cancer therapy comprises one or more of chemotherapy and administration of tyrosine kinase inhibitor. In some examples, the tyrosine kinase inhibitor is erlotinib or gefitinib. Some other examples of the embodiments of the present invention are methods of assessing status of a human subject with a solid tumor cancer, comprising: quantifying an amount of one or more cancer-associated somatic mutation in a nucleic acid sequence in a sample obtained from the subject with the solid tumor cancer before the subject has undergone cancer therapy. These and other examples can be combined in the embodiments of the methods of the present invention. Some embodiments of the above methods further comprise evaluating an outcome of the solid tumor cancer in the subject based on the amount of the one or more cancer-associated somatic mutation in the nucleic acid sequence in the sample. The outcome can be overall survival or progression free survival. In some more embodiments of the above methods, the amount of the cancer-associated somatic mutation is above a threshold level, and the method further comprises further treatment of the subject. The further treatment can comprise surgery, chemotherapy, targeted drug therapy, or any combination thereof. For example, the further treatment can comprise administration of a chemotherapeutic drug to the subject. In any or all embodiments of the methods described herein, the sample can be a plasma sample. According to some embodiments of the methods described herein, the one or more cancer-associated somatic mutation in the nucleic acid sequence comprises an activating mutation. According to some more embodiments of the methods discussed herein, the one or more cancer associated somatic mutation in the nucleic acid sequence comprises a resistance mutation. Some embodiments of the invention described herein are the methods in which the assessing comprises monitoring the solid tumor cancer in the subject. Some embodiments of the invention discussed herein are the methods in which assessing comprises administering a targeted drug therapy to the subject if the quantity of the at least one of the one or more cancer-associated somatic mutation in the nucleic acid sequence in the sample exceeds a threshold value. In some examples of such embodiments, the one or more cancer-associated somatic mutation in the nucleic acid sequence is an activating mutation, and the targeted drug therapy is a tyrosine kinase inhibitor. In some other examples of the above embodiments, the assessing further comprises increasing a dose of the targeted drug therapy administered to the subject if an increase in quantity of the one or more cancer-associated somatic mutation in the nucleic acid sequence is detected. In any or all of the embodiments of the methods described herein, the detecting can comprise performing a quantitative real-time polymerase-chain reaction. Some embodiments of methods described herein further comprise performing a diagnostic procedure on the subject. One example of the diagnostic procedure is a radiological evaluation. In the embodiments of the methods described herein, quantifying an amount of one or more cancer-associated somatic mutation in a nucleic acid sequence can be performed in the nucleic acid sequence selected from the group consisting of EGFR sequence, KRAS sequence, ALK sequence, ALK fusion sequence, ROS1, ROS1 fusion sequence, c-MET sequence, PIK3CA sequence, NRF2 sequence, FGFR1-3 sequence, AKT1 sequence, AKT1 fusion sequence, BRAF sequence, sequence comprising V600E substitution, NRAS sequence, TMPRSS2:ERG fusion sequence, SPOP sequence, RET sequence, fusion sequence, PPAR-gamma sequence, PPAR-gamma fusion sequence, IDH-1 sequence, IDH-2 sequence and FGFR3 sequence. In an exemplary embodiment of the methods described herein, the one or more cancer-associated somatic mutation is one or more somatic mutation in EGFR nucleic acid sequence. In one more exemplary embodiment of the methods described herein, the solid tumor cancer is lung cancer. In one more exemplary embodiment of the methods described herein, the solid tumor cancer is NSCLC and the nucleic acid sequence is EGFR sequence. In some examples, the one or more somatic mutation in EGFR nucleic acid sequence is selected from the group consisting of an in-frame exon 19 deletion, L858R, L861Q, G719X, T790M, S678I and in-frame exon 20 insertion.

DEFINITIONS

The term "subject" as used herein typically refers to a subject, such as but not limited to a human person, having a solid tumor cancer, such as NSCLC. It is to be understood, that a subject having a solid tumor cancer can be a patient with a known cancer, meaning the cancer that was detected prior to the performance of the embodiments of the methods of the present invention. A cancer patient can be a relapse cancer patient. For example, a subject having NSCLC can be a patient in whom NSCLC was detected prior to the performance of the embodiments of the methods of the present invention. The NSCLC patient can be a relapse patient.

The terms "recurrent," "recurrence," "relapsed," "relapse" and related terms are used to refer to cancer that returns after treatment, and to the patients that experience the return of the cancer.

The term "solid tumor cancer" is used herein to denote the cancers that are characterized by the formation of cancerous tumors, or cohesive masses of abnormally proliferating cells, in tissues and organs. It is to be understood that some tumors formed by the solid tumor cancers can be cysts, meaning fluid-filled sacks of tissue. The term "solid tumor cancer" is used herein to distinguish tumor-forming cancers from the so-called blood cancers or hematological malignancies that are formed from hematopoietic (blood-forming) cells and affect blood, bone marrow, and lymph nodes. Examples of solid tumor cancers are carcinomas, or cancers derived from epithelial cells, sarcomas, or cancers arising from connective tissue, germ cell tumors, such as seminomas and dysgerminomas, blastomas, or cancers that derive from precursor cells or embryonic tissue. Some non-limiting examples of solid tumor cancers are lung cancer, breast cancer, colorectal cancer, prostate cancer, thyroid cancer, brain cancer, such as glioblastoma, and bladder cancer. Examples of hematological malignancies are lymphomas, leukemias, myelomas, myelodysplastic syndromes and myeloproliferative diseases.

The term "therapy" is used herein synonymously with the term "treatment." The term "cancer therapy" as used herein encompasses various types of cancer therapy or treatment, including surgery, radiotherapy, chemotherapy, and targeted drug therapy. A therapy may include one or more types of therapy. For example, a therapy may include a combination of chemotherapy and targeted drug therapy. The terms "therapy" and "treatment" can be used in conjunction with the terms "cycle" or "period." A therapy or treatment can be administered one or more times over a certain period of time, followed by a period during which no treatment or therapy is administered. A therapy cycle can last for days or weeks (in one example, four weeks). One or more cycles of therapy or treatment can be administered. For example, one, two, three, four, five, six, seven, eight, nine or ten cycles of therapy or treatment can be administered. The therapy may be the same or varied during different cycles. For example, the types and/or the doses of therapy may be varied from cycle to cycle. During a therapy cycle, the therapies may be administered on a single day, several consecutive days, or continuously as an outpatient or as an inpatient. A therapy may last minutes, hours, or days, depending on the specific protocol. Therapy cycle may repeat weekly, bi-weekly, or monthly. A therapy cycle can include one or more therapy sessions. For example, a therapy cycle can be defined in monthly intervals, with two bi-weekly chemotherapy sessions classified as one cycle. One or more therapy cycles can be referred collectively as a "course" of therapy.

"Targeted therapy" or "targeted drug therapy" refer to drug therapy that interferes with the growth of cancer cells by interfering with specific molecules needed for carcinogenesis and tumor growth, rather than by simply interfering with all rapidly dividing cells, as chemotherapy does. An example of targeted drug therapy is tyrosine kinase inhibitor (TKI) therapy, which uses reversible tyrosine kinase inhibitors to inhibit the activity of tyrosine kinases promoting cell proliferation in certain types of cancers. For example, erlotinib, also known as Tarceva®, or gefitinib, also known as Iressa®, target tyrosine kinase activity of EGFR and are used as a targeted therapy for NSCLC. Another example of a targeted therapy is anaplastic lymphoma kinase (ALK) inhibitor therapy.

The term "targeted drug therapy," as used herein, is not limited to the above therapies, but can encompass any drug therapy interfering with a specific target, such as therapies that interfere with EGFR signaling. Targeted drug therapies include, but are not limited to, reversible tyrosine kinase inhibitor therapy, irreversible tyrosine kinase inhibitor therapy, antibody therapy, or any form of small molecule, large molecule or nucleic-acid based therapy, such as gene therapy or small interfering RNA therapy.

The term "tumor-associated mutation" is used herein to denote mutations in nucleic acid sequences that affect development of a solid tumor cancer in a subject. For example, a tumor-associated mutation can activate cellular proliferation, thus leading to emergence of a malignant tumor or escalation of tumor growth. A tumor-associated mutation can confer properties on a tumor that facilitate its spread throughout the subject's body, known as metastasis. A tumor-associated mutation can also be associated with susceptibility or resistance of a cancer to cancer therapies. The term "tumor-associated" can be used in reference to nucleic acids or nucleic acid sequences comprising one or more tumor-associated mutations, such as in an expression "tumor-associated mutated nucleic acid sequence." The term "cancer-associated mutation" can be used interchangeably with the term "tumor-associated mutation," for example, in reference to nucleic acids or nucleic acids sequences containing such mutations, as in an expression "cancer-associated somatic mutation in a nucleic acid sequence." It is to be understood that tumor-associated or cancer-associated mutations can be found in cell-free nucleic acids, as well as in the nucleic acids within various types of cells, including, but not limited to, tumor cells, metastatic cells, and infiltrating cells. A tumor-associated mutation or a cancer-associated mutation can be a somatic mutation.

The terms "assess," "assessment," "assessing" and the related terms are used herein in reference to cancer, status of cancer or status of a subject with cancer, and in some other contexts. These terms can denote but are not limited to inferring the presence or the absence of cancer-associated mutations in cancerous tumors based on the detected presence or absence of mutated nucleic acid sequences in the subject's blood. The terms "assess," "assessment," "assessing" and the related terms may also encompass, depending on the context, recommending or performing any additional diagnostic procedures related to evaluating the presence or absence of cancer-associated mutations in the subject's tumors, evaluating potential effectiveness of the treatments for the subject's cancer as well as recommending or performing such treatments, monitoring the subject's cancer, or any other steps or processes related to treatment or diagnosis of a cancer. For example, evaluating prognosis of a cancer in a subject, or evaluating prognosis of a cancer subject fall within the scope of the terms "assess," "assessment," "assessing" and the related terms. These terms also encompass not recommending or not recommending and performing or not performing treatment or diagnostic procedures based on the results of detection of cancer-associated mutations in the subject's tumors, as well as recommending or not recommending and performing or not performing palliative or hospice care.

The term "prognosis," "prognostication," "prognostic," "prediction," "predict." "predictive," and related terms are used herein in reference to cancer and cancer patients to denote processes and results of estimating outcomes of cancer development and cancer treatment in subjects, including the probability of metastasis, remission and relapse, as well as probabilities of survival cancer subjects. The term "prognosis," "prognostication," "prognostic," "prediction," "predict." "predictive," and related terms are included in the scope of the terms "assess," "assessment," "assessing" and the related terms. It is to be understood that various measures of cancer prognosis and outcome prediction can be used, such as probability of survival, and that a prognosis and/or predictions are often expressed as estimates or probabilities, and are not always precise.

The terms "prognostic factor" or "predictive factor" can be used interchangeably in the fields of cancer research and medicine, but can also be assigned at least partially distinct meanings Prognostic or predictive factors employed in the field of cancer diagnostics and treatment are generally the factors that affect development of cancer, cancer treatments, and survival of cancer patients. One definition of "prognostic factor" is a situation or condition, or a characteristic of a patient, which can be used to estimate the chance of recovery from cancer or the chance of disease recurrence. A prognostic factor can also be defined as a factor associated with an outcome without therapy or with application of standard therapy. In other words factor can be (but does not have to be) prognostic of a cancer outcome whether or not a therapy is applied. Some non-limiting examples of cancer prognostic factors are stage, grade, spread of the disease, as well as the age and the health of the subject. One definition of a "predictive factor" is a condition or finding that can be used to predict clinical benefit of a particular treatment, or whether a cancer in a subject will respond to a specific treatment. Predictive factor may also describe something that increases a person's risk of developing cancer, or cancer recurrence. A predictive factor can be defined as a factor associated with response or lack of response to a particular therapy and implies differential response to the particular therapy, depending on the status of biomarker. In a clinical trial setting, prognostic factors can be evaluated by comparing outcomes in the control group, while predictive factors can be evaluated by predicting outcomes in the treatment group. It is to be understood that the outcomes can be evaluated using different criteria, and prognostic and/or predictive character of a factor being evaluated may vary depending on the outcome criteria used in the evaluation. Discussion of prognostic and predictive factors is provided, for example, in Clark, "Prognostic factors versus predictive factors: Examples from a clinical trial of erlotinib" *Molecular Oncology* 1:406-412 (2008).

The term "outcome" or "outcomes" and the related terms and expressions are used herein in the context of cancer diagnostics and treatment generally to denote any specific result or effect that can be measured and relates to cancer. Examples of outcomes include, but are not limited to, decreased pain, reduced tumor size, and improvement of disease. One more example of outcome is "survival." Survival, most generally, is the length of time a patient lives or lives in a certain state (for example, in remission) after cancer diagnosis or treatment. In the context of patient groups, such as those observed during clinical trials "survival rate" of cancer patients can be used as a measure of survival. Survival rate can be expressed as the percentage of people in a study or treatment group who are still alive for a certain period of time after they were diagnosed with or started treatment for a disease, such as cancer. The foregoing "survival rate" can also be termed "overall survival rate" (OSR). The survival rate is often stated as a five-year survival rate, which is the percentage of people in a study or treatment group who are alive five years after their diagnosis or the start of treatment. Survival can also be calculated as an average period of time during which 50% of patients survive. Various types of survival measures other than OS can be used, the examples being progression-free survival (PFS) or disease-free survival (DFS). DFS is can be defined as the length of time after a treatment for a cancer ends that the patient survives without any signs or symptoms of that cancer. DFS can also be called relapse-free survival and RFS. PFS is can be defied as the length of time during and after the treatment of cancer, that a patient lives with the disease but it does not get worse, or does not progress. DFS, PFS and OS as well as other survival measures can be expressed as "rates," as discussed above, when applied to groups, and also can be expressed as probabilities. The criteria under which "progression" of solid tumor cancer in a patient are typically determined are Response Evaluation Criteria In Solid Tumors (RECIST), which is a set of published rules that define when cancer patients improve ("respond"), stay the same ("stabilize"), or worsen ("progress") during treatments. RECIST criteria are discussed, for example, in Therasse 1' et al., "New Guidelines to Evaluate the Response to Treatment in Solid Tumors" Journal of the National Cancer Institute, 92:206-216 (2000). It is to be understood, however, that modified RECIST criteria or other criteria can be employed in some embodiments described herein.

The expressions "detect in blood," "detection in blood," "detecting in blood," and the related expressions, as used herein, refer to the act or the result of finding or discovering nucleic acid sequences in a sample of the liquid fraction of blood, such as plasma or serum.

The term "local metastasis" to a process or a result of a process, in which cancer cells originating from a cancerous tumor penetrate and infiltrate surrounding normal tissues in the local area, typically in the same or adjacent organ or organs, forming new tumor. For example, "local metastasis" metastatic stage of NSCLC means that metastasis is present, but no metastasis is detected in extrathoracic organs. In reference to NSCLC, the term "local metastasis" encompasses the metastatic stage "M1a."

The term "distant metastasis" refers to a process or a result of a process, in which cancer spreads to tissues and organs that are distant from the primary tumor site. For example, the term "distant metastasis" used in the context of NSCLC means that metastasis is present and is detected in extrathoracic organs. In reference to NSCLC, the term "distant metastasis" encompasses the metastatic stage "M1b."

The terms "detect," "detecting," "detection," "and similar terms are used in this document to broadly to refer to a process or discovering or determining the presence or an absence, as well as a degree, quantity, or level, or probability of occurrence of something. The terms necessarily involve a physical transformation of matter such as nucleic acid amplification. For example, the term "detecting" when used in reference to EGFR mutation, can denote discovery or determination of the presence, absence, level or quantity, as well as a probability or likelihood of the presence or absence of the EGFR mutation. It is to be understood that the expressions "detecting presence or absence," "detection of presence or absence" and related expression, when used in reference to tumor-associated mutations, include qualitative and quantitative detection. Quantitative detection includes the determination of level, quantity or amounts of mutated nucleic acid sequences in the sample, on which the detection process is performed.

The term "mutation" or "mutated sequence," when used in reference to nucleotide or amino acid sequence can be used interchangeably with the terms "variant," "allelic variant," "variance," or "polymorphism." For example, the phrases "detecting a mutation," "detecting a mutated sequence" "detecting polymorphism" or "detecting sequence variance" can be used interchangeably when discussing the methods of the present invention.

DETAILED DESCRIPTION OF THE INVENTION

Figure 1:
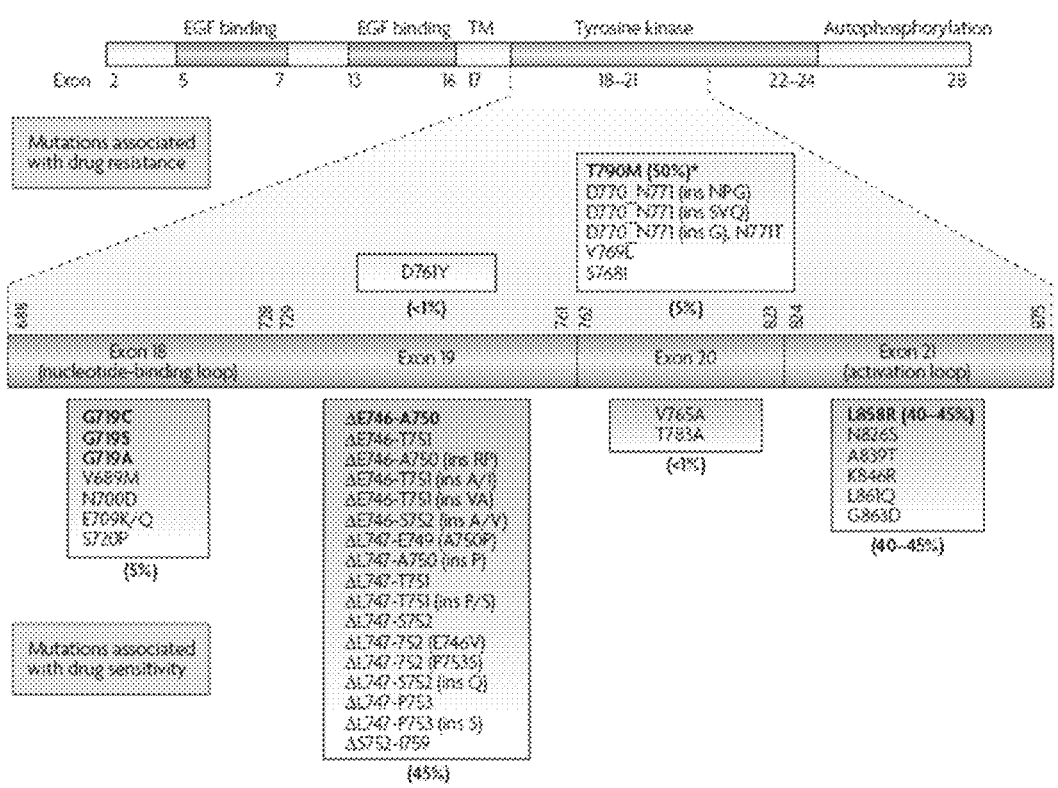
FIG. 1 is a schematic illustration of some known EGFR mutations found in the tyrosine kinase domain of EGFR, adapted from Sharma et al., *Nat. Rev. Cancer*, 7:169 (2007).

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Somatic mutations in tumor cells can affect cancer development and outcomes. One way of detecting such somatic mutations is testing tumor samples obtained through biopsy or surgery for the presence of mutant sequences associated with cancer development. However, tumor tissue samples may not be immediately available for testing. To avoid delay in detection of the cancer-associated mutations and selection of appropriate treatment as well as to reduce invasiveness, it is beneficial to develop more expedient and less invasive methods for detecting mutations in the tumors of the cancer patients. Tumor cells circulate in the blood of patients with solid tumor cancers. It is possible to detect somatic tumor mutations in the blood samples of cancer patients, including detection of EGFR mutations in NSCLC patients. However, it is difficult to reliably adapt such detection for meaningful clinical and diagnostic use due to the small amount of circulating mutated sequences, background of non-mutated sequences and high levels of genomic DNA (gDNA) circulating in the blood, the gDNA originating from broken white blood cells (WBC). Detection of mutated nucleic acid sequences originating from tumor cells in blood samples, such as detection of EGFR mutations in NSCLC patients, suffers from inaccuracies, such as relatively high false negative detection rates, and may require cumbersome analytical techniques that may involve, for example, isolation of blood-circulating tumor cells prior to detection, or enrichment of the content of mutated DNA sequences in the sample prior to detection. Quantitative detection can be even more difficult, due to high background DNA levels, among other things. Described herein are improved methods of detection of mutated tumor nucleic acid sequences in the blood of cancer patients, such as detection of mutated EGFR nucleic acid sequences in the blood of NSCLC patients, to make such detection methods useful for assessment of cancer in clinical and diagnostic practice.

The inventors discovered that detection of tumor-associated mutated nucleic acid sequences circulating in the blood of a subject with a solid tumor cancer can be performed quickly and accurately by performing real-time quantitative PCR on the blood sample or on the genomic DNA isolated from a blood sample obtained from the subject with the solid tumor cancer. By improving the methods of processing and analyzing quantitative PCR data, the inventors achieved unexpectedly improved validity of the measurements of tumor-associated mutated nucleic acid sequences circulating in the blood of the subjects with solid tumor cancers. The inventors discovered that a status of a solid tumor cancer in a subject can be advantageously assessed by measuring the type and amount of tumor-associated mutated nucleic acid sequences circulating in the subject's blood. The inventors also discovered that detection of tumor-associated mutations in subjects with solid tumor cancers based on the detection of mutated nucleic acid sequences circulating in the subjects' blood can be significantly improved if the metastasis status of the cancer in such subjects is taken into account.

Furthermore, the inventors discovered that results of detection of tumor-associated mutations in subjects with solid tumor cancers, for example, the results of detection of tumor-associated mutated nucleic acid sequences in the subjects' blood, can be employed as a prognostic and/or predictive factor for assessment of solid tumor cancer in the subjects, including assessment of therapy response and cancer outcomes. In one example, the inventors discovered that detecting the presence or emergence of somatic mutations leading to targeted drug therapy resistance in cancer patients is useful for monitoring the effectiveness of anti-cancer therapy and assessing disease progression. In another example, the inventors discovered that detecting tumor-associated mutated nucleic acid sequences in the subjects' blood one or more times during and/or after anti-cancer therapy, for example, after the subject has completed a cycle of chemotherapy, can be used to assess status of the solid tumor cancer in the subjects and to choose appropriate cancer treatment based on the detection results.

The inventors applied their discoveries in the exemplary context of detection of EGFR mutated sequences circulating in the blood NSCLC patients and clinical application of the relevant experimental data to NSCLC diagnostics and treatment. In order to apply the information on blood-detected mutated EGFR sequences to treatment and diagnostics of NSCLC patients, the inventors discerned the correlations between various aspects of the experimental data on the occurrence of mutated EGFR nucleic acid sequences in the patient's blood, such as detected presence, absence types or amounts of mutated EGFR nucleic acid sequences in the patient's blood samples, and prognostic criteria and clinical outcome measures used in the field of NSCLC treatment and diagnostics. The experimental information on mutated EGFR nucleic acid sequences was then applied as a prognostic or predictive factor for disease developments and treatment outcomes, as well as for guiding treatment, diagnostic and behavior choices of NSCLC patients. The inventors' discoveries are also generally applied to solid tumor-associated mutations that affect development of various solid tumor cancers in the subjects. Accurate and sensitive detection of tumor-associated mutated sequences circulating in the blood of the subjects with solid tumor cancers and application of thus generated experimental data to medical and diagnostic practice improve medical care of solid tumor cancer patients by improving cancer assessment, in some cases reducing the invasiveness of the diagnostic procedures, helping to select the most effective treatments for each patient, and also by reducing the amounts of unnecessary treatment and diagnostic procedures.

Detection of Tumor-Associated Mutations in Blood that Takes into Account Metastatic Status of a Subject In one example, the inventors have discovered that detection of EGFR mutations in NSCLC subjects based on the detection of mutated EGFR sequences circulating in the subjects' blood can be significantly improved if the metastasis status of the NSCLC subjects is taken into account. In particular, the inventors have discovered that in a subset of NSCLC subjects, those subjects having distant metastasis NSCLC, the presence or absence of EGFR mutations detected by amplification of nucleic acid present in blood accurately predicts the presence or absence of EGFR mutations in the subjects' NSCLC tumors. In view of the discovery that blood assays are reliable for subjects with distant metastases, a negative result, i.e., a finding of no EGFR mutations in a blood sample, is sufficient to determine that the subject does not carry the EGFR mutation and therefore does not require an invasive biopsy to confirm the negative results. In contrast, in NSCLC subjects without distant metastasis NSCLC, while the presence of detectable EGFR mutations in blood serves as an accurate predictor of the presence of EGFR mutations in the subjects' NSCLC tumors, the absence of detectable EGFR mutations in blood cannot serve as an accurate predictor of the absence of EGFR mutations in the subjects' NSCLC tumors.

The above discovery can be generally applied to the detection of tumor-associated mutations in the blood of the subjects with solid tumor cancers. Detection of an absence of a tumor-associated mutation in a blood sample obtained from a subject with distant metastasis solid tumor cancer is sufficient to determine the subject does not carry the mutation and therefore does not require any additional procedures, such as an invasive biopsy, to confirm the negative results. In contrast, if a subject has a solid tumor cancer without distant metastasis, detection of a presence of a tumor-associated mutation in blood serves as an accurate predictor of the presence of the mutations in the subjects' tumors, while detection of the absence of a detectable mutation in blood cannot serve as an accurate predictor of the absence of the mutation in the subjects' tumors. Accordingly, described herein are methods that detect the presence or absence of tumor-associated mutations in the blood of a subject with a solid tumor cancer, in order to assess the subject's status. Some embodiments of the above methods are the methods that detect the presence or absence of mutations in epidermal growth factor receptor (EGFR) in the blood of a subject with non-small cell lung cancer (NSCLC), in order to assess the subject's status.

Tumor-associated mutations can affect the effectiveness of cancer treatments. For example, tumor EGFR mutations influence the effectiveness of certain NSCLC treatments, such as therapies targeting EGFR, for example, tyrosine kinase inhibitor therapies, including, but not limited to, erlotinib and gefitinib. By using the methods described herein, the mutation status of the cancerous tumors in the subject can be accurately assessed and applied to the decision-making process on selection and administration of appropriate therapy, if any exists, or additional diagnostic procedures.

Before the discoveries described herein, high false negative error rate limited application of blood-based detection of tumor-associated mutations in a clinical and diagnostic context, since it necessitated additional testing of tumor tissue of the patients found mutation-negative based on the blood samples. Some embodiments of the methods described herein address the above problem by discriminating solid-tumor cancer subjects based on their metastasis status. In particular, the methods described herein incorporate and apply the discovery that the high false negative rate observed in the previously described blood-based diagnostic procedures is not observed among the subjects with metastatic NSCLC distant metastasis (e.g., M1b metastasis status). Blood detection of EGFR mutations in M1b metastasis status NSCLC subjects can therefore be used as a reliable diagnostic procedure for NSCLC monitoring and in determining further direction of diagnosis and treatment of NSCLC.

The embodiments of methods described herein are not limited to diagnosis and treatment of NSCLC subjects, but are generally applicable to diagnosis and treatment of the subjects with various solid tumor cancers. Furthermore, embodiments of the methods described herein are not limited to the subjects with distant metastasis solid tumor cancer. According to some embodiments of the methods described herein, the status of the solid tumor cancer in the subject without distant metastasis can also be assessed. The assessment involves inferring whether or not the subjects' tumor tissue contains mutations detected in the blood using the following criteria. The presence of the mutated sequence in the blood of the subject with a solid tumor cancer but without distant metastasis indicates a high likelihood that the subject's tumor tissue contains the mutations detected in the blood. Therefore, if mutant sequences are detected in a blood of a subject without distant metastasis (such as in a subject with no metastasis or only local metastasis), further diagnostic and treatment decisions can be made based on the high likelihood of the presence of the mutations in the subject's tumor. However, the absence of the sequence in the blood of the subject with solid tumor cancer but without distant metastasis does not reliably indicate that the subject's tumor tissue does not contain the mutations detected in the blood. If mutant sequences are not detected in a blood of such a subject, then additional diagnostic procedures are warranted to ascertain the presence of mutations in the subject's tumors.

For example, when the above embodiments of the methods of assessing a status of a subject with a solid tumor cancer are applied to NSCLC subjects, the following decision-making process can be performed. The presence of the mutated EGFR sequence in the blood of the subject with NSCLC but without distant metastasis indicates a high likelihood that the subject's NSCLC tumor tissue contains the EGFR mutations detected in the blood. Therefore, if EGFR mutant sequences are detected in a blood of a subject without metastatic NSCLC of stage M1b, further diagnostic and treatment decisions can be made based on the high likelihood of the presence of the EGFR mutations in the subject's tumor. However, the absence of the sequence in the blood of the NSCLC subject without distant metastasis does not reliably indicate that the subject's NSCLC tumor tissue does not contain the EGFR mutations detected in the blood. If EGFR mutant sequences are not detected in a blood of such a subject, then additional diagnostic procedures are warranted to ascertain the presence of mutations in the subject's NSCLC tumors.

Methods of Monitoring a Solid Tumor Cancer in a Subject by Detecting Tumor-Associated Mutated Sequences in the Subject's Blood The methods of assessing status of a subject with a solid tumor cancer described herein include diagnostic methods that use detection of tumor-associated mutations in a blood of a subject to monitor status and progression of the solid tumor cancer in the subject. Included within the embodiments of the above methods are the diagnostic methods that use detection of EGFR mutations in a blood of a NSCLC subject to monitor NSCLC status and progression in the subject.

The determination according to the above methods can be an in vitro determination performed on a blood or plasma sample extracted from the subject. The determination can be useful for monitoring cancer therapy effects and making decisions on cancer therapy selection. For example, the methods described herein can be used before, during and/or after tumor-removal surgery on a subject, to monitor the surgery's effectiveness. The methods can also be used before, during, or after any cancer therapy. For example, the methods can be used prior to a cancer therapy to determine the likelihood of the effectiveness of the therapy in a particular subject, or identifying a subject as a suitable candidate for a cancer therapy. The methods can be used during or after cancer therapy to determine the therapy's effectiveness as well as to monitor the emergence of resistance to cancer therapy. The methods can also be used during cancer remission to monitor cancer recurrence and progression.

In some embodiments, the methods employ qualitative detection of tumor-associated mutations to determine the presence or absence, or the nature of tumor-associated mutations in the blood of the subjects. In some embodiments, the methods employ quantitative determination of tumor-associated mutations to determine the amount of mutated sequences present in the subject's blood. Qualitative or quantitative determination, or combination thereof, can be referred to as determination or detection of a "mutation load," and can be used to assess the status of a solid tumor cancer in the subject, including the severity of the cancer. Mutation load of tumor-associated mutation in a blood of a subject can be characterized by the number of tumor-associated mutations in the subject's blood (that is, how many different mutations are detected), amount of tumor-associated mutations detected in the subject's blood (quantity of the mutated tumor-associated nucleic acids circulating in the subject's blood), or a combination of the foregoing. It is to be understood that, in some cases, a mutation load of tumor-associated mutations detected in the blood of a subject with a tumor-associated cancer correlates with the cancer's severity and/or progression in a subject. Mutation load can also correlate with the effectiveness or lack thereof of cancer therapies administered to the subject.

In one embodiment of the methods of monitoring a solid tumor cancer described herein, the mutation load being detected is quantity of at least one activating tumor-associated mutation and at least one resistance tumor-associated mutation in a blood sample obtained from a solid cancer patient. The mutation load is being detected over time, for example, during a course of cancer therapy or therapies. Thus, changes over time in the mutation load of a cancer subject can be determined. The detected quantity or change in quantity of the at least one activating tumor-associated mutation can serve as an indicator of cancer progression, severity, and/or a success or lack thereof of the therapy or the therapies administered to the patient. The decision-making process on the treatment of the solid tumor cancer in the patient can be performed based on the mutation load being detected.

Unexpectedly, by applying the methods described herein, progression, severity or stage of a solid tumor cancer in a patient, as well as susceptibility of the cancer to certain therapies, can be reliably recognized or determined before the emergence of clinical signs or symptoms in the subject, or before the signs or symptoms become detectable by other detection techniques and procedures. In some cases, the status of a solid tumor cancer in a subject can be assessed one or more (meaning 1, 2, 3, 4, 5, 6, 7, 8, 9, 10, 11, 12, 13, or any interval delineated by these integers) weeks or months before the emergence of clinical signs or symptoms of solid tumor cancer in the subject. Clinical decisions can therefore be made based on the tumor-associated mutation load found in the subject's blood. For example, a cancer therapy can be started, stopped or changed based the subject's detected mutation load. In another example, a cancer therapy dose can be adjusted, such as increased or decreased, based on the subject's tumor-associated mutation load.

In one illustrative example, the mutation load of EGFR mutations in a blood of a subject with NSCLC is determined and used in a clinical decision-making process. In some illustrative examples, quantitative measurements of a mutation load are used to monitor quantitative dynamic changes of EGFR mutations in NSCLC patients, and these quantitative changes are used to guide the clinical decisions. Therapies, such as targeted EGFR therapy, can be indicated and administered to the subject based on the detected quantitative changes of one or more activating EGFR mutations in the subject's blood. For example, if a detected amount of one more EGFR mutations is above a threshold level, then a therapy can be indicated and administered to the subject. In another example, if a detected amount of one or more EGFR activating mutations is above a threshold level, then the dose of the targeted EGFR therapy is determined based on the activating EGFR mutation load. For example, higher dose of the targeted EGFR therapy with a reversible tyrosine kinase inhibitor ("reversible TKI therapy") can be recommended based on the higher detected mutation load of EGFR mutations. The status of the NSCLC subject is monitored during the course of the reversible TKI therapy. Decrease or, in some cases, maintenance of the activating EGFR mutation load indicates a success of the reversible TKI therapy, indicating that it can be continued or, in some cases, stopped. Increase in EGFR mutation load indicates a decrease in the effectiveness of the reversible TKI therapy. Emergence of the resistance EGFR mutations or increase of resistance EGFR mutation load also indicates a decrease or a potential decrease in the effectiveness of the reversible TKI therapy. When a decrease or potential decrease in the effectiveness of the TKI therapy is detected, various clinical decisions can be made, such as increasing the dosage of the reversible TKI therapy, administering a different therapy, such as chemotherapy and/or radiotherapy, administering a different targeted therapy, such as an irreversible TKI therapy, or any combination of the foregoing. Clinical decisions can include decision to start, stop, or choose not to perform a treatment or a diagnostic procedure, a decision to enter palliative or hospice care, or a decision to stop all treatments and procedures.

In some embodiments of the methods of assessing status of a solid-tumor cancer, the mutation load of EGFR mutations in a blood of a subject with NSCLC is detected and quantified, and the results of detection and quantification are used to survey, appraise or monitor NSCLC patients. In this context, the results of the detection and quantification are used to make clinical decisions with respect to NSCLC patients, including treatment decisions and diagnostic decisions. In some cases, the EGFR mutation load detection and quantification can be used in place of other diagnostic procedures, such as CT scans and radiologic assessment, to appraise, survey or monitor NSCLC in patients. In some other cases, the EGFR mutation load assessment can be used in conjunction with other diagnostic procedures to appraise, survey or to monitor NSCLC in patients. In comparison to other diagnostic techniques and procedures used in NSCLC monitoring, such as biopsies, radiologic assessment or other imaging techniques, such as CT scanning, the detection of EGFR mutated nucleic acid sequences in blood of NSCLC subjects can have a lower risk to the patient, lower invasiveness or lower costs, or a combination of the these advantages. Accordingly, detection of EGFR mutated nucleic acids in the blood of NSCLC subjects can be performed more frequently than at least some other diagnostic techniques and procedures, which may allow earlier detection of cancer progression and earlier administration of therapies to the subject, as compared to a situation in which detection of EGFR mutated nucleic acids in the blood of NSCLC subjects is not performed. Detection of EGFR mutated nucleic acids in the blood of NSCLC subjects can be performed at various time points ("detection time points"), examples of which are discussed in "Tumor-associated mutations as a prognostic or predictive factor of solid-tumor cancer assessment" section of this document. The exemplary situations discussed below illustrate some embodiments of the methods described herein.

Detection of EGFR mutated nucleic acids in the blood of NSCLC patients can be used to monitor NSCLC in the patients, instead of or in combination with other diagnostic techniques, such as radiology (X-rays) or imaging techniques, such as CT scanning. The results of detection of EGFR mutated nucleic acids in NSCLC patients' blood can be used to guide diagnostic decisions. For example, if an increase in EGFR mutated nucleic acids is detected in a patient during a treatment cycle or upon completion of a treatment cycle, as compared to an earlier detection time point, then a decision can be made to perform additional diagnostic procedures, to alter diagnostic procedures, or both. For example, if an increase in EGFR mutated nucleic acids is detected in a patient during a treatment cycle or upon completion of a treatment cycle, as compared to an earlier detection time point, then the decision is made to monitor the patient more closely. The above decision can be made even if the radiologic or imaging assessment is not performed or is performed, but does not confirm disease progression. One situation where the above example may arise is when disease progression in a patient is monitored after the TKI inhibitor treatment is ended to detect the so-called "flare effect," which means the tumor starts growing very fast after TKI inhibitor treatment is stopped.

Monitoring the patient more closely, or closer monitoring, in this and other examples, can mean that the patient can be subjected to additional diagnostic procedures, such as radiologic assessments (X-rays) or other imaging assessments (for example, CT scanning), which would not be performed if increase in EGFR mutated nucleic acids was not detected. Monitoring the patient more closely can also mean that the patient can be subjected to more frequent diagnostic procedures, such as detection of EGFR mutated nucleic acids, radiologic assessments (X-rays) or other imaging assessments (for example, by CT scanning), than the frequency with which one or more of these diagnostic procedures would be performed if the increase in EGFR mutated nucleic acids was not detected. Closer monitoring may allow the clinician to capture disease progression at its earliest time point.

When detection of EGFR mutated nucleic acids in the blood of NSCLC patients is used to monitor NSCLC in the patients, the results of detection of EGFR mutated nucleic acids in NSCLC patients' blood can also be used to guide treatment decisions. For example, if an increase in EGFR mutated nucleic acids is detected in a patient during a treatment cycle or upon completion of a treatment cycle, as compared to a an earlier detection time point, then a decision can be made to continue the treatment, such as to administer another cycle of the same therapy, or to modify the therapy administered in the next cycle, as compared to the prior treatment cycle. The above decisions can be made even if NSCLC progression is not detected by other diagnostic procedures. If a decrease in EGFR mutated nucleic acids is detected in a patient during a treatment cycle or upon completion of a treatment cycle, as compared to an earlier detection time point, then a decision can be made to not administer another cycle of the same therapy, or to modify the therapy administered in the next cycle, as compared to the prior treatment cycle. For example, if an increase in EGFR mutated nucleic acids is detected, and only chemotherapy is administered in the treatment cycle during or after which the increase in EGFR mutated nucleic acid was detected, then a decision can be made to administer TKI inhibitor therapy, such as erlotinib therapy, instead or in addition to chemotherapy in the next cycle. In another example, if an increase in EGFR mutated nucleic acids is detected, and TKI therapy only is administered in the treatment cycle during or after which the increase in EGFR mutated nucleic acid was detected, then a decision can be made to administer chemotherapy in addition to TKI therapy in the next cycle. In one more example, if an increase in EGFR mutated nucleic acids is detected, and a combination of TKI therapy and chemotherapy is administered in the treatment cycle during or after which the increase in EGFR mutated nucleic acid is detected, then a decision can be made to increase a dose of chemotherapy, of TKI therapy or the dose of both therapies, in the next cycle. If a decrease in EGFR mutated nucleic acids is detected, and a combination of TKI therapy and chemotherapy is administered in the treatment cycle during or after which the decrease in EGFR mutated nucleic acid is detected, then a decision can be made to decrease a dose of chemotherapy, of TKI therapy, or both in the next cycle. If a decrease in EGFR mutated nucleic acids is detected during a treatment cycle or upon completion of a treatment cycle, as compared to a prior detection point, then a decision can be made not to administer the next treatment cycle, or to administer the next treatment cycle later than in a situation in which no decrease in EGFR mutated nucleic acids is detected. In yet another example, if an increase in EGFR mutated nucleic acids is detected in a patient during a treatment cycle or upon completion of a treatment cycle, as compared to a prior detection time point, then a decision can be made to start the next treatment cycle earlier than in a situation in which no increase in EGFR mutated nucleic acids is detected. One situation where the above example may arise is when disease progression in a patient is monitored after the TKI inhibitor treatment is ended to detect the "flare effect." If in increase in mutated EGFR mutated nucleic acids is detected after TKI therapy treatment cycle ended, a decision can be made to resume TKI therapy immediately.

Detection of EGFR mutated nucleic acids in the blood of NSCLC patients can be used to appraise or survey NSCLC in the patients, instead of or in combination with other diagnostic techniques, such as radiology (X-rays) or imaging techniques, such as CT scanning. The results of detection of EGFR mutated nucleic acids in NSCLC patients' blood can be used to guide diagnostic decisions. For example, if a level of EGFR mutated nucleic acids in a patient's blood is determined to be above a threshold level at a particular detection time point, then a decision can be made to perform additional diagnostic procedures, to alter diagnostic procedures, or both. For example, if a level of EGFR mutated nucleic acids in a patient's blood is determined to be above a threshold level after a treatment cycle ended, then the decision is made to monitor the patient more closely. One situation where the above example may arise is when disease progression in a patient is monitored after the TKI inhibitor treatment is ended to detect the "flare effect."

When detection of EGFR mutated nucleic acids in the blood of NSCLC patients is used to survey or to appraise NSCLC in the patients, the results of detection of EGFR mutated nucleic acids in NSCLC patients' blood can also be used to guide treatment decisions. For example, if the level of EGFR mutated nucleic acids in NSCLC patient's blood is determined to be above a threshold level at a particular detection time point, such as during a treatment cycle or upon completion of a treatment cycle, then a decision can be made to continue the treatment, such as to administer another cycle of the same therapy, or to modify the therapy administered in the next cycle, as compared to the prior treatment cycle. The above decisions can be made even if NSCLC progression is not detected by other diagnostic procedures. If the level of EGFR mutated nucleic acids in NSCLC patient's blood is determined to be below a threshold level at a particular detection time point, such as during or upon completion of a treatment cycle, then a decision can be made to not administer another treatment cycle, or to modify the therapy or therapies administered in the next cycle, as compared to the prior treatment cycle. For example, if the level of EGFR mutated nucleic acids in NSCLC patient's blood is determined to be above a threshold level at a detection time point during or after a treatment cycle, and only chemotherapy was administered in the treatment cycle, then a decision can be made to administer TKI inhibitor therapy, such as erlotinib therapy, instead or in addition to chemotherapy in the next cycle. In another example, if the level of EGFR mutated nucleic acids in NSCLC patient's blood is determined to be above a threshold level at a detection time point during or after a treatment cycle, and TKI therapy only was administered in the treatment cycle, then a decision can be made to administer chemotherapy in addition to TKI therapy in the next cycle. In one more example, if the level of EGFR mutated nucleic acids in NSCLC patient's blood is determined to be above a threshold level at a detection time point during or after a treatment cycle, and a combination of TKI therapy and chemotherapy is administered in the treatment cycle, then a decision can be made to increase a dose of chemotherapy, of TKI therapy, or both in the next cycle. If the level of EGFR mutated nucleic acids in NSCLC patient's blood is determined to be below a threshold level at a detection time point during or after a treatment cycle, and a combination of TKI therapy and chemotherapy is administered in the treatment cycle, then a decision can be made to decrease a dose of chemotherapy, of TKI therapy, or both in the next cycle. In yet another example, if the level of EGFR mutated nucleic acids in NSCLC patient's blood is determined to be above a threshold level at a detection time point during or after a treatment cycle, then a decision can be made to start the next treatment cycle earlier than a situation in which the above-threshold level EGFR mutated nucleic acids was not detected. One situation where the above example may arise is when disease progression in a patient is monitored after the TKI inhibitor treatment is ended to detect the "flare effect." If the level of EGFR mutated nucleic acids in NSCLC patient's blood is determined to be above a threshold level at a detection time point after a TKI treatment cycle, then a decision can be made to resume TKI therapy immediately. If the level of EGFR mutated nucleic acids in NSCLC patient's blood is determined to be below a threshold level at a detection time point during or after a treatment cycle, then a decision can be made to not administer the next treatment cycle, or to administer the next treatment cycle later than a situation in which below-threshold level in EGFR mutated nucleic acids was not detected.

Tumor-Associated Mutations as a Prognostic or Predictive Factor of Solid-Tumor Cancer Assessment According to some embodiments of the methods described herein, results of detection of tumor-associated mutation or mutations in subjects with solid tumor cancers are used as prognostic and/or predictive factors for outcomes of solid tumor cancer in the subjects. The inventors discovered that the results of detection of tumor-associated mutated nucleic acid sequences correlate with the subjects' solid tumor cancer outcomes, including cancer therapy responses. The inventors applied their discovery to treatment and diagnostics of solid tumor cancer by incorporating detection of tumor-associated mutated nucleic acid sequences in plasma samples obtained from cancer subjects into methods related to diagnostics and treatment of solid tumor cancers. Some embodiments of the methods described herein incorporate detection and/or quantification of tumor-associated mutations in the patients' blood by testing patients' plasma samples for tumor-associated mutated nucleic acid sequences. The detection according to the above methods can be an in vitro detection performed on a blood or plasma sample extracted from the subject. Mutation load detected in the blood of the subjects with solid tumor cancers can be used a prognostic factor and/or a predictive factor with respect to cancer development and outcomes. According to the treatment and diagnostic methods embodying useful application of the inventors' discovery, the detection results can be used in the steps following detection to predict solid cancer development, patient outcomes, effects of cancer therapies, as well as for choosing treatment and diagnostic procedures and guiding the behavior choices of solid-tumor cancer patients.

In a particular example, the inventors' discovery can be applied to treatment and diagnostics of NSCLC by incorporating detection and/or quantification of mutated EGFR sequences in blood of NSCLC patients into the methods related to NSCLC diagnosis and treatment, thus using EGFR mutations as a prognostic or predictive factor of NSCLC cancer assessment. The detection of EGFR sequences can be performed by testing the sample for mutated EGFR sequences by a suitable analytical technique. One example of such technique is quantitative PCR, such as real-time quantitative PCR, which can be suitably employed in the various treatment and diagnostic methods described herein, and can incorporate one or more of the improved techniques described in the "Improved Detection of Tumor-Associated Mutations" section of this document.

According to the embodiments of methods of the present invention, which usefully apply the inventors' discoveries to the methods related to treatment and diagnostics of solid tumor cancers, such as NSCLC, treatment and diagnostics, presence, absence, amount, or types of mutated sequences detected in the plasma samples can serve, separately or in combination, as a prognostic and/or predictive factor with respect to solid-tumor cancer outcomes and responses to therapy, including chemotherapy and targeted drug therapy (for example, TKI therapy). The methods according to the embodiments of the present invention can employ quantitative and/or qualitative detection of tumor-associated mutations to determine the presence or absence, or the nature of tumor-associated mutations in the blood of the subjects. Qualitative or quantitative determination, or combination thereof, can be referred to as determination or detection of a "mutation load," which is a term and a concept described elsewhere in this document with explanatory examples. The principles and the examples of "mutation load" determination described elsewhere in this document can also be applicable to the methods described in this section. For example, mutation load of EGFR sequences detected in a NSCLC subject, for example, in a plasma sample obtained from NSCLC subject, can serve as a prognostic and/or predictive factor with respect to NSCLC cancer outcomes and responses to therapy, including chemotherapy and targeted drug therapy.

The mutation load can be detected at one or more time points, for example, at one or more points before, during or after a course of cancer therapy or therapies. For example, the mutation load can be detected at or close to the start of cancer diagnosis but before the start of any treatments or therapies. The mutation load can be detected during the treatment cycle, after the end of the treatment cycle, or between the treatment cycles. The mutation load can be detected at one or more points during remission or at one or more points during relapse. It is to be understood that, in some instances, mutation load detected at only one point, such as during a treatment cycle, can serve as a prognostic and/or predictive factor of solid-tumor cancer outcome. In other cases, mutation loads detected at two or more time points evaluated in combination can serve as a prognostic and/or predictive factor with respect to solid-tumor cancer outcome. The detection at two or more time points can be used to monitor cancer progress or success of particular treatments and make appropriate clinical decisions, as discussed in the section "Methods of Monitoring a Solid Tumor Cancer in a Subject by Detecting Tumor-Associated Mutated Sequences in the Subject's Blood" of this document.

The time point at which the detection is conducted may be selected based on the predictive and/or prognostic value of the results obtained at that point, or, in some circumstances, it can be chosen for convenience, for example, to coincide with another diagnostic or treatment procedure or procedures. For example, detection of mutation in tissue samples may necessarily be conducted at the time point of biopsy, since this is when the tumor tissue samples are extracted by using an invention procedure. Detection of mutation load in blood or plasma may be conducted at different time points and may be conducted frequently, as little risk for the patient exists. One example of the time point at which the samples for detection are obtained in order to perform detection steps according to the embodiments of the methods described herein ("detection time point") is the time point at which initial diagnostic procedures are conducted on a subject. This time point may coincide with the time point at which initial biopsy, radiologic assessment or other diagnostic procedures, such as CT scanning, are performed. The levels of mutated EGFR mutated nucleic acids detected at this time point can serve as "baseline" levels against which progression of a cancer (or lack of progression) are gauged. One more example of the detection time point is the time point before starting a cancer treatment. Other examples of the detection time points are the time point during a treatment cycle, a time point after the end of a treatment cycle, and a time point after the end of a treatment course.

For example, when a solid-tumor cancer patient is administered several treatment cycles, a detection time point can be during the first treatment cycle, after the end of the first treatment cycle but before the start of the second treatment cycle (if the second treatment cycle is administered), during the second treatment cycle, after the end of the second treatment cycle but before the start of the third treatment cycle (if the third cycle is to be administered), during the third treatment cycle, after the end of the third treatment cycle but before the start of the fourth treatment cycle (if the fourth treatment cycle is administered, and so forth with respect to the following treatment cycles, such as the fourth, the fifth, the sixth or the subsequent cycles. It is to be understood the detection and one or more of the above time points can be performed. It is also understood that other time points may be employed in the methods according to the embodiments of the present invention.

In some embodiments of the methods of monitoring a solid tumor cancer described herein, the mutation load being detected is presence, absence or quantity of at least one activating tumor-associated mutation in a blood sample obtained from a solid cancer patient. The detected mutation load, such as presence, absence or quantity of the at least one activating tumor-associated mutation, serves as a prognostic and/or predictive factor with respect to one or more solid-tumor cancer outcomes. Non-limiting examples of the outcomes are tumor size, tumor metastasis, success of a therapy, which can be result in a patient entering remission, patient survival (including, but not limited to, overall survival, disease-free survival and progression-free survival), which can be measured as probability of survival for a specified time period, cancer relapse, tumor "flare," or patient death. One or more decisions on further actions with respect to the solid-tumor cancer patient are performed based on the mutation load being detected. Examples of decisions on such further actions are decisions to choose an alternative targeted therapy, to start, stop, or choose not to perform a treatment or a diagnostic procedure, a decision to enter palliative or hospice care, or a decision to stop all treatments and procedures.

For example, the methods described herein use detection of the mutation load before, during and/or after tumor-removal surgery on a subject, as a prognostic and/or predictive factor of the surgery's effectiveness. The methods can also use before, during, or after any cancer therapy as prognostic and/or predictive factor of the therapy's effectiveness. For example, the methods can be used to determine the probability of survival, including OSS and PS, after performing a therapy, such as chemotherapy, TKI therapy, or their combination, in a particular subject. The methods can also be used to identify a subject as a suitable candidate for a cancer therapy, for example, by determining, based on the results of detection of a mutation load, whether or not a cancer outcome would be favorably affected by a treatment or therapy. The methods can be used to determine future course of therapy, which may involve, for example, administering additional therapy cycles or modifying therapy regimen. Outcome probabilities based on the detected mutation load can be determined more than once in a particular patient and can be used to monitor solid-tumor cancer progress and treatment effectiveness. The methods can also be used during or after cancer therapy to determine suitable choices and timelines for post-therapy care. For example, if probable length of survival is determined, a patient can be recommended to make arrangements for palliative or hospice care based on the determination.

Unexpectedly, by using quantitative detection of tumor-associated mutations according to the methods described herein, probability of an outcome of a solid tumor cancer in a patient can be determined. Clinical decisions can therefore be made based on quantifying an amount of one or more tumor-associated mutated nucleic acid sequences. The methods of described herein can, in some cases, advantageously reduce or minimize the number of complex, expensive or invasive diagnostic and treatment procedures performed on a solid tumor cancer patient, while at the same time providing diagnostic data for informed clinical decision making process. The methods described herein can lower the cost of cancer treatment and diagnostics, decrease patient discomfort and burdens, and lead to more informed clinical decision making process. In some other cases, the methods described herein can detect cancer progression earlier than other methods, thus allowing the clinicians to make earlier decisions on the treatment and diagnostics procedures to be employed in a particular cancer patient, potentially improving cancer outcome.

In an illustrative example, the mutation load of EGFR activating mutations in a subject with NSCLC is determined at before or during one of the treatment cycles, which may include chemotherapy, TKI therapy, or a combination of these therapies. The mutation load of activating EGFR mutations detected during a treatment cycle, for example, during a third cycle out of the six cycles, is used as predictive fact with respect to the success of TKI therapy, and, in some cases, as a prognostic factor with respect to patient survival whether or not TKI therapy is used. In another example, the mutation load of EGFR activating mutations in a subject with NSCLC is determined at baseline, or before the start of any treatments, which may include chemotherapy, TKI therapy, or a combination of these therapies. The mutation load of activating EGFR mutations detected at baseline is used as a predictive factor for EGFR mutation-positive patients with respect to the success of TKI treatment, measured by PFS, OS or both. Based on the available evidence, such as the results of the clinical trials, the experimental data on detected mutation load is interpreted and used as a prognostic and/or predictive factor for NSCLC outcomes in a patient. For example, the experimental data on the detected mutation load at a particular time point can be used as a prognostic factor for a probable outcome of a particular patient or to predict a response to a therapy. In one example, a mutation load of EGFR activating mutations detected during a therapy cycle, serves as a prognostic factor of OS of a particular patient, which is evaluated to be longer for the patients with detected mutation load of EGFR activating mutations, whether or not chemotherapy is used alone or in conjunction with TKI therapy for the patient's treatment. In another example, a mutation load of EGFR activating mutations detected in a patient during a therapy cycle of combination chemotherapy and TKI therapy, serves as a predictive factor for the success of TKI therapy in the NSCLC patient expressed as increased PFS and OS. After the probable outcome is evaluated in a particular patient, clinical decisions can be made according to the exemplary guidelines discussed in the section "Methods of Monitoring a Solid Tumor Cancer in a Subject by Detecting Tumor-Associated Mutated Sequences in the Subject's Blood" of this document.

Improved Detection of Tumor-Associated Mutations

In the embodiments of the methods described herein, nucleic acid sequences are detected by suitable methods, such as quantitative amplification or nucleic acid sequencing. Methods of quantitative amplification are disclosed in, e.g., U.S. Pat. Nos. 5,210,015; 5,804,375; 6,127,155; 6,180,349; 6,033,854; and 5,972,602, as well as in, e.g., Holland et al., Proc. Natl. Acad. Sci. 88:7276-7280 (1991), Gibson et al., Genome Research 6:995-1001 (1996); DeGraves, et al., Biotechniques 34(1):106-10, 112-5 (2003); Deiman B, et al., Mol Biotechnol. 20(2):163-79 (2002). Amplifications may be monitored in "real time." Though standard Sanger dideoxy or other older nucleotide sequencing methods can be used, sequencing can be particularly effective when high throughput sequencing is used, e.g., "next generation sequencing" methods such as HiSeg™, MiSeg™, or Genome Analyzer (each available from Illumina), SOLiD™ or Ion Torrent™ (each available from Life Technologies) and 454™ sequencing (from Roche Diagnostics). For example, in high-throughput sequencing, parallel sequencing reactions using multiple templates and multiple primers allows rapid sequencing of genomes or large portions of genomes. See, e.g., WO 03/004690, WO 03/054142, WO 2004/069849, WO 2004/070005, WO 2004/070007, WO 2005/003375, WO0006770, WO0027521, WO0058507, WO0123610, WO0157248, WO0157249, WO02061127, WO03016565, WO03048387, WO2004018497, WO2004018493, WO2004050915, WO2004076692, WO2005021786, WO2005047301, WO2005065814, WO2005068656, WO2005068089, WO2005078130, and Seo, et al., Proc. Natl. Acad. Sci. USA (2004) 101:5488-5493. In some embodiments, the amplicons are sequenced by one of the methods selected from a base-incorporation method, e.g., a pyrosequencing method (U.S. Pat. Nos. 6,274,320, 6,258,568 and 6,210,891); a hydrogen ion detection method (ISFET) (e.g., U.S. Pat. No. 8,262,900), or a dye-terminator detection method (U.S. Pat. Nos. 7,835,871, 8,244,479, 8,315,817 and 8,412,467.) Deep sequencing technology and instruments (i.e., technology and instrument capable of digital sequence readout) may also be employed. Without limitation, the examples of instruments include GS family of instruments (454 Life Sciences, Branford, Conn.); ION PROTON® and PGM™ (Life Technologies, Grand Island, N.Y.); HISEQ® and MISEQ® (Illumina, San Diego, Calif.) or any improvements and modifications of thereof.

In some embodiments of the methods described herein, quantitative PCR is employed. Quantitative PCR refers generally to a method that allows for quantification of the amounts of the target nucleic acid sequence used at the start at the PCR reaction. Quantitative PCR techniques use various approaches to quantification. One example of a quantitative PCR method is "real time PCR," which can be also referred to as "real time quantitative PCR." Although some sources use the terms "real time PCR" and "quantitative PCR" synonymously, this is not the case for the present document. Here, the term "quantitative PCR" encompasses all PCR-based techniques that allow for quantification of the initially present target nucleic acid sequences. The term "real time PCR" is used to denote a subset of quantitative PCR techniques that allow for detection of PCR product throughout the PCR reaction, or in real time. The principles of real-time PCR are generally described in Holland et al. (1991) and Held et al. "Real Time Quantitative PCR" Genome Research 6:986-994 (1996). Generally, real-time PCR measures a signal at each amplification cycle. Conventional real-time PCR techniques rely on fluorophores that emit a signal at the completion of every multiplication cycle. Examples of such fluorophores are fluorescence dyes that emit fluorescence at a defined wavelength upon binding to double-stranded DNA, such as SYBR green. An increase in double-stranded DNA during each amplification cycle thus leads to an increase in fluorescence intensity due to accumulation of PCR product. Another example of fluorophores used in real-time PCR is sequence-specific fluorescent reporter probes. The examples of such probes are TagMan® probes and FRET probes. TagMan® probes contain a fluorophore and a fluorescence quencher, which reduces the fluorescence emitted by the fluorophore. During the extension phase of PCR, the probe is cleaved by the exonuclease activity of the DNA polymerase, releasing the fluorophore. The fluorophore release results in an increase in fluorescence signal, which is proportionate to the amount of the PCR product. FRET probes employ fluorescence resonance energy transfer (FRET). Two labeled sequence-specific probes are designed to bind to the PCR product during the annealing phase of PCR, which results in an energy transfer from a donor fluorophore to an acceptor fluorophore. This results in an increase in fluorescence during the annealing phase, which is proportional to the amount of the PCR product.

The use of sequence-specific reporter probe provides for detection of a target sequence with high specificity, and enables quantification even in the presence of non-specific DNA amplification. Fluorescent probes can also be used in multiplex assays—for detection of several genes in the same reaction—based on specific probes with different-colored labels. For example, a multiplex assay can use several sequence-specific probes, labeled with a variety of fluorophores, including, but not limited to, FAM, JA270, CY5.5, and HEX, in the same PCR reaction mixture.

One example of a multiplex assay that can be suitably employed for detection of mutated EGFR sequences according to the methods of the present invention is allele-specific PCR, such the assay that can be performed with the COBAS® EGFR Mutation Test kit (Roche Molecular Diagnostics, Indianapolis, Ind.), which employs allele-specific EGFR primers to detect mutations in nucleic acid sequences in the presence of wild-type variants of the sequences. Allele-specific PCR is a technique in which the variant of the nucleic acid sequence present in the PCR reaction mixture is selectively amplified and detected. Allele-specific PCR employs at least one "allele-specific primer." The term "allele-specific" primer generally refers to a primer whose extension occurs in a PCR reaction only when a specific variant of a nucleic acid sequence is present in the reaction mixture. In other words, allele-specific primers are designed in such a way that they discriminate between variants of nucleic acids and selectively multiply nucleic acid templates that include a variant to be detected.

Some embodiments of the methods described herein employ improved detection methods of tumor-associated mutations in blood samples obtained from a subject with a solid tumor cancer. In one example, the step of detecting one or more EGFR mutations in a blood of a subject with NSCLC comprises detection of one or more mutated NSCLC nucleic acid sequences in a sample obtained from the subject. The detection may comprise contacting the sample or nucleic acids isolated from the sample, such as total genomic DNA, with one more allele-specific primers and other components of a PCR, such as enzymes and nucleotides, incubating the resulting reaction mixture under the conditions allowing for selective amplification of the mutated nucleic acid sequences, and detecting the presence of the amplified product. Allele-specific PCR can be combined with real-time quantitative PCR in the embodiments of the methods described herein to improve the detection of the of the mutated tumor-associated nucleic acid sequences.

Conventional methods of detecting tumor-associated mutations in blood samples typically employ additional steps for increasing the content of the mutated sequences in the sample prior to performing PCR amplification of the mutant sequences. For example, in one conventional method, isolation of tumor cells from the subject's blood sample prior to PCR amplification is performed to improve the sensitivity of detection of tumor-associated mutations. In another conventional method, non-mutated DNA sequences corresponding to the mutated tumor-associated sequences are subjected to nuclease digestion prior to PCR amplification in order to minimize the background of the non-mutated sequences. Disclosed herein are improved detection methods, which employ quantitative PCR, and can detect tumor-associated mutations in blood samples obtained from the subjects with solid tumor cancers, and, advantageously, do not require additional steps for isolating tumor cells, tumor DNA, or increasing the content of the mutated sequences in the sample prior to performing real-time quantitative PCR.

As discussed above, real-time PCR relies on detection of a measurable parameter, such as fluorescence, during the course of the PCR reaction. The amount of the measurable parameter is proportional to the amount of the PCR product, which allows observe the increase of the PCR product "in real time." Some real-time PCR methods allow for quantification of the input DNA template based on the observable progress of the PCR reaction. The analysis and processing of the data involved is discussed below. A "growth curve" or "amplification curve" in the context of a nucleic acid amplification assay is a graph of a function, where an independent variable is the number of amplification cycles and a dependent variable is an amplification-dependent measurable parameter measured at each cycle of amplification, such as fluorescence emitted by a fluorophore. Typically, the amplification-dependent measurable parameter is the amount of fluorescence emitted by the probe upon hybridization, or upon the hydrolysis of the probe by the nuclease activity of the nucleic acid polymerase, see Holland et al., (1991) *Proc. Natl. Acad. Sci.* 88:7276-7280 and U.S. Pat. No. 5,210,015. In a typical polymerase chain reaction, a growth curve comprises a segment of exponential growth followed by a plateau, resulting in a sigmoidal-shaped amplification plot when using a linear scale. A growth curve is characterized by a "cross point" value or "$C_p$" value, which can be also termed "threshold value" (or $C_t$ value) which is a number of cycles where a predetermined magnitude of the measurable parameter is achieved. A lower $C_p$ value represents more rapid completion of amplification, while the higher $C_p$ value represents slower completion of amplification. Where efficiency of amplification is similar, the lower $C_p$ value is reflective of a higher starting amount of the target nucleic acid, while the higher $C_p$ value is reflective of a lower starting amount of the target nucleic acid. Where a control nucleic acid of known concentration is used to generate a "standard curve," or a set of "control" $C_p$ values at various known concentrations of a control nucleic acid, it becomes possible to determine the absolute amount of the target nucleic acid in the sample by comparing $C_p$ values of the target and control nucleic acids.

The accuracy of the detection by real-time quantitative PCR therefore depends on correct selection of a number of parameters. One parameter that needs to be correctly determined is the range in which $C_p$ values bear linear correlation with the starting amount of the nucleic acid, expressed in log copy number. This range can be termed "valid range" or "assay linearity range" of the real-time PCR assay.

The inventors have found that a blood sample containing genomic DNA not generally known to contain a tumor-associated mutation may nevertheless generate an amplification signal at some genomic DNA concentrations. In some embodiments, this background level of signal is therefore a cutoff below which a signal must fall to be valid, i.e., to be considered different from the background. As noted above, the level of background amplification changes with concentration of genomic DNA. Accordingly, in some embodiments, determination of the presence or absence of a tumor-associated mutation comprises comparison of a threshold value to a control value, wherein the control value is dependent, and varies based upon the concentration of genomic DNA in the sample. Thus, if the cycle threshold for the sample is below the control value then the sample is considered to contain the tumor-associated mutation and if the cycle threshold of the sample is equal to or higher than the control value, the result does not indicate the presence of the tumor-associated mutation, and can be referred to as "negative result"). In some embodiments, such as the testing of NSCLC pM1b metastatic stage patients for an EGFR mutation, such a negative result is indicative, with high likelihood, of the absence of an EGFR mutation in the patients' tumors. In some other embodiments, such as testing of NSCLC patients of a metastatic stage other than pM1b (such as M0 or pM1a), for an EGFR mutation. such a negative result may not be indicative of the absence of an EGFR mutation in the patients' tumors, and re-testing of the patients' tumor tissue should be considered.

In some embodiments, the control value is the highest $C_p$ value or range at which non-specific amplification in the absence of the target DNA occurs, and can be referred to as a "breakthrough" value. In some embodiments, the control value is in fact a range of values, within which a positive value from a sample must fall in order to be considered. Said another way, the range represents possible signal levels outside the typical range of background signal. In some embodiments, the control range is between the above-described breakthrough value and the cycle threshold value of a positive control. In some embodiments, the control value is based on amplification of an internal control, for example another region of the mutated locus that is not mutated frequently.

The improved real-time quantitative PCR methods described herein establish the valid cycle-threshold ($C_t$) range by generating standard curves for control DNA at various levels of genomic DNA in the real-time PCR reaction mixture and selecting the valid cycle-threshold range based on range in which assay linearity is observed. A control or cut-off value for the quantitative real-time PCR reaction is determined according to some other embodiments of the improved methods described herein, below which the non-specific amplification in the absence of the target DNA is not likely to interfere with the quantitative detection of the target DNA present in the reaction mixture. In some other embodiments, the improved methods described herein employ a calibration curve for quantification of a target DNA present in the reaction mixture which takes into account various amounts of genomic DNA present in the sample. Various combinations of improvements of real-time PCR assays discussed above can be incorporated into the improved methods of detection of tumor-associated mutations in blood samples, or another target locus in genomic DNA, thus leading to unexpectedly increased accuracy of such detection.

Calculations and Comparisons

The calculations and comparisons (e.g., of a sample signal to a control value or range) for the methods described herein can involve computer-based calculations and tools. Tools can be advantageously provided in the form of computer programs that are executable by a general purpose computer system (referred to herein as a "host computer") of conventional design. The host computer may be configured with many different hardware components and can be made in many dimensions and styles (e.g., desktop PC, laptop, tablet PC, handheld computer, server, workstation, mainframe). Standard components, such as monitors, keyboards, disk drives, CD and/or DVD drives, and the like, may be included. Where the host computer is attached to a network, the connections may be provided via any suitable transport media (e.g., wired, optical, and/or wireless media) and any suitable communication protocol (e.g., TCP/IP); the host computer may include suitable networking hardware (e.g., modem, Ethernet card, WiFi card). The host computer may implement any of a variety of operating systems, including UNIX, Linux, Microsoft Windows, MacOS, or any other operating system.

Computer code for implementing aspects of the present invention may be written in a variety of languages, including PERL, C, C++, Java, JavaScript, VBScript, AWK, or any other scripting or programming language that can be executed on the host computer or that can be compiled to execute on the host computer. Code may also be written or distributed in low level languages such as assembler languages or machine languages.

The host computer system advantageously provides an interface via which the user controls operation of the tools. In the examples described herein, software tools are implemented as scripts (e.g., using PERL), execution of which can be initiated by a user from a standard command line interface of an operating system such as Linux or UNIX. Those skilled in the art will appreciate that commands can be adapted to the operating system as appropriate. In other embodiments, a graphical user interface may be provided, allowing the user to control operations using a pointing device. Thus, the present invention is not limited to any particular user interface.

Scripts or programs incorporating various features of the present invention may be encoded on various computer readable media for storage and/or transmission. Examples of suitable media include magnetic disk or tape, optical storage media such as compact disk (CD) or DVD (digital versatile disk), flash memory, and carrier signals adapted for transmission via wired, optical, and/or wireless networks conforming to a variety of protocols, including the Internet.

General Considerations Applicable to the Embodiments of the Present Invention

A subject having a solid tumor cancer, such as NSCLC, can have the solid tumor cancer that was not diagnosed prior to the performance of the methods according to the embodiments of the present invention. For example, a subject can be tested for the presence of a tumor-associated mutation, such as EGFR mutant sequences, in blood before or during completion of other diagnostic procedures meant to diagnose the solid tumor cancer. Examples of such diagnostic procedures are various imaging techniques or histological analysis of samples obtained during biopsy. Similar considerations apply to metastatic status and cancer staging of the subjects with solid tumor cancer. Metastatic status, such as M1a or M1b status of NSCLC, and cancer staging can be determined before, concurrently with or subsequently to the methods according to the embodiments of the present invention, which are not limited by the order of various diagnostic steps and procedures performed on the subject.

The methods described herein can employ suitable diagnostic procedures in addition to detection of mutated tumor-associated sequences in the subject's blood, in order to accurately assess the status of the solid tumor cancer in the subject. Additional diagnostic procedures are suitably selected to improve the accuracy of the assessment of the solid tumor cancer in the subject, and can include, but are not limited to, various imaging techniques, biopsies, histological analysis, sequence analysis and other procedures.

The methods described herein are not limited to purely diagnostic procedures, but can also incorporate various treatment steps, thus embodying application and use of the diagnostic discoveries described herein to improved methods of treating solid tumor cancers, one example of which is NSCLC. In one embodiment, the appropriate cancer treatments and diagnostic procedures are suitably selected and administered or performed based on the presence or absence of tumor-associated mutations in the blood of a subject with a solid tumor cancer, such as the presence or absence of tumor-associated EGFR mutations detected in the blood of NSCLC subject. Cancer treatments described herein can include surgical or non-invasive treatments, such as drug or radiation therapies.

Tumor-Associated Mutations

Tumor-associated mutations that are detected according to the methods described herein are mutations that are found in tumors of subjects with solid tumor cancers and affect development of the solid tumor cancers in the subjects. For example, tumor-associated mutations can affect the emergence, progression or recurrence of the cancer, as well as the responsiveness or susceptibility of the cancer to a cancer therapy. One example of tumor-associated mutations that can be detected according to the methods described herein is the mutations in proto-oncogenes that convert them into oncogenes. Another example is the mutations in tumor-suppressor gene that result in the loss or decrease of their function. The mutations that can be detected according to the methods of the present invention are not limited to the mutations in protein-encoding genes, but can also include the mutations in non-coding nucleic acid sequences, such as regulatory elements, sequences encoding non-coding RNA, and other non-coding sequences. Tumor-associated mutations of the protein-coding nucleic acid sequences can be in-frame deletions or insertions, as well as substitutions. For example, mutated EGFR sequences being detected are typically nucleic acid sequences that contain one or more in-frame nucleotide deletions or insertions, as well as nucleotide substitutions that result in mutated amino acid sequence of EGFR. Tumor-associated mutations can result in protein fusions. Some examples of tumor-associated mutations that can be detected in patient's blood and used to monitor cancer emergence, progression, recurrence, as well as to monitor cancer therapy, include without limitation, the following mutations: EGFR mutations, KRAS mutations, including mutations in KRAS codons 12, 13, 61 and 146, ALK mutations, including ALK fusions, ROS1, including ROS1 fusions, c-MET mutations, PIK3CA (PI3K-CA) mutations, NRF2 mutations, FGFR1-3 mutations, AKT1 mutations, including AKT1 fusions, BRAF mutations, including V600E substitution, NRAS mutations, TMPRSS2:ERG fusion, SPOP mutations, RET fusions, PPAR-gamma fusions, IDH-1 mutations, and IDH-2 mutations. It is to be understood that some of the above mutations are associated with some, but not necessarily all, of the solid tumor cancers. Accordingly, detection of some of the above tumor-associated mutations can be more suitable for assessment of certain cancers. For example, detection of the following mutations can be suitable for assessment of lung cancer: EGFR mutations, KRAS mutations, ALK fusions, ROS1 fusions, c-MET mutations, PIK3CA (PI3K-CA) mutations, NRF2 mutations and FGFR1-3 mutations. In another example, detection of AKT1 mutations, including fusions, can be suitable for assessment of breast cancer. In one more example, detection of KRAS mutations, such as mutations of codons 12, 13, 61 and 146, BRAF substitution V600E, NRAS mutations, PIK3CA (PI3K-CA), EGFR extracellular domain hot spot mutations can be used for assessment of colorectal cancer. Detection of TMPRSS2:ERG fusion and SPOP mutations can be used for assessment of prostate cancer. Detection of BRAF mutations, NRAS mutations, RET fusion and PPAR gamma fusion can be used for assessment of thyroid cancer. Detection of mutations in IDH-1 and IDH-2 can be used for assessment of glioblastoma, while detection of mutations in FGFR3 can be used for detection of bladder cancer. It is to be understood that the above list of the associations of the tumor-associated mutations and types of cancers is not exhaustive or limiting.

Non-Small Cell Lung Cancer

Lung cancer is a solid tumor cancer that forms in lung tissue. Most of the lung cancer begins in the epithelial cells lining air passages. This type of cancer is termed "Non-Small Cell Lung Cancer" (NSCLC). The other, less prevalent, type of lung cancer is termed "Small-Cell Lung Cancer," which begins in the non-epithelial lung cells, such as nerve cells or hormone-producing cells. The classification of the lung cancer into NSCLC and small cell is important for determining an appropriate treatment. Lung cancer is also described in terms of staging, which describes the extent of cancer in a patient's body. In the current clinical practice, lung cancer is typically staged according to Classification of Malignant Tumors (TNM), developed and maintained by the International Union Against Cancer (UICC). TNM classification takes into account the size of the tumor and whether it has invaded nearby tissue, involvement of regional lymph nodes, and distant metastasis, or spread of cancer from one body part to another. According to current TNM classification of lung cancer is divided into five stages. Stage 0 is also called in situ lung cancer, meaning that the cancer did not invade tissues outside the lung. Stage I lung cancer is a small tumor that has not spread to any lymph nodes and cam be completely surgically removed. Stage I is divided into two sub-stages, A and B, based on the size of the tumor. Small tumors, such as those less than 3 cm are classified as stage IA. Stage I tumors between 3 and 5 cm are typically classified as stage IB lung cancer. Stage II typically refers to larger tumors, with sub-stage IIA describing the tumors larger tumor (over 5 cm but less than 7 cm wide) that has spread to the lymph nodes or a larger tumor (more than 7 cm wide) that may or may not have invaded nearby structures in the lung but has not spread to the lymph nodes.

When lung cancer metastasizes, it spreads through blood or lymph vessels after breaking away from a lung tumor. Stage III describes the cancer tumors that are difficult to remove, because they spread to the tissues outside of the lung. Stage III cancers are classified as either stage IIIA or IIIB. For many stage IIIA cancers and nearly all stage IIIB cancers, the tumor is difficult, and sometimes impossible, to remove. For example, stage IIIB lung cancer may spread to the lymph nodes located in the center of the chest, or invade nearby structures in the lung. Stage IV typically describes lung cancer that has spread to more than one area in the other lung, the fluid surrounding the lung or the heart, or distant parts of the body by the process of metastasis. The terms "stage IVA" can be used to describe lung cancer that spread within the chest, while the term "stage IVB" when it has spread outside of the chest. In general, surgery is not successful for most stage III or IV lung cancer. Lung cancer can also be impossible to remove if it has spread to the lymph nodes above the collarbone, or if the cancer has grown into vital structures within the chest, such as the heart, large blood vessels, or the main breathing tubes leading to the lungs. Stage III and IV lung cancer can be described as "late stage lung cancer" or "advanced lung cancer."

Late stage or advanced lung cancer can be characterized in terms of its metastatic status or metastatic stage. For example, so-called metastasis stages M0 and M1 can be used to refer to the cancer's metastatic status. M0 metastatic status typically indicates that no metastasis of a lung tumor is detected in a patient. M1 status typically indicates that metastasis is detected. M1 metastatic status can be further subdivided into stages M1a and M1b. Metastatic stage M1a is typically used to describe metastatic lung cancer in which separate tumor nodule or nodules appear in a contralateral lung lobe, lung cancer tumors with pleural nodules or malignant pleural or pericardial effusions. Metastatic status of NSCLC cancer in a subject can be determined by various diagnostic procedures, including imaging techniques, such as PET scanning, or histological examinations of tissue samples obtained by biopsy. Metastatic stage M1b is typically used to describe lung cancer with distant metastasis in extrathoracic organs.

Epidermal Growth Factor Receptor

Epidermal Growth Factor Receptor (EGFR), which is also known as HER-1 or Erb-B1, is an oncogene involved in development and progression of NSCLC in some patients. EGFR is a membrane-bound receptor protein of Erb family. EGFR comprises an extracellular ligand-binding domain, a transmembrane domain, and an intracellular domain that possesses tyrosine kinase activity. EGFR is inactive in its monomeric state. Binding of a ligand leads to homo and heterodimerization of EGFR with other HER family members, followed by intermolecular tyrosine phosphorylation. Adaptor or signaling molecules bind to phosphorylated EGFR, which triggers downstream intracellular signaling cascades. Examples of the signaling cascades triggered by EGFR are Akt, STAT and MAPK cascades. EGFR is promotes growth of various cancers by several mechanisms, including, but not limited to, EGFR amplification, and mutational activation of EGFR.

Anti-cancer therapeutic drugs were developed that inhibit tyrosine kinase inhibitory activity of EGFR. Two of such drugs are small molecules gefitinib and erlotinib, which belong to the class of quinazoline derivatives. Gefitinib and erlotinib were both shown to inhibit EGFR tyrosine phosphorylation. In the clinical studies that led to approval of gefitinib and erlotinib, the drugs were shown to prolong survival in a relatively small subset of non-small cell lung cancer (NSCLC) patients after chemotherapy. Subsequent studies revealed that mutations in EGFR tyrosine kinase domain were present in a portion of NSCLC patients, and that these mutations were associated with clinical responsiveness to gefitinib and erlotinib. EGFR mutations which were associated with resistance to gefitinib and erlotinib were also identified. Discussion of the early developments in the area of EGFR mutations in NSCLC patients and their connection to gefitinib and erlotinib therapies is found, for example, in Pao and Miller, *Journal of Clinical Oncology*, 23:2556-2568 (2005) and Rosell et al., *Clin. Cancer. Res.* 12:7222-7231, incorporated herein by reference. The presence or absence of EGFR mutations in NSCLC patients can therefore serve as a marker suitable for assessing the status of NSCLC in patients, such as determining whether a particular patient's NSCLC is potentially responsive to EGFR-directed therapy.

Known EGFR mutations associated with drug susceptibility or resistance to known targeted drug therapies are generally located in the tyrosine-kinase domain of EGFR. Some of the known mutations are illustrated in FIG. 1, and in Table 1. Some of these mutations are classified into "activating mutations," which enhance EGFR signaling. Some of the activating EGFR mutations are associated with sensitivity to targeted drug therapies, such as tyrosine kinase inhibitor therapies, and are sometimes referred to as "sensitizing" mutations. Examples of such mutations are in frame deletions EGFR exon 19, and some amino-acid substitutions, such as L858R, L861Q and substitutions at G719, sometimes referred to as G719X, which include, but are not limited to G719A, G719C and G719S.

Other EGFR mutations are associated with resistance to tyrosine kinase inhibitor therapies, and often arise in the course of the therapy. Such mutations can be referred to as "resistance" mutations, examples of which are in frame EGFR exon 20 insertions and T790M and S678I amino acid substitutions. The methods described herein employ detection of EGFR mutations, including activating and resistance mutations, in the blood of a subject with NSCLC.

EXAMPLES

Example 1

Isolation of Nucleic Acids and PCR Amplification

All the samples were acquired from lung cancer (NSCLC) patients. Nucleic acid isolation was performed utilizing COBAS® DNA Sample Preparation Kit (Roche Molecular Diagnostics, Indianapolis, Ind.) according to the manufacturer's instructions. Real-time alleles-specific PCR amplification was performed on a COBAS® instrument using COBAS® EGFR Mutation Test kit (Roche Molecular Diagnostics) according to the manufacturer's instructions. Briefly, the COBAS® kit contains three reaction mixtures, MMX1, MMX2, and MMX3, for allele-specific real-time PCR detecting various mutations in the human EGFR gene. MMX1 comprises primers and 6-carboxyfluorescein (FAM)-labeled probes for multiple deletions in exon 19 of the human EGFR gene (termed Ex19Del) and substitution mutation S768I (JA270 signal). MMX2 comprises primers and probes for substitution mutation L858R (FAM signal) and mutation T790M (JA270 signal). MMX3 comprises primers and probes for substitution mutation L861Q (FAM signal), a set of substitution mutations G719X (HEX signal) and multiple insertions in exon 20 of the human EGFR gene (Ex20Ins) (JA270 signal). Each reaction further comprises internal control (IC) primers and probes targeting exon 28 of the human EGFR gene (Cy5.5 signal).

Example 2

Establishing a Calibration Curve for the Quantification of DNA Targets

Figure 2:
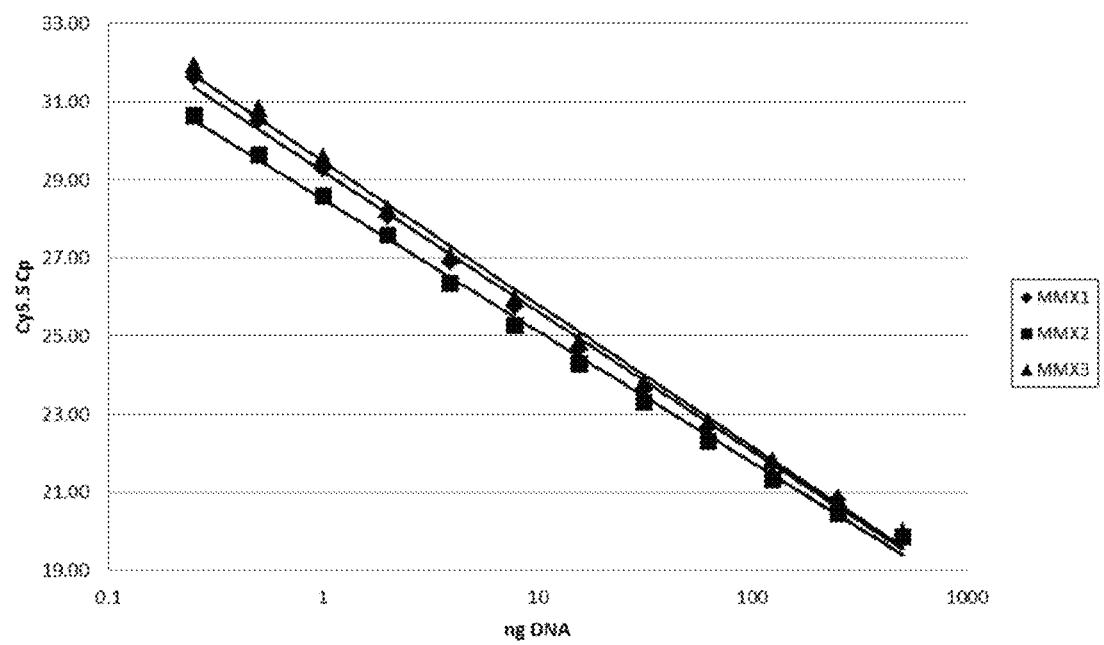
FIG. 2 is a plot illustrating experimental data on real-time PCR cross-point (Cp) values obtained with COBAS® EGFR Mutation Test kit using reaction mixtures MMX1, MMX2 and MMX 3 in the presence of different levels of genomic DNA. The X-axis represents genomic DNA level (ng per reaction) and the Y-axis represents cycle number corresponding to the $C_p$ achieved in a reaction.

To calibrate the assay, varying amounts of genomic DNA were subjected to real-time PCR amplification using the COBAS® EGFR Mutation Test kit. Twelve levels of genomic DNA were tested: 0.25, 0.5, 1, 2, 4, 8, 16, 32, 64, 125, 250 and 500 ng/reaction. At each genomic DNA level, 120 replicate PCR assays were run with internal control (IC) primers and probes in three different multiplex PCR reaction mixtures included in the kit (MMX1, 2 and 3, see Example 1). The resulting standard curve is shown in FIG. 2. On FIG. 2, the X-axis represents genomic DNA level and the Y-axis represents cycle number corresponding to the cross point ($C_p$) achieved in the reaction. Based on the experimental data illustrated by FIG. 2, the valid range of the internal control values (IC $C_p$ range) was set at 20-32. In the selected valid $C_p$ range, assay linearity was observed for all the reaction mixtures tested.

Example 3

Establishing a Cut-Off Limit for the Quantitative PCR Assay

For each reaction mixture, a measurable range within the valid IC $C_p$ range was established using the data from non-specific amplification in the absence of the true target occurring at later cycles of PCR, which was termed "breakthrough amplification." For each reaction mixture, breakthrough amplification was observed with at least one set of primers and probes. For each target within each reaction mixture, the value of $C_pR$ was determined, which was the difference between the internal control signal and the breakthrough signal, calculated as the difference between breakthrough $C_p$ and internal control $C_p$ observed in the same reaction. For example, for Ex19del target (illustrated in Table 2), breakthrough occurred at the higher levels of genomic DNA tested, but $C_pR$ was consistently high at these levels. The minimum $C_pR$ observed was selected as a cut-off value. The target Ex19del signal was considered positive (mutation detected) only if the IC value Cp was in the valid range, as discussed in Example 2, and the $C_pR$ value (the difference between the target and the control signal) fell below the cut-off value of 17.7.

Alternatively, the cut-off may be set simply as the lowest breakthrough $C_p$ observed in the calibration example. As illustrated in Table 2, for the S768I target, the target signal was considered positive (mutation detected) only if the IC value was in the valid range and the target $C_p$ value was below the breakthrough threshold of 34 cycles.

Example 4

Figure 3:
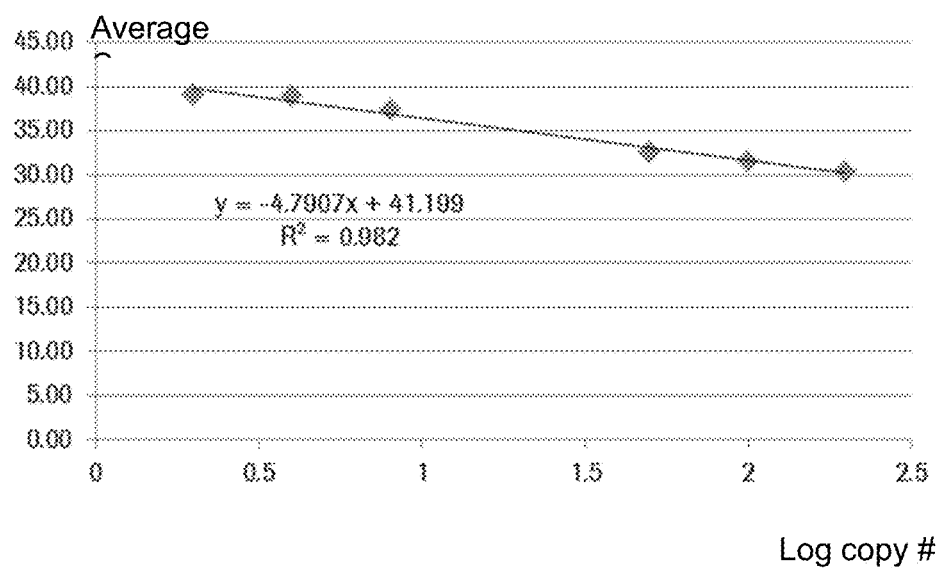
FIG. 3 is a plot schematically showing an exemplary calibration curve for quantification of a target nucleic acid.

Establishing a Calibration Curve for the Quantification of a Mutant Target in the Presence of Wild-Type Genomic DNA Target To approximate patients' samples containing cancer cells and normal cells, as well as genomic DNA, various amounts of each mutant target detectable by the assay (see Example 1) were combined with various amounts of wild-type genomic DNA. Different amounts of the target nucleic acid containing T790M mutation (2, 4, 8, 50, 100, or 200 ng/reaction) were combined with different amounts of wild-type genomic DNA background (0.25, 0.5, 1.0, 2.0, 3.9, 7.8, 15.6, 31.3, 62.5, 125, 250, and 500 ng/reaction). The target-specific $C_p$ obtained in the experiment was then plotted against the amount of input target DNA. The signal for T790M-specific probe (JA270 $C_p$) obtained at different levels of target DNA was averaged and plotted against the log copy number of the T790M mutant target present in the sample. The resulting calibration curve is shown in FIG. 3.

Example 5

Detecting Mutant EGFR DNA in the Blood of Lung Cancer (NSCLC) Patients

Figure 4:
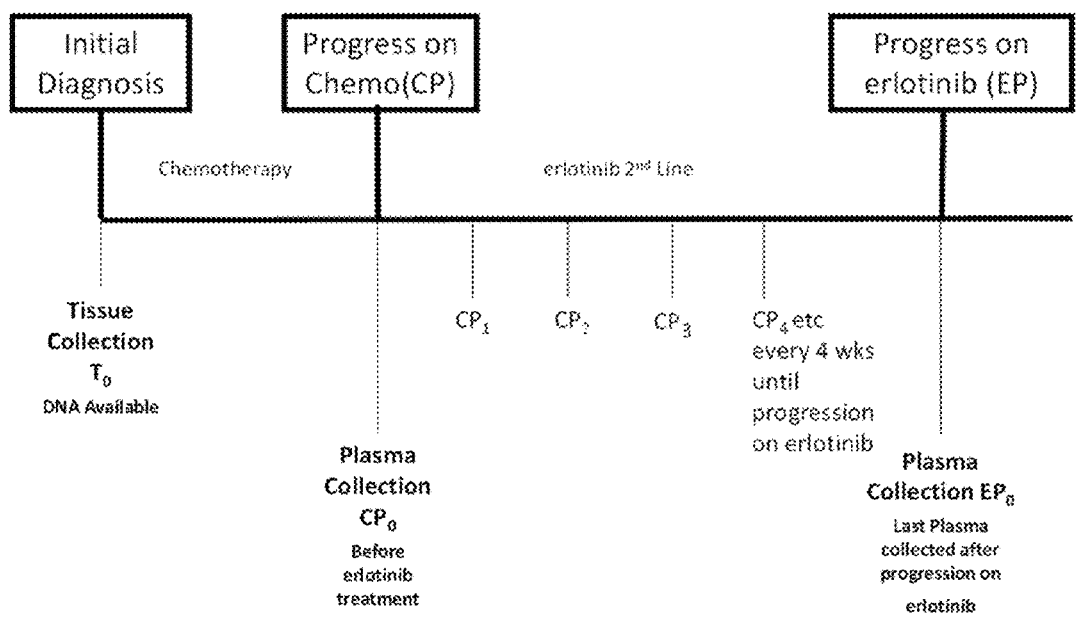
FIG. 4 is a schematic representation of NSCLC treatment timeline and sample collection.
Figure 5:
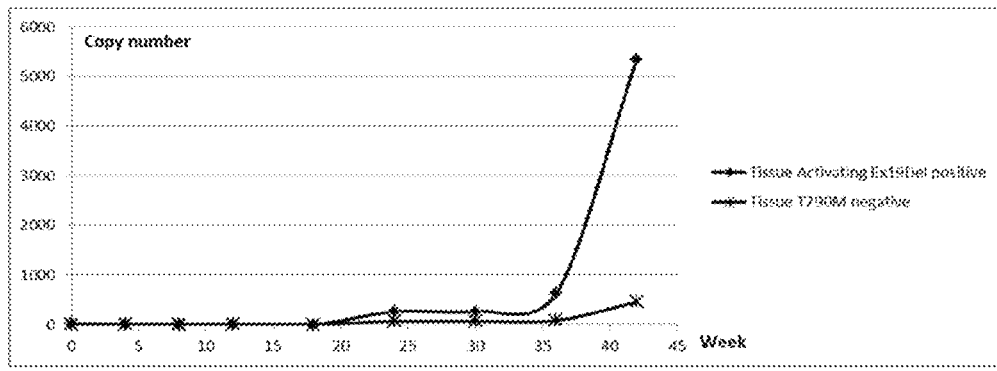
FIG. 5 is a plot illustrating detection of EGFR mutations in the plasma samples of two exemplary NSCLC patients. Week 0 on the X-axis corresponds to time point $CP_0$ before the start of erlotinib treatment in FIG. 3.
Figure 5:
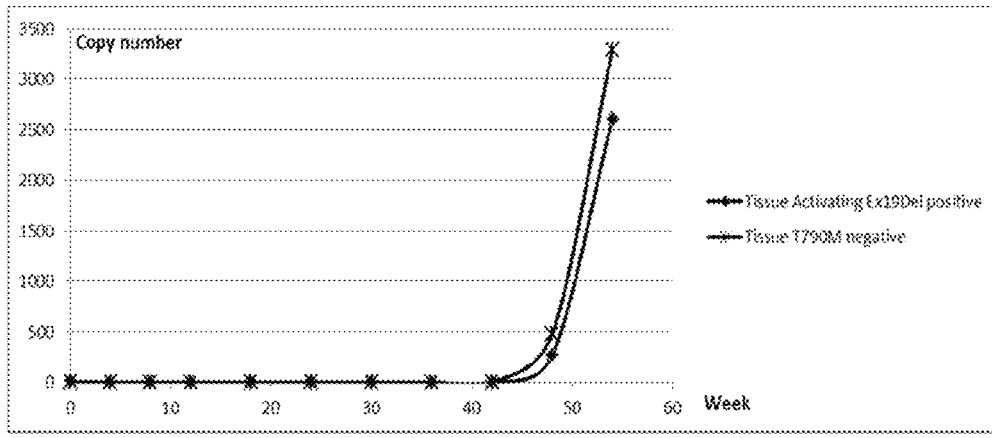

Blood plasma samples were collected from NSCLC patients after they underwent chemotherapy and before and during erlotinib targeted therapy. The timeline of the sample collection is schematically illustrated in FIG. 4. The samples were collected every four weeks at the time points indicated as $CP_{0-4}$ in FIG. 4. Sample collection did not necessarily stop at time point $CP_4$. DNA was isolated from the collected blood plasma samples and subjected to real-time PCR amplification using the COBAS® kits in accordance with manufacturer's instructions (see Example 1). For illustrative purposes, FIG. 5 schematically shows measured levels of an activating exon 10 deletion (Ex19Del) and T790M activating substitution of EGFR in blood plasma of two exemplary patients ("Case A" and "Case B"). In both patients, tissue tumor samples obtained at the initial diagnosis had been previously determined to contain an activating EGFR mutation (Ex19del) but no resistance mutation (T790M). The amount of mutant DNA sequences, expressed in number of copies and plotted on Y-axis of the plot shown in FIG. 5, was measured using the calibration curves described in Example 5. In both cases A and B, increase in the amount of mutant DNA in the blood correlated with progression of NSCLC as detected by suitable imaging techniques and also indicated the rise of resistance to erlotinib therapy.

Example 6

Detection of EGFR Mutations in the Blood of NSCLC Patients with Different Metastasis Statuses Two studies were conducted that correlated detection of EGFR mutations in the blood plasma of NSCLC patients with the patient's metastasis status. In the first study (Study I), plasma samples and matching tissue samples were collected from twenty eight Stage IV NSCLC patients. Mutation status of the tissue and blood samples was determined. The data on the mutations detected in was compared to the metastasis status of the patients. Study I experimental data is summarized in Tables 3 and 4.

In the second study (Study II), plasma samples and matching tissue samples were collected from seventeen Stage IV NSCLC patients. Mutation status of the tissue and blood samples was determined. The data on the mutations detected in was compared to the metastasis status of the patients. Study II experimental data is summarized in Tables 5-I, 5-II and 6.

In both Study I and Study II, it was observed that positive agreement between detection of EGFR mutations in tissue and plasma samples was significantly higher for the patients with distant metastasis (metastatic status pM1 b) than for the patient without distant metastasis (metastatic status pM1 a). Summary of Study I and Study II data on detection of activating EGFR mutations in blood of NSCLC patients of different metastatic status is schematically shown in Table 7.

Example 7

Figure 6:
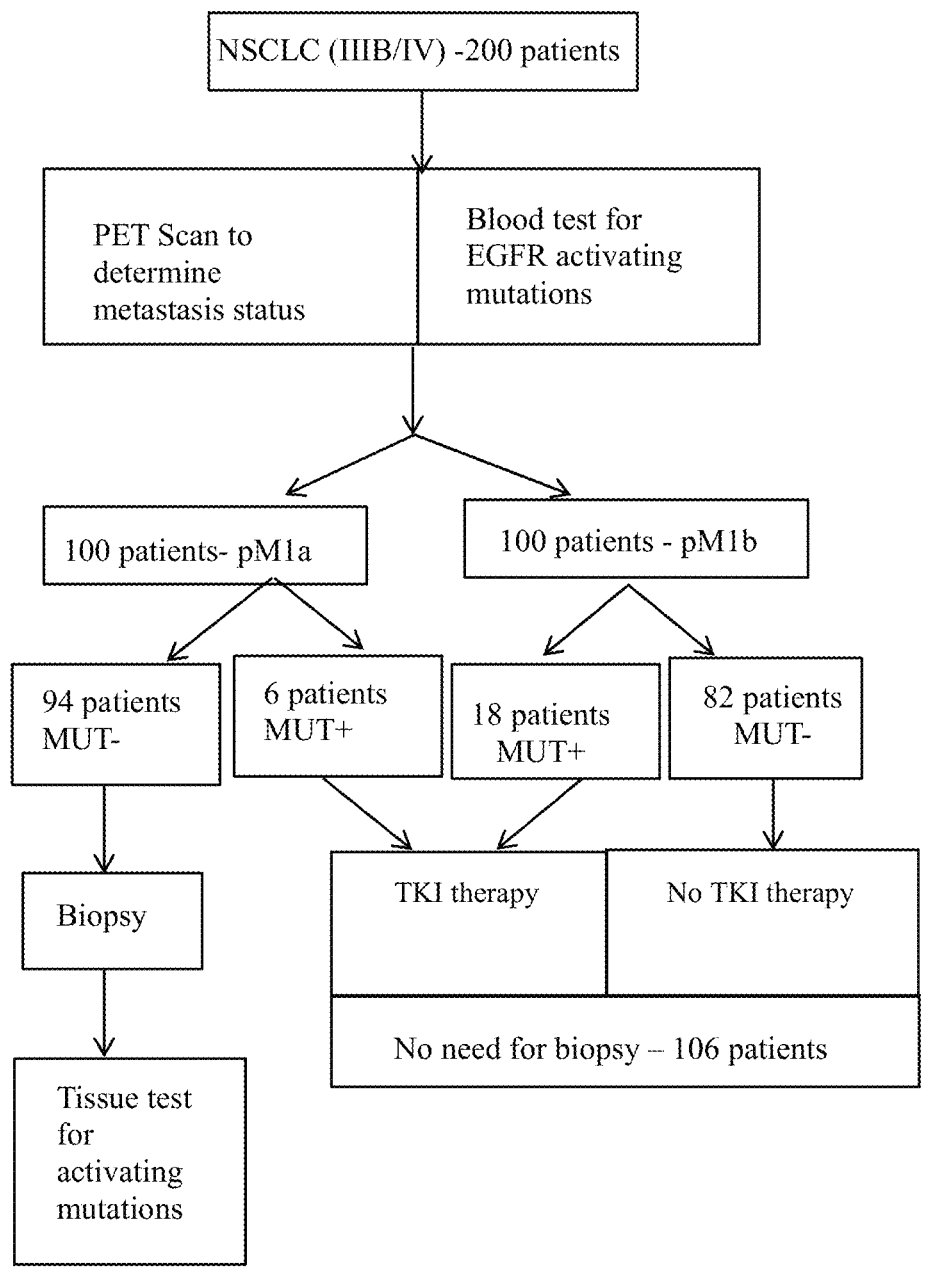
FIG. 6 is a schematic representation of the decision-making process for treatment and diagnosis of patients presenting with NSCLC patients based on blood testing for EGFR activating mutations.

Benefits of Detecting EGFR Mutations in the Blood of Initially Diagnosed NSCLC Patients EGFR activating mutations are detected in blood of 200 patients with initially diagnosed stage IIIB through stage IV NSCLC. The detection is generally performed according to the procedures described in the earlier examples. Activating EGFR mutations are detected in the blood of 20% of the patients. Resistance EGFR mutations are detected in a subset of the patients carrying activating EGFR mutations. Metastasis status of these patients is determined by PET Scan. 50% of the patients are determined to have pM1a metastasis status, and 50% are determined to have pM1b metastasis status. Based on the knowledge of the high positive agreement between detection of the activating EGFR mutations in blood and their presence in tumor tissue in pM1b patients but not in pM1a patient, targeted tyrosine kinase inhibitor (TKI) therapy is recommended for and administered to pM1b and pM1a patients with detectable EGFR activating mutations in blood without additional diagnostic procedures. Targeted TKI therapy is not recommended for pM1b patients without detectable EGFR activating mutations or with detectable resistance mutations in blood (no additional diagnostic procedures are deemed necessary). pM1 a patients without detectable EGFR activating mutations in blood are directed to biopsy of the tumor tissue with subsequent mutation detection in the biopsy samples in order to determine whether or not these patients are candidates for EGFR therapy. The above decision-making process for 200 patients is schematically illustrated in FIG. 6. Under this decision-making process, only 94 patients out of 200 need biopsy followed by tissue mutation testing in order to determine whether or not they are candidates for TKI targeted therapy.

Example 8

Benefits of Detecting EGFR Mutations in the Blood of Relapsed NSCLC Patients

Figure 7:
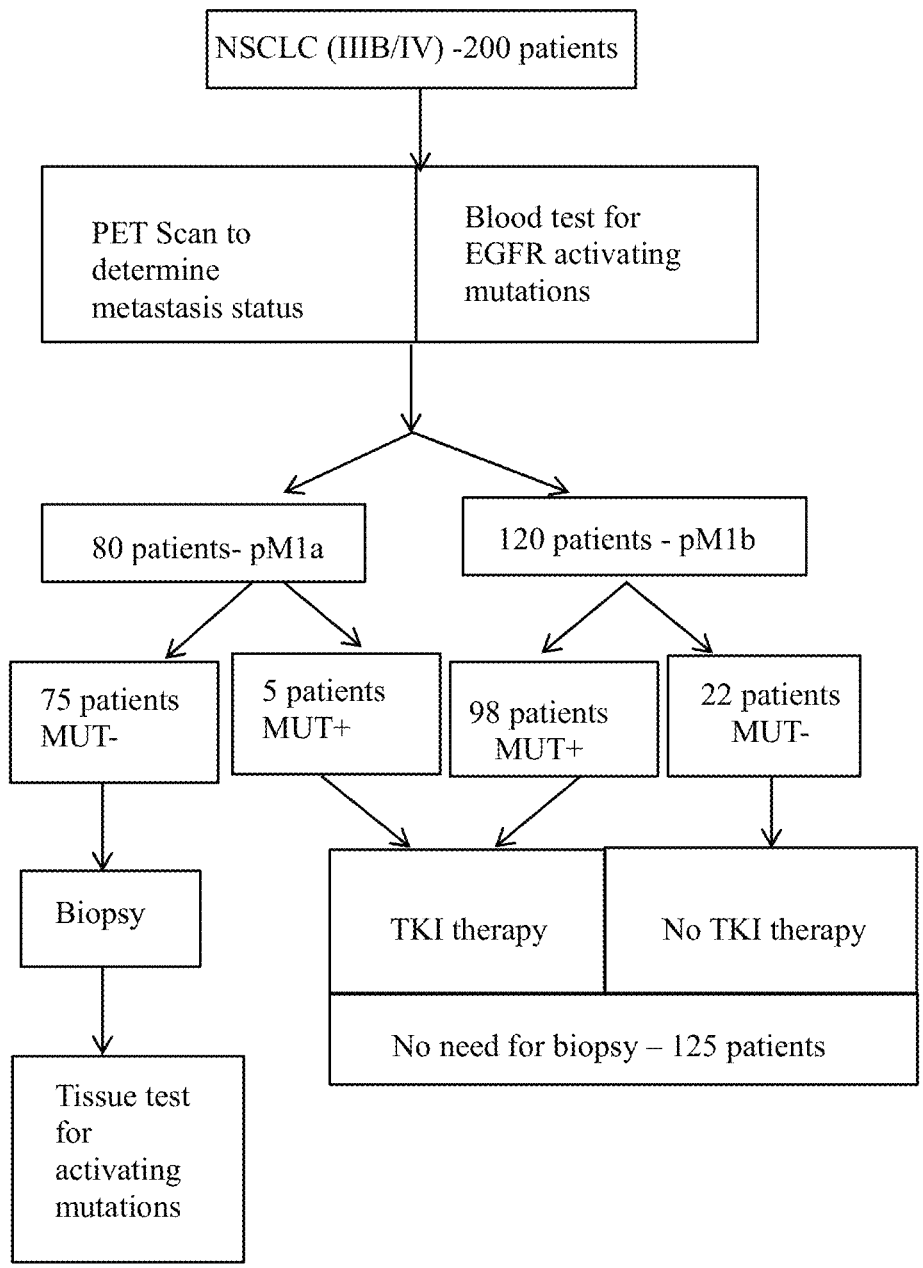
FIG. 7 is a schematic representation of the decision-making process for treatment and diagnosis of relapsing NSCLC patients based on blood testing for EGFR activating mutations.

EGFR activating mutations are detected in blood of 200 relapse patients with stage IIIB through stage IV NSCLC. The detection is generally performed according to the procedures described in the earlier examples. Activating EGFR mutations are detected in the blood of 20% of the patients. Metastasis status of these patients is determined by PET Scan. 40% of the patients are determined to have pM1a metastasis status, and 60% are determined to have pM1b metastasis status. Based on the knowledge of the high positive agreement between detection of the activating EGFR mutations in blood and their presence in tumor tissue in pM1b patients but not in pM1a patient, targeted tyrosine kinase inhibitor (TKI) therapy is recommended for and administered to pM1b and pM1a patients with detectable EGFR activating mutations in blood without additional diagnostic procedures. Targeted TKI therapy is not recommended pM1b patients without detectable EGFR activating mutations in blood (no additional diagnostic procedures are deemed necessary). pM1a patients without detectable EGFR activating mutations in blood are directed to biopsy of the tumor tissue with subsequent mutation detection in the biopsy samples in order to determine whether or not these patients are candidates for EGFR therapy. The above decision-making process for 200 patients is schematically illustrated in FIG. 7. Under this decision-making process, only 74 patients out of 200 need biopsy followed by tissue mutation testing in order to determine whether or not they are candidates for TKI targeted therapy.

Example 9

Benefits of Detecting EGFR Mutations in the Blood of NSCLC Patients

Figure 8:
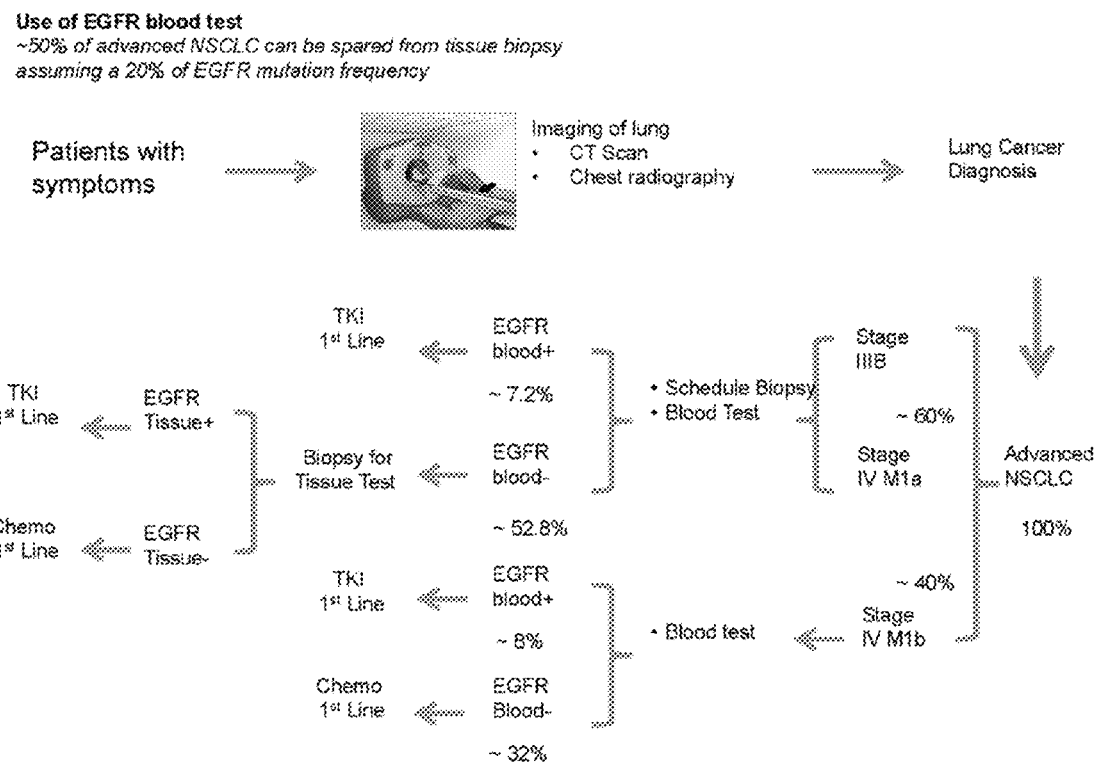
FIG. 8 is a schematic representation of the decision-making process for treatment and diagnosis of NSCLC patients.

EGFR activating mutations are detected in blood of 200 relapse patients with stage IIIB through stage IV NSCLC. The detection is generally performed according to the procedures described in the earlier examples. The decision-making process is schematically illustrated in FIG. 8.

TABLE 1

Examples of EGFR mutations.

| Mutation | Amino Acid Change | Exon |
|---|---|---|
| 2155 G > A | G719S | 18 |
| 2155 G > T | G719C | 18 |
| 2156 G > C | G719A | 18 |
| 2233_2247del15 | K745_E749del | 19 |
| 2235_2248 > AATTC | E746_A750 > IP | 19 |
| 2235_2249del15 | E746_A750del | 19 |
| 2235_2251 > AATTC | E746_T751 > IP | 19 |
| 2235_2252 > AAT | E746_T751 > I | 19 |
| 2235_2255 > AAT | E746_S752 > I | 19 |
| 2236_2250del15 | E746_A750del | 19 |
| 2236_2253del18 | E746_T751del | 19 |
| 2237_2251del15 | E746_T751 > A | 19 |
| 2237_2252 > T | E746_T751 > V | 19 |
| 2237_2253 > TTGCT | E746_T751 > VA | 19 |
| 2237_2254del18 | E746_S752 > A | 19 |
| 2237_2255 > T | E746_S752 > V | 19 |
| 2237_2257 > TCT | E746_P753 > VS | 19 |
| 2238_2248 > GC | L747_A750 > P | 19 |
| 2238_2252del15 | L747_T751del | 19 |
| 2238_2252 > GCA | L747_T751 > Q | 19 |
| 2238_2255del18 | E746_S752 > D | 19 |
| 2239_2247del9 | L747_E749del | 19 |

TABLE 1-continued

Examples of EGFR mutations.

| Mutation | Amino Acid Change | Exon |
|---|---|---|
| 2239_2248 > C | L747_A750 > P | 19 |
| 2239_2251 > C | L747_T751 > P | 19 |
| 2239_2253del15 | L747_T751del | 19 |
| 2239_2256del18 | L747_S752del | 19 |
| 2239_2256 > CAA | L747_S752 > Q | 19 |
| 2239_2258 > CA | L747_P753 > Q | 19 |
| 2240_2251del12 | L747_T751 > S | 19 |
| 2240_2254del15 | L747_T751del | 19 |
| 2240_2257del18 | L747_P753 > S | 19 |
| 2253_2276del24 | S752_I759del | 19 |
| 2303 G > T | S768I | 20 |
| 2307_2308 ins 9(GCCAGCGTG) | V769_D770insASV | 20 |
| 2309_2310(AC > CCAGCGTGGAT (SEQ ID NO: 1) | V769_D770insASV | 20 |
| 2310_2311 ins GGT | D770_N771insG | 20 |
| 2311_2312 ins 9(GCGTGGACA) | D770_N771insSVD | 20 |
| 2319_2320 ins CAC | H773_V774insH | 20 |
| 2369 C > T | T790M | 20 |
| 2573 T > G | L858R | 21 |
| 2573-2574TG > GT | L858R | 21 |

TABLE 3

Summary of Study I experimental data.

| EGFR Activating Mutations Tissue MUT+ | Plasma MUT+* | | Plasma MUT-** |
|---|---|---|---|
| | 13 (metastasis status of 2 samples not known) | | 3 |
| | pM1a | pM1b*** | pM1a | pM1b |
| | 2 | 9 | 3 | 0 |

*MUT+ = activating mutation detected
**MUT− = activating mutation not detected
***Metastasis status of some of the patients was not known

TABLE 4

Summary of Study I experimental data for the patients with detectable mutations in tissue samples.

| Patient ID | Mutations detected in tissue sample | Mutations detected in plasma sample | Metastasis status |
|---|---|---|---|
| 1 | L858R&T790M | L858R & T790M | N/D* |
| 2 | Ex19Del | Ex19Del | N/D |
| 3 | L858R | L858R | pM1b |
| 4 | S768I, G719X | S768I & G719X | pM1b |
| 5 | L858R | L858R | pM1b |
| 6 | Ex19Del | Ex19Del | pM1a |
| 7 | Ex19Del | Ex19Del & T790M | pM1b |
| 8 | Ex19Del | Ex19Del | pM1b |
| 9 | Ex19Del | Ex19Del | pM1b |
| 10 | Ex19Del | Ex19Del | pM1b |
| 11 | Ex19Del | Ex19Del | pM1b |
| 12 | Ex19Del | Ex19Del | pM1b |
| 13 | L858R | L858R | pM1a |
| 14 | L858R&Ex20Ins | — | pM1a |
| 15 | L858R and T790M | — | pM1a |
| 16 | Ex19Del & T70M | — | pM1a |

*N/D = not determined

TABLE 2

Summary of the exemplary experimental data used for establishing cut-off limits for a measurable range of quantitative PCR assays.

Breakthrough Data

| | | | Ex 19 Deletion | | | | | S768I | | | | |
|---|---|---|---|---|---|---|---|---|---|---|---|---|
| Genomic DNA, ng per reaction | # of reactions | Average IC $C_p$ | # of reactions with observed breakthrough | Average breakthrough $C_p$ | Minimum breakthrough $C_p$ | Average $C_pR$ | Minimum $C_pR$ | # of reactions with observed breakthrough | Average breakthrough $C_p$ | Minimum breakthrough $C_p$ | Average $C_pR$ | Minimum $C_pR$ |
| 500 | 120 | 19.89 | 1 | 40 | 40 | 20.19 | 20.19 | 4 | 39.01 | 38 | 19.06 | 17.82 |
| 250 | 120 | 20.81 | 3 | 40.42 | 38.79 | 19.65 | 18.16 | 0 | NA | NA | NA | NA |
| 125 | 120 | 21.72 | 0 | NA* | NA | NA | NA | 1 | 34.01 | 34.01 | 12.27 | 12.27 |
| 62.5 | 120 | 22.67 | 1 | 40.37 | 40.37 | 17.7 | 17.7 | 1 | 39.02 | 39.02 | 16.18 | 16.18 |
| 31.3 | 120 | 23.65 | 0 | NA | NA | NA | NA | 2 | 34.53 | 34.19 | 10.84 | 10.56 |
| 15.6 | 120 | 24.67 | 0 | NA | NA | NA | NA | 0 | NA | NA | NA | NA |
| 7.8 | 119 | 25.74 | 0 | NA | NA | NA | NA | 2 | 34.36 | 34.29 | 8.44 | 8.41 |
| 3.9 | 119 | 26.87 | 0 | NA | NA | NA | NA | 0 | NA | NA | NA | NA |
| 2 | 119 | 28.05 | 0 | NA | NA | NA | NA | 0 | NA | NA | NA | NA |
| 1 | 120 | 29.28 | 0 | NA | NA | NA | NA | 0 | NA | NA | NA | NA |
| 0.5 | 107 | 30.50 | 0 | NA | NA | NA | NA | 0 | NA | NA | NA | NA |
| 0.25 | 107 | 31.61 | 0 | NA | NA | NA | NA | 0 | NA | NA | NA | NA |

*NA stands for "not applicable"

TABLE 5-I

Summary of Study II experimental data

| EGFR Activating Mutations | Plasma MUT+* | | Plasma MUT-** | |
|---|---|---|---|---|
| Tissue MUT+ | 11 | | 4 | |
| | pM1a*** | pM1b | pM1a | pM1b |
| | 1 | 9 | 3 | 1 |

*MUT+ = activating mutation detected
**MUT- = activating mutation not detected
***Metastasis status of some of the patients was not known

TABLE 5-II

Summary of Study II experimental data

| EGFR resistance mutation T790M | Plasma MUT+* | | Plasma MUT-** | |
|---|---|---|---|---|
| Tissue MUT+ | 6 | | 3 | |
| | pM1a | pM1b | pM1a | pM1b |
| | 1 | 5 | 2 | 1 |

*MUT+ = activating mutation detected
**MUT- = activating mutation not detected
***Metastasis status of some of the patients was not known

TABLE 6

Summary of Study II experimental data

| Patient ID | Mutations detected in tissue sample | Mutations detected in plasma sample | Metastasis status |
|---|---|---|---|
| 1 | Ex19Del | Ex19Del | pM1b |
| 2 | L861Q & G719X & T790M | L861Q & G719X & T790M | pM1b |
| 3 | Ex19Del | Ex19Del | pM1b |
| 4 | L858R | L858R | pM1b* |
| 5 | L858R & T790M | L858R & T790M | pM1b |
| 6 | L858R & T790M | L858R & T790M | pM1b |
| 7 | Ex19Del & T790M | Ex19Del & T790M | pM1b |
| 8 | Ex19Del & T790M | Ex19Del & T790M | pM1b |
| 9 | L858R | L858R | pM1b |
| 10 | Ex19Del & T790M | Ex19Del & T790M | pM1a |
| 11 | Ex19Del & T790M | Ex19Del & T790M | N/D |
| 12 | T790M (Ex19Del) | — | pM1a |
| 13 | Ex19Del & T790M | — | pM1a |
| 14 | Ex19Del & T790M | — | pM1b |
| 15 | Ex19De | — | pM1b |
| 16 | — | Ex19Del | pM1b |
| 17 | — | Ex19Del | pM1b |

*N/D = not determined

TABLE 7

Summary of Study I and Study II data on detection of activating EGFR mutations in blood of NSCLC patients of different metastasis status.

| Study | Metastasis status | Positive agreement | Negative agreement | Overall agreement |
|---|---|---|---|---|
| I | Overall* | 81% | 100% | 89% |
| | pM1a | 40% | | |
| | pM1b | 100% | | |
| II | Overall* | 73% | 0% | 65% |
| | pM1a | 25% | | |
| | pM1b | 90% | | |

*Includes patients with pM1a, pM1b and non-determined metastasis status

Example 10

Clinical Study

Figure 9:
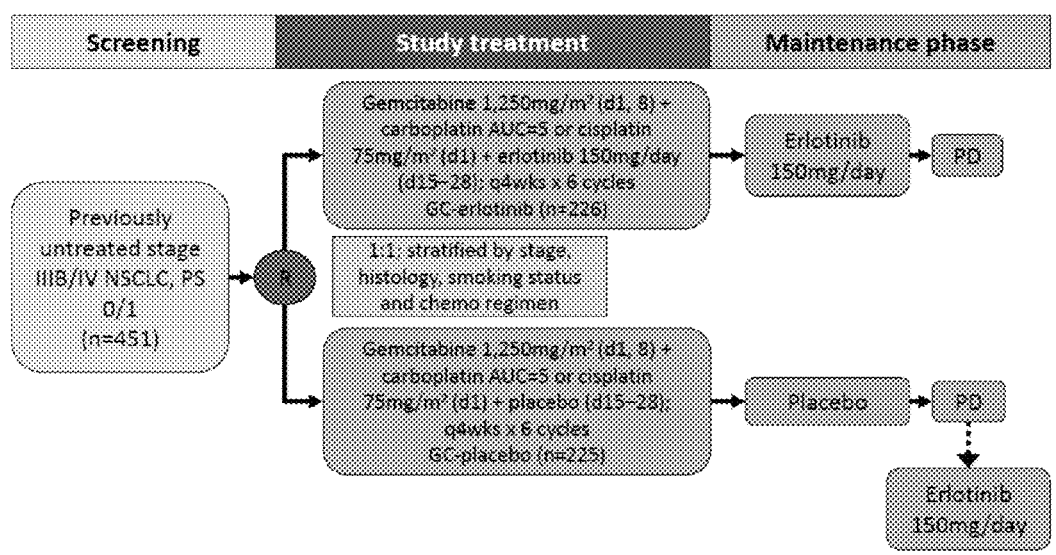
FIG. 9 is a schematic representation of the design of the clinical study related to the investigation of treatment outcomes of NSCLC patients.

A clinical study was conducted for evaluating treatment outcomes in NSCLC patient. The study design is schematically illustrated in FIG. 9. 451 patients with previously untreated stage IIIB/IV NSCLC were enrolled in the study. The patients were divided into two approximately even groups, stratified by cancer stage, histology, smoking status and assigned a treatment regiment. Three treatment regiments were used, as discussed in more detail below: gemcitabine+carboplatin, cisplatin+erlotinib, or cisplatin+placebo. The two patient groups were assigned to two different arms of the study: a combination therapy arm, meaning a combination of chemotherapy and TKI therapy, and chemotherapy arm. At the four-week treatment stage, the patients enrolled in the combination therapy arm ("CE arm") were administered 1,250 mg/m$^2$ gemcitabine on days 1 and 8 of each treatment cycle, plus 75 mg/m$^2$ carboplatin AUC=5 or cisplatin on day 1, plus 150 mg/day of erlotinib (Tarceva®) on days 15-28. The patients of the chemotherapy arm ("C arm") were administered 1,250 mg/m$^2$ gemcitabine on days 1 and 8 of each treatment cycle, plus 75 mg/m$^2$ carboplatin AUC=5 or cisplatin on day 1, plus placebo on days 15-28. The above therapies were repeated for 6 treatment cycles for each of the groups ("treatment phase"). At the maintenance phase, the patients enrolled in the combination therapy arm were administered 150 mg/day of erlotinib until the appearance of progressive disease. The patients of the chemotherapy arm were administered placebo until the appearance of progressive disease, at which point the administration of erlotinib at 150 mg/day was started. Progressive disease (PD) was defined according to RECIST.

Figure 10:
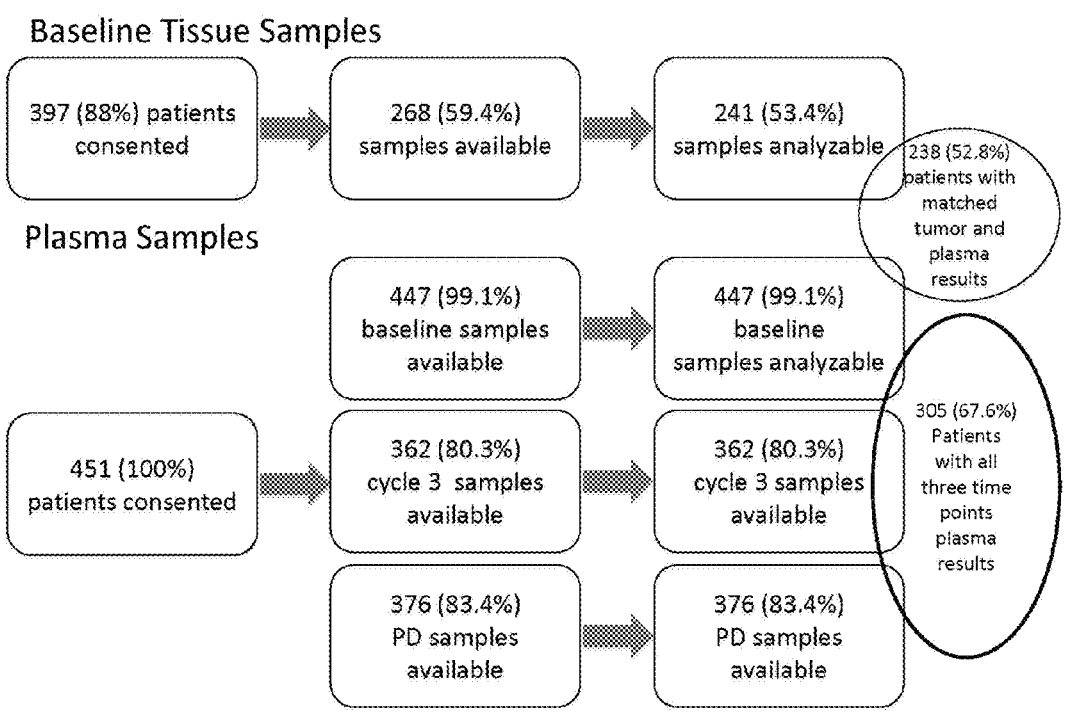
FIG. 10 is a schematic representation of the summary of the samples obtained during the course of the clinical study illustrated in FIG. 9.

Baseline tissue and plasma samples were collected from a number of the study participants at the beginning of the study ("baseline") prior to therapy administration. Plasma samples were also collected from a number of patients at the end of treatment cycle 3 ("C3") and at the progressive disease stage ("PD"). The quantities and types of the samples that became available during the study are summarized in FIG. 10. Analyzable samples at baseline, C3 and PD were available for 305 of the 451 patients who consented to the collection and analysis of their plasma samples (67.6%).

Detection of mutant target DNA in plasma samples were conducted by qPCR generally according to the procedures described in Examples 1-4. Tissue samples were formalin-fixed paraffin-embedded tissue (FFPET) samples prepared and stored according to conventional procedures. Blood samples were plasma samples prepared and stored according to conventional procedures. One FFPET section was used for each tissue test, and one 2 ml plasma sample was used for each blood test. Nucleic acid isolation from the tissue and blood samples and testing was conducted essentially as described in Examples 1-4. The testing was conducted using COBAS® EGFR Mutation Test Kits adapted for FFPET and blood testing, respectively.

Example 11

EGFR Mutation Incidence

Incidence of plasma EGFR mutation-positive tissue and plasma samples was determined. For plasma samples, the overall incidence of mutation-positive samples was 35% (106/305) at baseline, 15% (47/305) at C3 and 27% (81/305) at PD sample collection points, also referred to as "time points." Detailed distribution of detected EGFR mutated sequences among the patients is shown in Table 8. For TKI sensitizing mutations, the incidence was 40.2% for tissue samples, 32.2% for baseline plasma samples, 13.0% for C3 plasma samples, and 23.9% for PD plasma samples. For TKI resistant mutations, the incidence was 5.4% for tissue samples, 2.0% for baseline plasma samples, 1.4% for C3 plasma samples, and 3.7% for PD plasma samples.

TABLE 8

EGFR mutation distribution (number of samples)

| Mutation | Baseline - tissue samples | Plasma samples | | |
|---|---|---|---|---|
| | | Baseline | C3 | PD |
| Ex19Del | 56 | 92 | 33 | 54 |
| Ex19Del + G719X | 0 | 1 | 0 | 0 |
| Ex19Del + L858R | 1 | 0 | 1 | 0 |
| Ex19Del + L858R + T790M | 0 | 0 | 0 | 1 |
| Ex19Del + T790M | 0 | 0 | 0 | 4 |
| L858R | 33 | 43 | 11 | 25 |
| L858R + T790M | 2 | 1 | 1 | 2 |
| L858R + S768I | 1 | 0 | 0 | 0 |
| L858R + Ex20Ins | 1 | 1 | 0 | 0 |
| L858R + T790M + Ex20Ins | 0 | 1 | 0 | 0 |
| L861Q | 1 | 2 | 0 | 2 |
| G719X | 1 | 2 | 1 | 1 |
| G719X + S768I | 1 | 1 | 0 | 1 |
| T790M | 1 | 0 | 0 | 0 |
| S768I | 1 | 0 | 1 | 2 |
| Ex20Ins | 6 | 5 | 3 | 4 |
| Mutations not detected | 136 | 298 | 311 | 280 |
| Total number of samples | 241 | 447 | 362 | 376 |

Example 12

Concordance Between Tumor and Plasma Samples

For 238 patients enrolled in the clinical study, EGFR analysis results were available for both tumor and baseline plasma samples ("matched pairs"). The concordance measures for detection of EGFR TKI sensitizing mutations between tumor and baseline plasma samples were as follows: sensitivity—75% (72/96 patients); specificity—96% (137/142 patients); positive predictive value—94% (72/77 patients); negative predictive value—85% (137/161 patients); overall concordance—88% (209/238 patients). The concordance data for TKI sensitizing mutations are summarized in Table 9.

TABLE 9

Concordance data for TKI-sensitizing mutations for tumor and plasma samples

| Patient mutation status | Plasma MUT+ patients - TKI sensitizing mutations (pMUT+) | Plasma MUT- patients TKI sensitizing mutations (pMUT-) | No. of matched pairs available |
|---|---|---|---|
| Tissue mutation-positive patients - TKI sensitizing mutations (tMUT+) | 72 | 24 | 96 |
| Tissue mutation-negative patients - TKI sensitizing mutations (tMUT-) | 5 | 137 | 142 |
| Total | 77 | 161 | 238 |

Example 13

Concordance Between Tumor and Plasma Samples in Patients with Different Metastasis Status It was determined that the concordance between tumor and plasma samples for TKI-sensitizing mutations was higher in the patients with distant metastasis, in comparison with the patients with no distant metastasis. Metastasis status was available for 233 patients with available tissue and baseline plasma samples. The metastasis status was determined at the baseline time point. Table 10 (A-C) shows the summary of the concordance data for the tissue and baseline plasma samples based on the metastasis status. Sensitivity of plasma EGFR mutation determination in M1b patient subgroup was 91% (41/45 patients), specificity was 98% (47/48 patients), and overall concordance was 95% (88/93 patients). In M1a patient subgroup, sensitivity of plasma EGFR mutation determination was 60% (29/48 patients), specificity was 95% (83/87 patients) and overall concordance was 83% (112/135 patients).

TABLE 10

Concordance data between tumor and plasma samples and metastasis status for TKI-sensitizing mutations A. Summary of the data based on patient metastasis status

| Patient metastasis status | No. of matched pairs available | tMUT+ |
|---|---|---|
| Advanced NSCLC with no distant metastasis: stage III and stage IV M1a | 135 | 36% (48/135) |
| Advanced NSCLC with any distant metastasis: stage IV M1b | 98 | 48% (47/98) |

| Patient mutation status | pMUT+ patients | pMUT- patients |
|---|---|---|

B. Concordance between tumor and tissue samples in patients with M1a metastasis status

| tMUT+ patients | 29 | 19 |
| tMUT- patients | 4 | 83 |

C. Concordance between tumor and tissue samples in patients with M1a metastasis status

| tMUT+ patients | 43 | 4 |
| tMUT- patients | 1 | 50 |

Example 14

Detection of Target DNA in Plasma Samples

Figure 11:
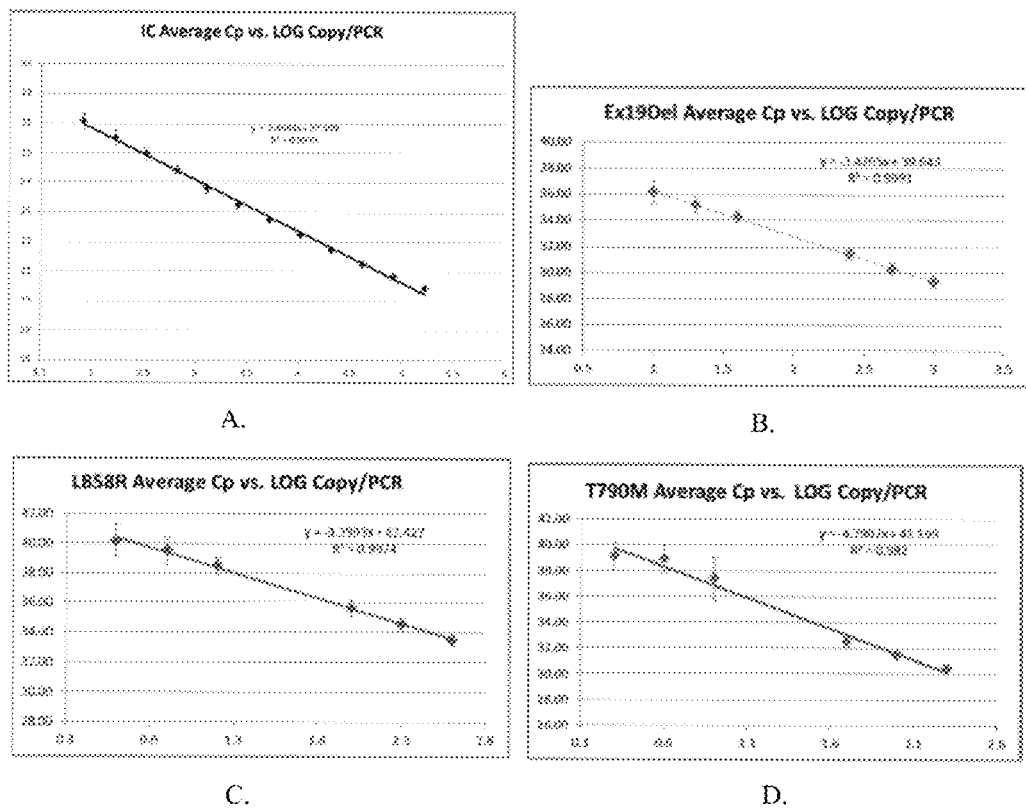
FIG. 11 are the plots representing the calibration curves used for quantification of target nucleic acids in the PCR samples: panel A—internal control target; panel B—Ex19Del target; panel C—L858R target; panel D—T7890M target.
Figure 12:
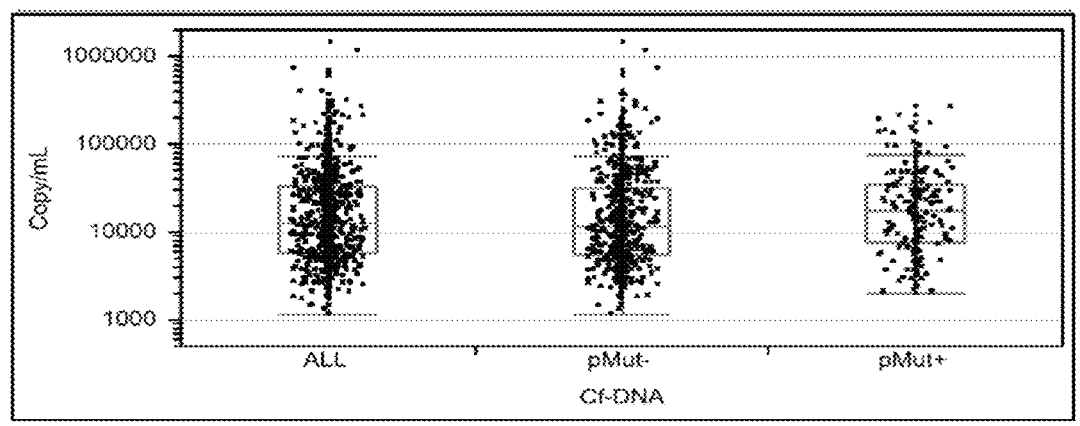
FIG. 12 is a dot plot of all the data points obtained at baseline, C3 and PD time points, which illustrates the data on the distribution of cell free (Cf) DNA in the plasma samples tested for TKI-sensitive mutations; amounts of DNA detected in the samples (copy per ml of plasma) are plotted on the Y-axis; plotted separately on the X axis are all the samples grouped together ("ALL"), mutation-negative samples ("pMut−") and mutation-positive samples ("pMut+").

The standard curves used for quantification of DNA targets are shown in FIG. 11. Distribution of cell free (cf) DNA in EGFR plasma mutation-positive and plasma mutation-negative patients is illustrated by FIG. 12 and Table 11. The experimental results discussed in this example show that the detection was linear in the detection range. It is to be understood that Cp can be used instead of DNA copy number in the standard curves for quantification of DNA targets.

TABLE 11

Distribution of total cell-free DNA (copy/ml) detected by COBAS® in patients (the data set is shown in FIG. 12)

| Patient mutation status | Detected amount of cf DNA (copy/ml) | | |
|---|---|---|---|
| | Minimum | Median | Maximum |
| pMUT− (n = 904) | 1130 | 11518 | 1438351 |
| pMUT+ (n = 281) | 2025 | 17192 | 265835 |

Figure 13:
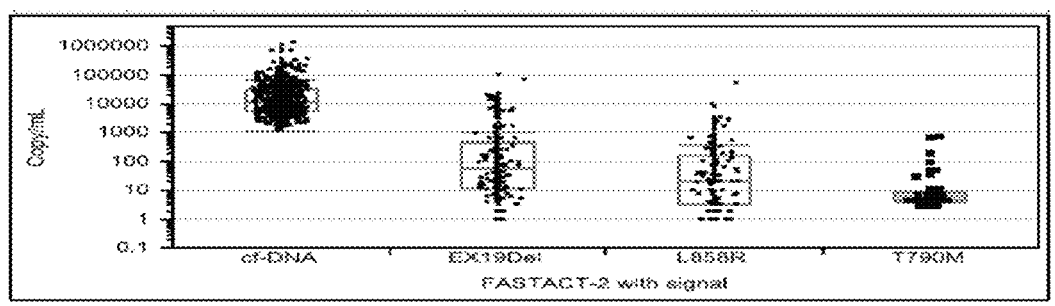
FIG. 13 is a dot plot of all the data points obtained at baseline, C3 and PD time points, which illustrates the data on the distribution of cf DNA and mutated EGFR DNA sequences in the samples tested for TKI-sensitive mutations; amounts of DNA detected in the samples (copy per ml of plasma) are plotted on the Y-axis; plotted separately on the X-axis are the data for cf DNA (cf-DNA); Ex19Del deletion and L858R and T790M substitutions.

The data on the levels of DNA detected by COBAS® plasma samples of pMUT+ patients is illustrated in FIG. 13 and Table 12. The data illustrates the detection range for each mutant in the FASTACT-2 clinical trial population.

Figure 14:
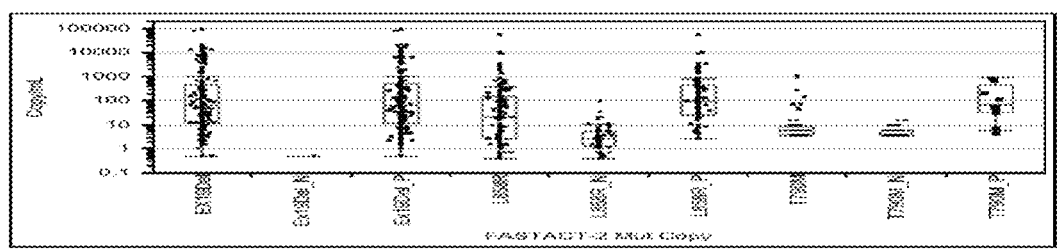
FIG. 14 is a dot plot of all the data points obtained at baseline, C3 and PD time points, which illustrates the data on the distribution of mutated EGFR DNA in the samples tested for TKI-sensitive mutations; amounts of DNA detected in the samples (copy per ml of plasma) are plotted on the Y-axis; plotted separately on the X axis are the data for Ex19Del, L858R and T790M detection results, with mutation-positive samples and mutation-negative (marked with −) samples grouped separately.
Figure 15:
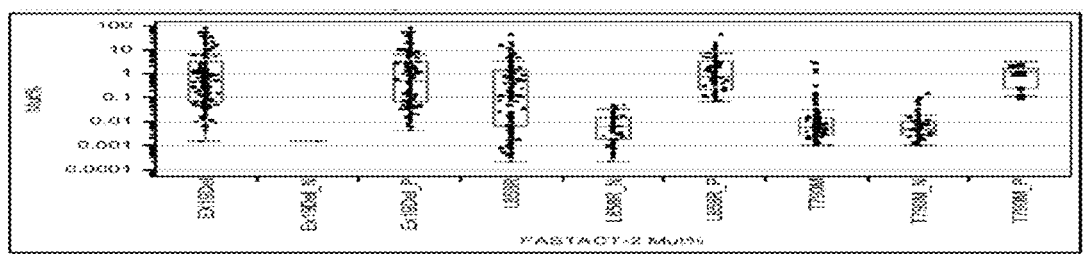
FIG. 15 is a dot plot of all the data points obtained at baseline, C3 and PD time points, which illustrates the data on the distribution of mutated EGFR DNA in the samples tested for TKI-sensitive mutations; the ratio of mutant DNA detected vs. total genomic DNA detected in the samples (Mut %) are plotted on the Y-axis; plotted separately on the X axis are the data for Ex19Del, L858R and T790M detection results, with mutation-positive samples and mutation-negative (marked with −) samples grouped separately.

The comparative data illustrating levels of mutated DNA detected by COBAS® test in the plasma of mutation-positive and mutation-negative patients is shown n FIGS. 14 and 15 and Tables 13 and 14. FIG. 14 and Table 13 represent the data as DNA levels (copy/ml), whereas FIG. 15 and Table 14 represent the data as relative amount of target DNA detected in the sample with respect to wild-type DNA (Mut %) Mut % ratio of mutant DNA detected vs. the total genomic DNA (gDNA) detected. The data shows the detection range, as expressed in Mut %, in the FASTACT-2 clinical trial population for each mutant.

TABLE 12

Detected levels of DNA (copy/ml) in the plasma samples of MUT+ patients (the corresponding data set is illlustrated in FIG. 13).

| Patient mutation status | Detected amount of cf DNA (copy/ml) | | |
|---|---|---|---|
| | Minimum | Median | Maximum |
| Total cf-DNA (n = 1185) | 1130 | 12396 | 1438351 |
| Ex19Del (n = 187) | <1 | 62 | 92998 |
| L858R (n = 146) | <1 | 61 | 54495 |
| T790M (N = 92) | 4 | 6 | 1069 |

TABLE 13

Detected levels of DNA (copy/ml) in the plasma samples of mutation-positive ("positive") and mutation-negative ("negative") patients (the corresponding data set is illustrated in FIG. 14)

| Sample status (n is the number of samples available in each subgroup) | Detected amount of mutated DNA (copy/ml) | | |
|---|---|---|---|
| | Minimum | Median | Maximum |
| Ex19Del positive (n = 186) | 0.5 | 62.1 | 52998.3 |
| Ex19Del negative (n = 1) | 0.5 | 0.5 | 0.5 |
| L858R positive (n = 86) | 2.7 | 95.5 | 54494.8 |
| L858R negative (n = 60) | 0.4 | 2.7 | 93.6 |
| T790M positive (n = 10) | 5.8 | 67.3 | 1069.1 |
| T790M negative (n = 82) | 3.5 | 5.7 | 15.0 |

TABLE 14

Detected levels of DNA (% of mutant DNA detected relative to total DNA detected) in the plasma samples of mutation-positive ("positive") and mutation-negative ("negative") patients (the corresponding data set is shown in FIG. 15).

| Sample status (n is the number of samples available in each subgroup) | Relative detected amount of mutated DNA (%) | | |
|---|---|---|---|
| | Minimum | Median | Maximum |
| Ex19Del positive (n = 186) | 0.0041 | 0.4955 | 76.1088 |
| Ex19Del negative (n = 1) | 0.0015 | 0.0015 | 0.0015 |
| L858R positive (n = 86) | 0.0679 | 0.7510 | 44.3351 |
| L858R negative (n = 60) | 0.0002 | 0.0062 | 0.0500 |
| T790M positive (n = 10) | 0.1212 | 1.1968 | 3.0433 |
| T790M negative (n = 82) | 0.0010 | 0.0048 | 0.1373 |

Example 15

Analysis of Plasma Samples at Different Time Points

Analyzable plasma samples at each of baseline, C3 and PD time points were available for 305 of 451 patients (67.6%). Incidence of plasma EGFR mutation-positive samples at baseline, C3 and PD was 35% (106/305), 15% (47/305) and 27% (81/305), respectively. 98 of 10 mutation-positive patients were shown to harbor Exon 19 deletion (Ex19Del) or L858R substitution at baseline time point (C arm—51; CE—arm 47). At C3 time point, 21 (41%) of C arm patients lost EGFR mutation positivity, and 39 (83%) of CE arm patients lost mutation-positivity. At PD time point, 8 of the 21 patients in C arm and 18 of the 39 patients in CE arm regained mutation-positivity. These data showed that patient mutation load was changing during treatment.

Figure 16:
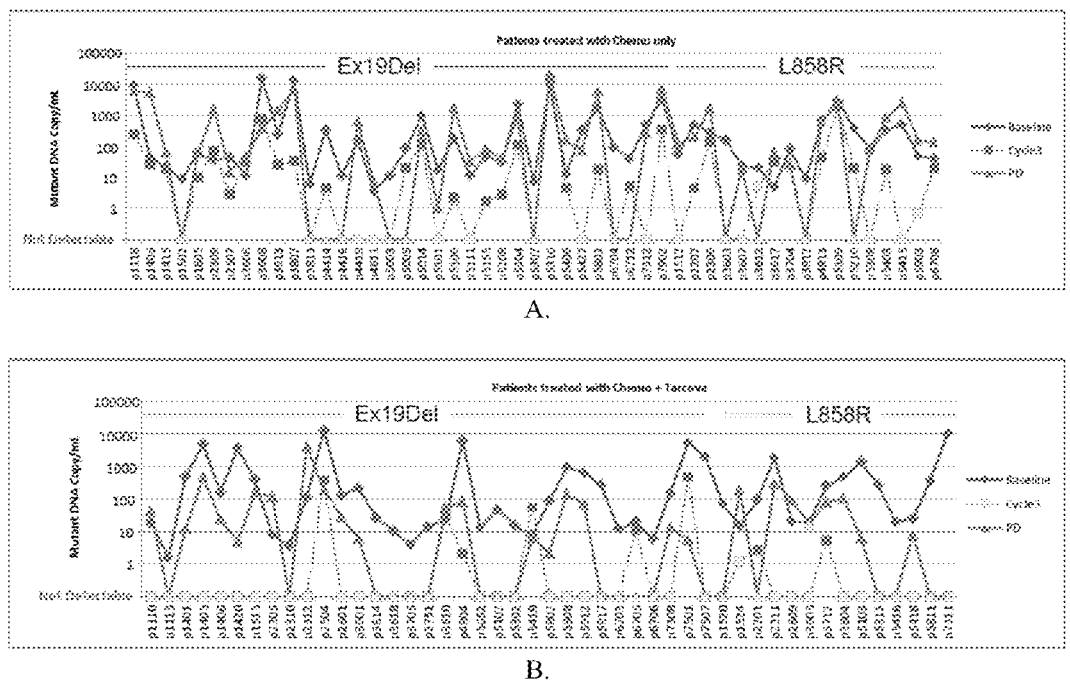
FIG. 16 is a plot illustrating the data on the amounts of mutated DNA (copy/ml) detected for Ex19Del and L858R mutations in the samples obtained at three different time points—baseline (diamonds), C3 ("Cycle3"—squares) and PD (triangles) and plotted for individual patients (patient ID numbers are shown on the X axis); the data are grouped into two panels for the patients treated with chemotherapy only ("Chemo only"—panel A) and the combination of chemotherapy and TKI therapy ("Chemo+Tarceva"—panel B); amounts of mutated DNA detected in each sample (copy/ml) are plotted on Y axis.
Figure 17:
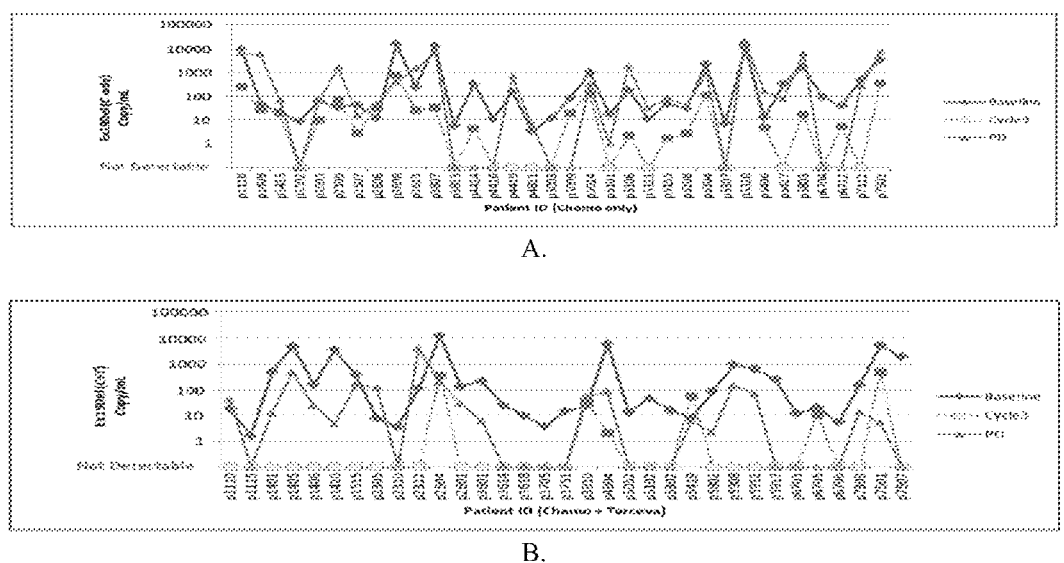
FIG. 17 is a plot illustrating the data on the amounts of mutated DNA (copy/ml) detected for Ex19Del mutation in the samples obtained at three different time points—baseline (diamonds), C3 ("Cycle3"—squares) and PD (triangles) and plotted for individual patients (patient ID numbers are shown on the X axis); the data are grouped into two panels for the patients treated with chemotherapy only ("Chemo only"—panel A) and the combination of chemotherapy and TKI therapy ("Chemo+Tarceva"—panel B); amounts of mutated DNA detected in each sample (copy/ml) are plotted on Y axis.
Figure 18:
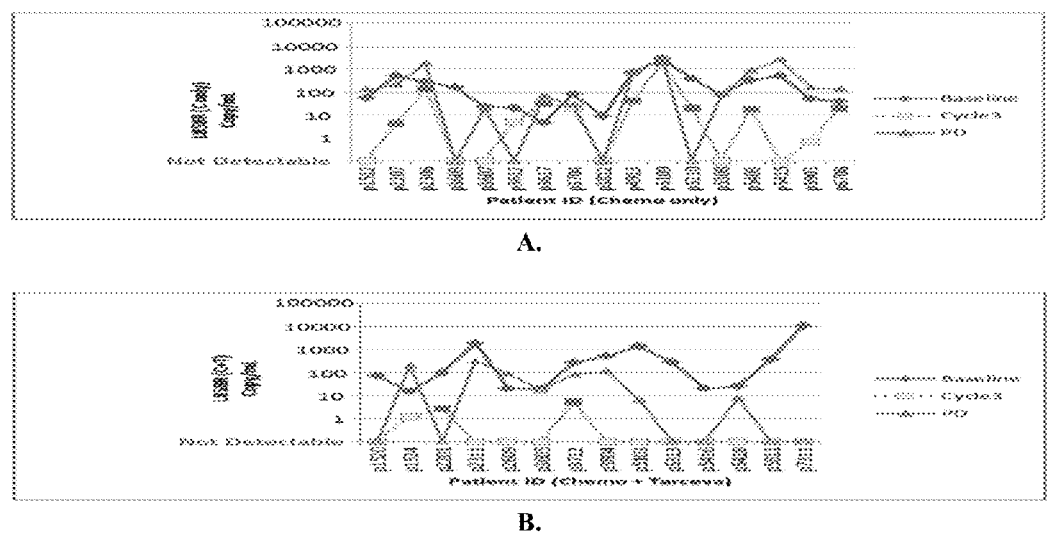
FIG. 18 is a plot illustrating the data on the amounts of mutated DNA (copy/ml) for L858R mutation detected in the samples obtained at three different time points—baseline (diamonds), C3 ("Cycle3"—squares) and PD (triangles) and plotted for individual patients (patient ID numbers are shown on the X axis); the data are grouped into two panels for the patients treated with chemotherapy only ("Chemo only"—panel A) and the combination of chemotherapy and TKI therapy ("Chemo+Tarceva"—panel B); amounts of mutated DNA detected in each sample (copy/ml) are plotted on Y axis.

199 patients were mutation-negative at baseline (103 patients in C arm and 96 patients in CE arm). Out of these patients, 12 patients became mutation-positive at PD time point based on plasma results. For the 6 out of these 12 patients, tissue results were available and indicated that all 6 patient harbored the same mutation or mutations in the tissue sample as those detected in the plasma sample collected at PD time point. These data showed that patient mutation load was dynamic during the treatment and disease progression. The results of the data analysis are illustrated by FIGS. 16-18 and Tables 15-20.

TABLE 15

Summary of the data on the incidence of different mutations in plasma samples at three time points

| Mutation(s) detected | Baseline | C3 | PD |
|---|---|---|---|
| Ex19Del | 66 | 31 | 46 |
| Ex19Del + G719X | 1 | 0 | 0 |
| Ex19Del + L858R | 0 | 1 | 0 |
| Ex19Del + L858R + T790M | 0 | 0 | 1 |
| Ex19Del + T790M | 0 | 0 | 3 |
| L858R | 30 | 10 | 22 |
| L858R + T790M | 1 | 0 | 2 |
| L861Q | 1 | 0 | 1 |
| G719X | 2 | 1 | 1 |
| S768I | 0 | 1 | 2 |
| Ex20Ins | 5 | 3 | 3 |
| MND | 199 | 258 | 224 |
| Total | 305 | 305 | 305 |

TABLE 16

Summary of the data on the incidence of plasma mutation-positive and mutation-negative patients at the three time points

| Study arm | Baseline MUT+/MUT− | C3 MUT+/MUT− | PD MUT+/MUT− |
|---|---|---|---|
| C | 0 (0%)/103 (100%) | 4 (4%)/99 (96%) | 9 (9%)/94 (91%) |
| CE | 0 (0%)/96 (100%) | 0 (0%)/96 (100%) | 3 (3%)/93 (97%) |

TABLE 17

Summary of the data on the mutations detected in six of the patients who were detected to be mutation-positive at PD stage

| Patient | Mutations detected in the tissue sample | Mutations detected in the plasma samples Baseline | C3 | PD |
|---|---|---|---|---|
| 1 | L858R | MUT− | MUT− | L858R |
| 2 | G719X & S768I | MUT− | MUT− | S768I |
| 3 | L858R | MUT− | MUT− | L858R |
| 4 | Ex19 Del | MUT− | MUT− | Ex19Del |
| 5 | S768I | MUT− | MUT− | S768I |
| 6 | L858R | MUT− | MUT− | L858R |

TABLE 18

Summary of the data on the patients who were plasma Ex19Del and/or L858R positive at baseline time point

| Study arm | Baseline MUT+/MUT− for Ex19Del and/or L858R | C3 MUT+/MUT− for Ex19Del and/or L858R | PD MUT+/MUT− for Ex19Del and/or L858R |
|---|---|---|---|
| C | 51 (100%)/0 (0%) | 30 (59%)/21 (41%) | 38 (75%)/13 (25%) |
| CE | 47 (100%)/0 (0%) | 8 (17%)/39 (83%) | 26 (55%)/21 (45%) |

TABLE 19

Summary of the data on the patients who were Ex19Del positive at baseline

| Study arm | Baseline MUT+/MUT− for Ex19Del and/or L858R | C3 MUT+/MUT− for Ex19Del and/or L858R | PD MUT+/MUT− for Ex19Del and/or L858R |
|---|---|---|---|
| C | 34 (100%)/0 (0%) | 22 (65%)/12 (35%) | 25 (74%)/9 (26%) |
| C + E | 33 (100%)/0 (0%) | 6 (18%)/27 (82%) | 19 (58%)/14 (42%) |

TABLE 20

Summary of the data on the patients who were L858R positive at baseline (four samples at C3 and one sample at PD time points were estimated to be L858R positive but were not included in the summary due to high background of cf DNA present in these samples).

| Study arm | Base-line MUT+/MUT− for L858R | C3 MUT+/MUT− for L858R | PD MUT+/MUT− for L858R |
|---|---|---|---|
| C | 17 (100%)/0 (0%) | 8 (47%)/9 (53%) | 13 (76%)/4 (24%) |
| CE | 14 (100%)/0 (0%) | 2 (14%)/12 (86%) | 7 (50%)/7 (50%) |

Example 16

Figure 19:
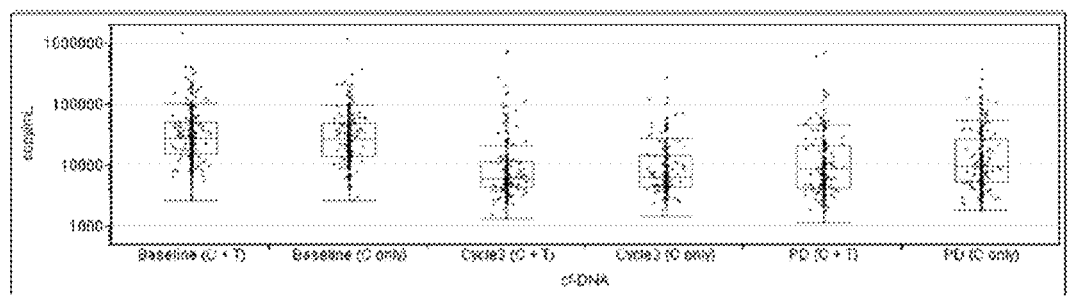
FIG. 19 is a dot plot illustrating the data on total cell free (cf) DNA obtained at three different time points ("baseline," C3 and PD—the explanation is provided further in the text) during the clinical study; the amounts of detected DNA (copy/ml) are plotted on Y axis and grouped on the X axis for the different time points and for the patients enrolled in the two arms of the clinical study (chemotherapy only therapy arm—"C only"; combination of chemotherapy and TKI therapy—"C+T arm").
Figure 20:
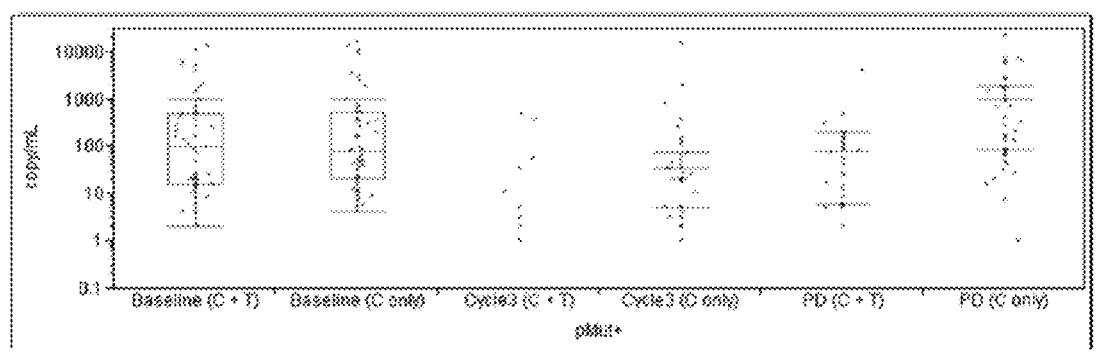
FIG. 20 is a dot plot illustrating the data on the mutated DNA obtained at three different time points ("baseline," C3 and PD—the explanation is provided further in the text) during the clinical study; DNA amounts detected (copy/ml) are plotted on the X axis and grouped on the Y axis for the three time points and for the patients enrolled in the two arms of the clinical study (chemotherapy only therapy arm—"C only"; combination of chemotherapy and TKI therapy—"C+T arm").
Figure 21:
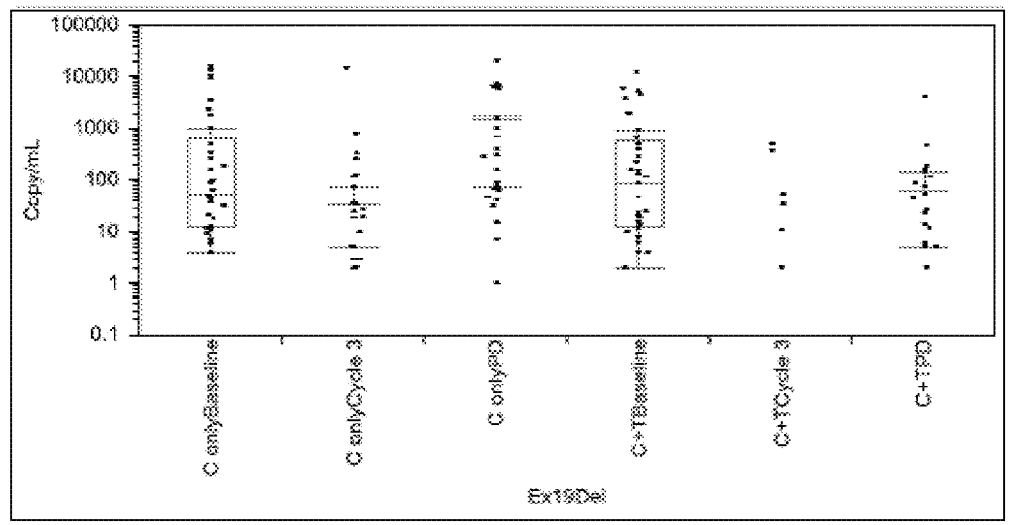
FIG. 21 is a dot plot illustrating the data on the mutated DNA for Ex19Del mutation (panel A) and L858R mutation (panel B) obtained at three different time points ("baseline," C3 and PD—the explanation is provided further in the text) during the clinical study; the data for DNA amounts detected (copy/ml) is plotted on Y axis and is grouped on X axis for the patients enrolled in the two arms of the clinical study (chemotherapy only therapy arm—"C only"; combination of chemotherapy and TKI therapy—"C+T").
Figure 21:
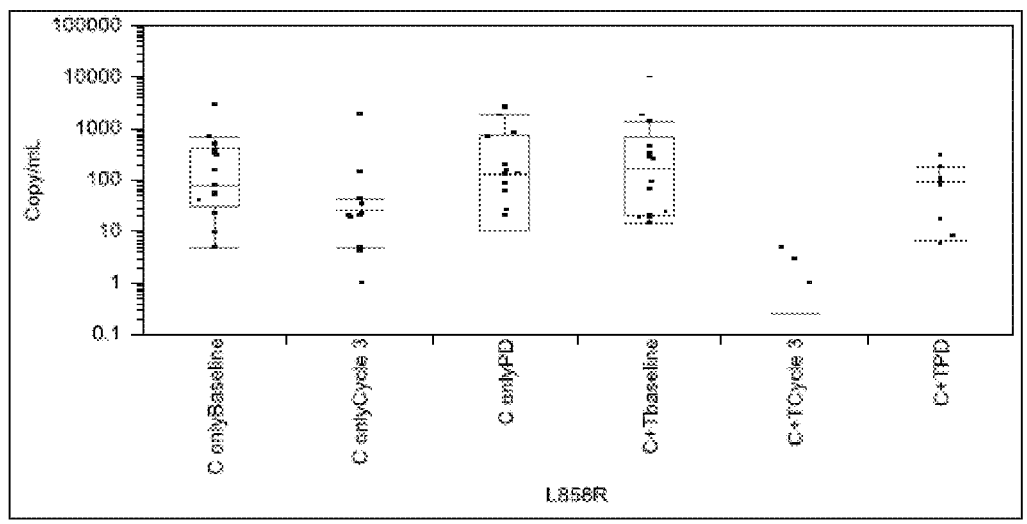

Dynamic Quantitative Changes of DNA Levels Detected in Plasma Samples Over the Course of the Clinical Study Dynamic quantitative changes of DNA levels detected in plasma samples over the course of the study were evaluated. FIG. 19 and Table 21 illustrate dynamic quantitative change in total plasma cf DNA over the course of the study. FIG. 20 and Table 22 illustrate dynamic quantitative change in total levels of mutated target DNA over the course of the study. FIG. 21 and Table 23 illustrate dynamic quantitative change in target mutated DNA in EGFR exons 19 and 21 over the course of the study. Over the course of the study, a considerable decline in the total levels of plasma EGFR target sequences was observed in both C and CE arms of the clinical study. However, detected levels of EGFR-mutated DNA in plasma rebounded to high level at PD in C arm only and remained low in CE arm. The data discussed in this example showed that patient mutation load was dynamic during treatment. It also showed that TKI was more effective at treating the patients with EGFR-positive tumors.

TABLE 21

Levels of total plasma cf DNA detected at three time points during the clinical study

| | Median cf DNA (copy/mL) | | |
|---|---|---|---|
| Study arm | Baseline | C3 | PD |
| CE | 27550 | 5975 | 8554 |
| C | 26225 | 6389 | 9528 |

TABLE 22

Levels of total EGFR-mutated DNA detected at three time points

| Study arm (n = number of patients with analyzable samples at | Median EGFR-mutated DNA (copy/mL) | | |
|---|---|---|---|
| | Baseline | C3 | PD |
| CE (n = 47) | 94 | 0 | 6 |
| C (n = 51) | 78 | 5 | 83 |

TABLE 23

Levels of total EGFR mutated DNA in Exons 19 and 21 detected at three time points

| Study arm and mutation locus | Median EGFR-mutated DNA (copy/mL) | | |
|---|---|---|---|
| | Baseline | C3 | PD |
| C (Exon 19) | 55.5 | 5.0 | 71.5 |
| CE (Exon 19) | 86.0 | 0.0 | 5.0 |
| C (Exon 21) | 82.0 | 5.0 | 128.0 |
| CE (Exon 21) | 174.5 | 0.0 | 7.0 |

Example 17

Correlation Between Mutation Status and Treatment Outcomes

Analysis of the data was conducted in order to detect correlations between detection of EGFR mutations in plasma and tissue samples of a NSCLC patients with the treatment outcomes. The subgroup analysis was performed on overall response rate (ORR), progression free survival (PFS) and overall survival (OS) of 138 plasma mutation-positive patients (based on baseline samples) and 289 plasma mutation-negative patients, as well as tissue-positive and tissue-negative patients. Median PFS of plasma mutation-positive patients was 13.8 in CE arm of the study, vs 5.9 months in C arm (hazard ratio (HR)>0.21), compared with 16.8 for the CE arm vs 6.9 months in the C arm (HR 0.25) in tissue mutation-positive patients. Median PFS of plasma mutation-negative patients was 6.7 in the CE arm vs 6.0 months C arm of the study (HR 0.80), compared with 6.7 months in the CE arm vs 5.9 months in the C arm (HR 0.97) in tissue mutation-negative patients. Median OS of plasma mutation-positive patients was 32.4 in the CE arm vs 18.6 months in the C arm (HR 0.50), compared with 31.4 CE arm vs 20.6 months in the C arm (HR 0.48) in tissue mutation-positive patients. Median OS of plasma mutation-negative patients was 16.1 in the CE arm vs 13.3 in the C arm months (HR 0.90), compared with 14.9 in the CE arm vs 12.2 in the C arm months (HR 0.77) in tissue mutation-negative patients.

Figure 22:
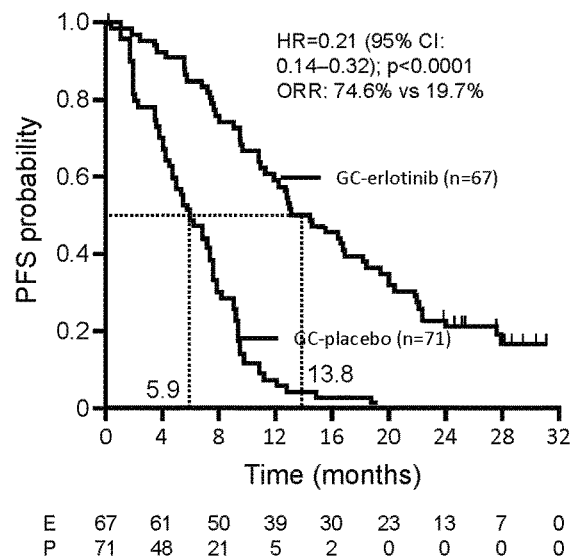
FIG. 22 shows the line plots illustrating comparative probability of progression free survival (PFS) of the patients classified as mutation-positive based on the baseline plasma samples (panel A) and tissue samples (panel B). The plots are shown are for the patients enrolled in the two arms of the clinical study (chemotherapy only arm—"GC-placebo"; combination chemotherapy+TKI therapy arm—"GC-erlotinib").
Figure 22:
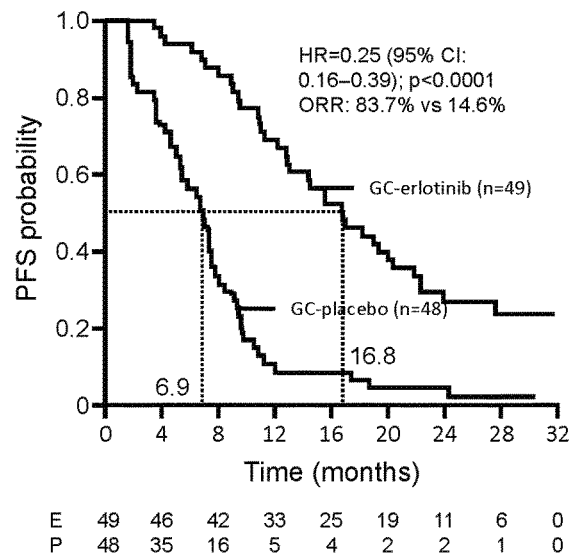
Figure 23:
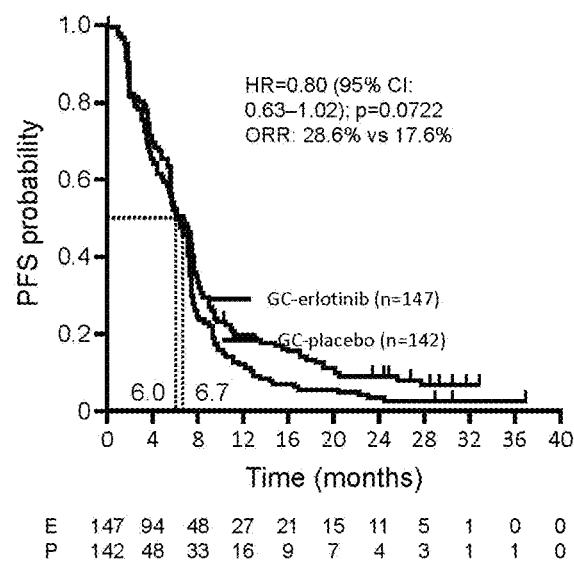
FIG. 23 shows the line plots illustrating comparative probability of progression free survival (PFS) of the patients classified as mutation-negative based on the baseline plasma samples (panel A) and tissue samples (panel B). The plots shown are for the patients the two arms of the clinical study (chemotherapy only arm—"GC-placebo"; combination chemotherapy+TKI therapy arm—"GC-erlotinib").
Figure 23:
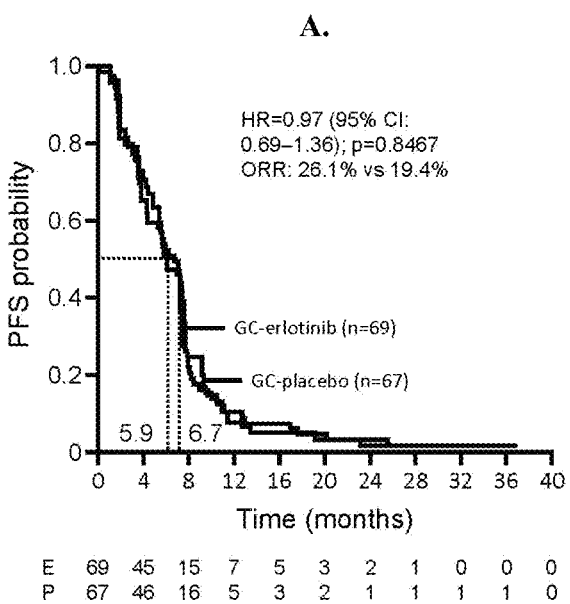
Figure 24:
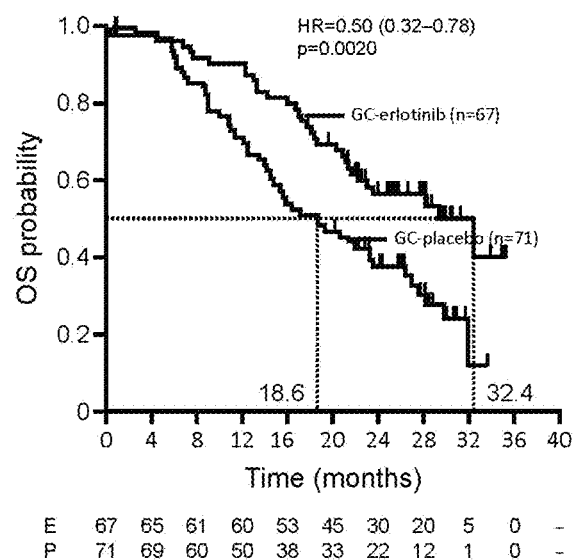
FIG. 24 shows the line plots illustrating comparative probability of overall survival (OS) of the patients classified as mutation-positive based on the baseline plasma samples (panel A) and tissue samples (panel B). The plots shown are for the patients enrolled in the two arms of the study (chemotherapy only arm—"GC-placebo"; combination chemotherapy+TKI therapy arm—"GC-erlotinib").
Figure 24:
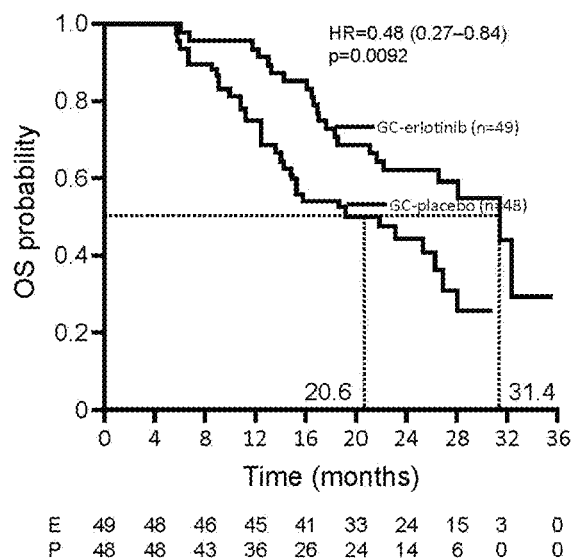
Figure 25:
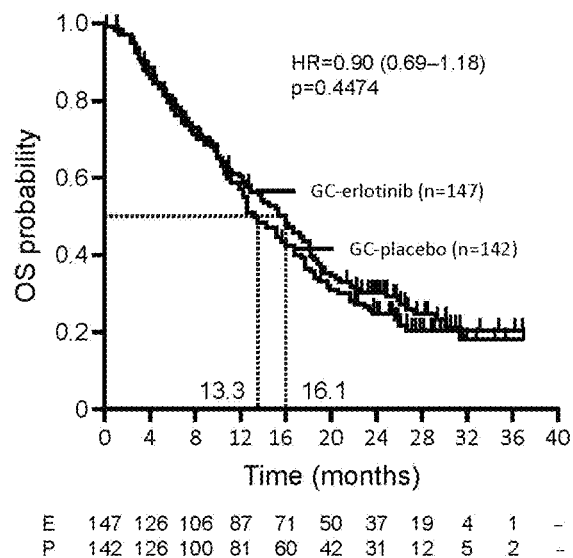
FIG. 25 shows the line plots illustrating comparative probability of overall survival (OS) of the patients classified as mutation-negative based on the baseline plasma samples (panel A) and tissue samples (panel B). The plots shown are for the patients enrolled the two arms of the clinical study (chemotherapy only arm—"GC-placebo"; combination chemotherapy+TKI therapy arm—"GC-erlotinib").
Figure 25:
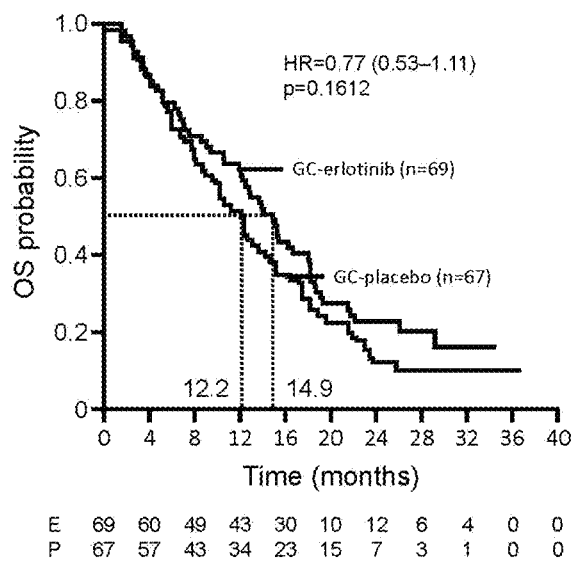
Figure 26:
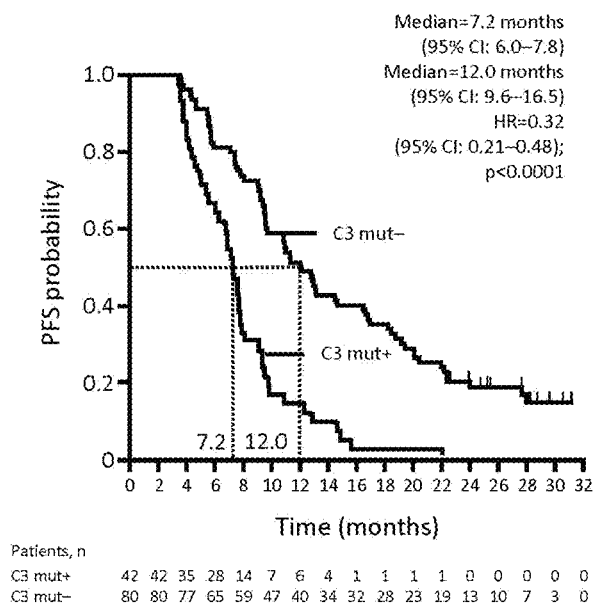
FIG. 26 shows the line plots showing illustrating comparative probability of progression free survival (panel A) and overall survival (panel B) of the patients classified as mutation-positive (C3 mut+) and mutation negative (C3 mut−) based on the plasma samples taken at C3 time point.
Figure 26:
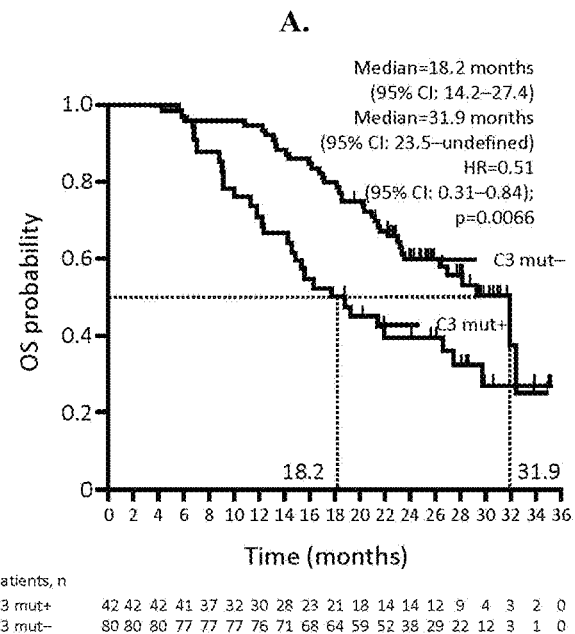
Figure 27:
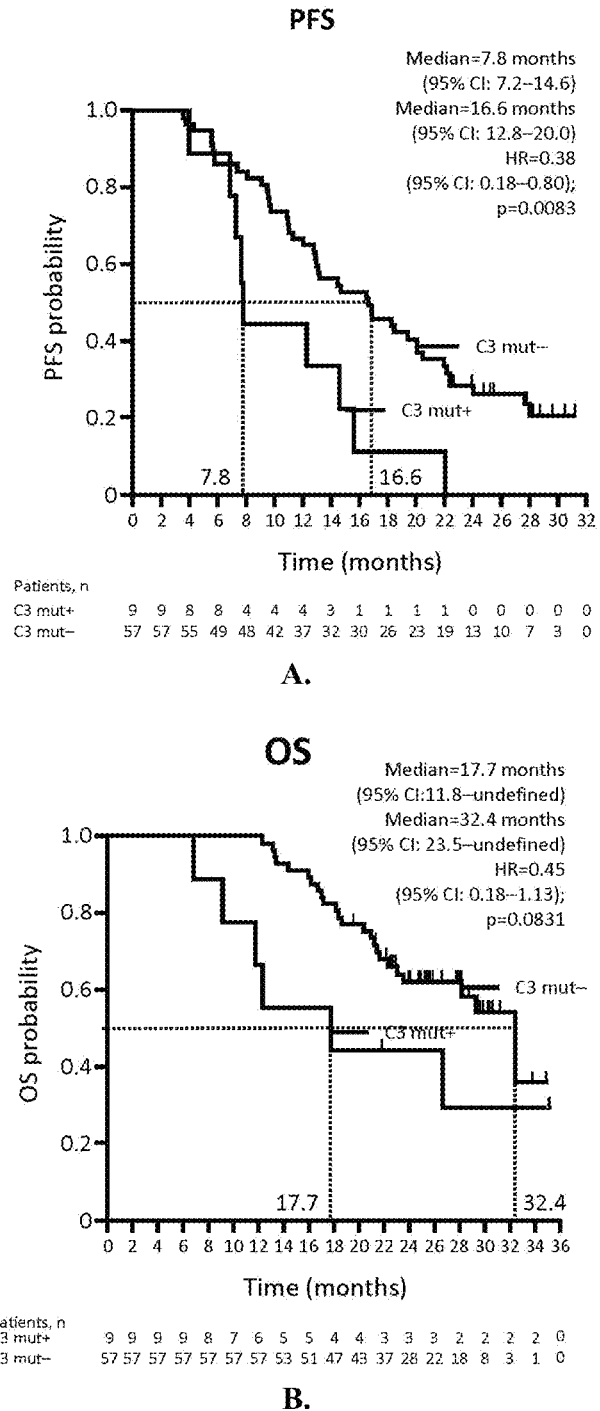
FIG. 27 shows the line plots illustrating comparative probability of progression free survival (panel A) and overall survival (panel B) of the patients classified as mutation-positive (C3 mut+) and mutation negative (C3 mut−) based on the plasma samples taken at C3 time point in the combination chemotherapy+TKI therapy arm.

Treatment outcomes according to baseline plasma EGFR mutation status are summarized in Table 24 and FIGS. 22-25. Comparative data on the treatment outcomes based on C3 plasma samples and tissue samples is illustrated in FIGS. 26-27 and Tables 25 and 26. The above analyses of the treatment outcomes in patients with different mutation status revealed that plasma EGFR mutation status can be predictive of the treatment outcome, such as the length of progression free survival and/or overall survival of a particular patient. FIGS. 22A (PFS) and 24A (OS) illustrate the comparison between plasma mutation-positive patients (at baseline) in two treatment arms (138 patients total). The comparison indicated that a combination of chemotherapy and erlotinib therapy was a better treatment option for the patients determined to be plasma mutation-positive at baseline time point. FIGS. 22B (PFS) and 24B (OS) illustrate the comparison between tissue EGFR mutation positive patients (tested at baseline) in two treatment arms (97 patients total). The comparison indicated that a combination of chemotherapy and erolotinib was a better treatment option for tissue EGFR mutation positive patients. FIGS. 22 and 24 show that detection of mutation load in plasma or tissue at baseline predicted similar outcomes for mutation-positive patients. FIGS. 23 and 25 illustrate the comparison between mutation-negative patients at baseline (plasma mutation negative—FIGS. 23A and 25A; tissue mutation negative—FIGS. 23B and 25B) in two treatment arms. The detection of mutation load in plasma or tissue at baseline predicted similar outcomes for mutation-negative patients. FIG. 26 illustrates the analysis of the patients who were tested plasma EGFR mutation positive at baseline and also were tested again at C3 time point (total 122 patients). These 122 patients were grouped based on their C3 EGFR mutation status (positive or negative) and treatment arm. If the patients were plasma mutation negative at C3 time point (which possibly indicated that the patients responded to the treatment), they had better PFS and OS in both treatment groups. Positive mutation status at baseline followed by negative mutation status at C3 time point was associated with improved outcomes; patients positive at baseline and still positive at C3 time point experienced worse outcomes FIG. 27 illustrates the analysis of the patients in chemotherapy+erlotinib treatment arm who were tested plasma EGFR mutation positive at baseline and also were tested again at C3 time point (122 patients total). These 122 patients were grouped based on their C3 EGFR mutation status (positive or negative). The best outcome with respect to PSF was observed for the patients that were mutation negative at C3 time point and administered chemotherapy+erlotinib treatment. Positive mutation status at baseline followed by negative mutation status at C3 time point was associated with improved outcomes; patients positive at baseline and still positive at C3 experienced worse outcomes It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

TABLE 24

Treatment outcomes according to plasma EGFR mutation status at baseline time point; A - summary of data for plasma mutation positive patients (138 patients); B - summary of data for plasma mutation-negative patients (289 patients)

| Study arm | ORR, % | PFS, months | OS, months |
|---|---|---|---|
| A. | | | |
| CE | 74.6 | 13.8 | 32.4 |
| C | 19.7 | 5.9 | 18.6 |
| Statistical parameters | | HR: 0.21 (95% confidence interval (CI) 0.14-0.32) | HR: 0.50 (95% CI 0.32-0.78) |
| B. | | | |
| CE | 28.6 | 6.7 | 16.1 |
| C | 17.6 | 6.0 | 13.3 |
| Statistical parameters | | HR: 0.80 (95% CI 0.63-1.02) | HR: 0.90 (95% CI 0.69-1.18) |

TABLE 25

Correlation between plasma C3 mutation status and treatment outcomes in mutation-positive and mutation negative patients (total of 122 patients)

| Treatment outcome type | ORR | PFS | OS |
|---|---|---|---|
| pMUT+ patients at C3 | 14/42 = 33.3% | Median = 7.2 months<br>95% CI = (6.0, 7.8) | Median = 18.2 months<br>95% CI = (14.2, 27.4) |
| pMUT− patients at C3 | 53/80 = 66.3% | Median = 12.0 months<br>95% CI = (9.6, 16.5) | Median = 31.9 months<br>95% CI = (23.5, undefined) |
| Statistical parameters | Odds ratio (OR): 3.93<br>95% CI: (1.78, 8.66)<br>p = 0.0007 | HR: 0.32<br>95% CI: (0.21, 0.48)<br>p < 0.0001 | HR: 0.51<br>95% CI: (0.31, 0.84)<br>p = 0.0066 |

TABLE 26

Correlation between plasma C3 mutation status and treatment outcomes in mutation-positive and mutation negative patients in the two arms of the clinical study (total of 122 patients)

| Patient subgroup | Treatment outcome type | ORR | Median PFS (months) | Median OS (months) |
|---|---|---|---|---|
| pMUT+ patients at C3 | C arm | 24.2% | 6.8 | 18.8 |
|  | CE arm | 66.7% | 7.8 | 17.7 |
|  | CE arm statistical parameters | OR: 6.25<br>95% CI: (1.26, 30.90) | HR: 0.38<br>95% CI(0.17, 0.90) | HR: 0.98<br>95% CI(0.40, 2.42) |
| pMUT− patients at C3 | C arm | 26.1% | 7.8 | 26.3 |
|  | CE arm | 82.5% | 16.6 | 32.4 |
|  | CE arm statistical parameters | OR: 13.32<br>95% CI: (4.20, 42.23) | HR: 0.23<br>95% CI (0.13, 0.41) | HR: 0.61<br>95% CI (0.31, 1.21) |

---

---

The invention claimed is:

1. A method of detecting a cancer-associated somatic mutation in a sample from a human subject with a solid tumor and administering treatment to the subject, comprising:
   (a) obtaining the sample from the subject, wherein the subject has completed one or more cycles of a first targeted drug therapy, wherein the first targeted drug therapy targets the protein encoded by the nucleic acid having the cancer-associated somatic mutation;
   (b) amplifying in a first real time PCR nucleic acids in the sample using an allele-specific primer pair specific for the cancer-associated somatic mutation and a primer pair specific for an internal control;
   (c) generating a sample PCR threshold value for the cancer-associated somatic mutation, wherein the sample PCR threshold value is the number of cycles required in the first real time PCR to reach a predetermined signal magnitude for the cancer-associated somatic mutation, and generating a first internal control threshold value, wherein the first internal control threshold value is the number of cycles required in the first real time PCR to reach a predetermined signal magnitude for the internal control;

(d) amplifying in a second real time PCR DNA that does not carry the cancer-associated somatic mutation using the allele-specific primer pair specific for the cancer-associated somatic mutation and the primer pair specific for the internal control;
(e) generating a cut-off threshold value, wherein the cut-off threshold value is a breakthrough PCR cycle threshold, wherein the cut-off threshold value is the number of cycles required in the second real time PCR to reach the predetermined signal magnitude for the cancer-associated somatic mutation, and generating a second internal control threshold value, wherein the second internal control threshold value is the number of cycles required to reach the predetermined signal magnitude for the internal control;
(f) detecting a difference between the sample PCR threshold value and the first internal control PCR threshold value that is less than the difference between the cut-off threshold value and the second internal control value, thereby detecting the cancer-associated somatic mutation in the sample; and
(g) administering a second targeted drug therapy to the subject, wherein the second targeted drug therapy targets the protein encoded by the nucleic acid having the cancer-associated somatic mutation.

2. The method of claim 1, wherein the first targeted drug therapy is a reversible tyrosine kinase inhibitor and the second targeted drug therapy is an irreversible kinase inhibitor.

3. A method of detecting a cancer-associated somatic mutation in a sample from a human subject with a solid tumor and administering treatment to the subject, comprising:
(a) obtaining the sample from the subject;
(b) amplifying in a first real time PCR nucleic acids in the sample using an allele-specific primer pair specific for the cancer-associated somatic mutation and a primer pair specific for an internal control;
(c) generating a sample PCR cycle threshold value for the cancer-associated somatic mutation, wherein the sample PCR cycle threshold value is the number of cycles required in the first real time PCR to reach a predetermined signal magnitude for the cancer-associated somatic mutation, and generating a first internal control threshold value, wherein the first internal control threshold value is the number of cycles required in the first real time PCR to reach a predetermined signal magnitude for the internal control;
(d) amplifying in a second real time PCR DNA that does not carry the cancer-associated somatic mutation using the allele-specific primer pair specific for the cancer-associated somatic mutation and the primer pair specific for the internal control;
(e) generating a cut-off threshold value, wherein the cut-off threshold value is a breakthrough PCR cycle threshold, wherein the cut-off threshold value is the number of cycles required in the second real time PCR to reach the predetermined signal magnitude for the cancer-associated somatic mutation, and generating a second internal control threshold value, wherein the second internal control threshold value is the number of cycles required to reach the predetermined signal magnitude for the internal control;
(f) detecting difference between the sample PCR threshold value and the first internal control PCR threshold value is less than the difference between the cut-off threshold value and the second internal control value, thereby detecting the cancer-associated somatic mutation in the sample;
(g) administering a first targeted drug therapy to the subject, wherein the first targeted drug therapy targets the protein encoded by the nucleic acid having the cancer-associated somatic mutation;
(h) repeating steps (a)-(f) after one or more cycles of the first targeted drug therapy;
(i1) reducing or continuing administration of the first targeted drug therapy if the sample PCR cycle threshold value of the cancer-associated somatic mutation in the sample from the subject before treatment with the first targeted drug therapy is lower than the sample PCR cycle threshold value in the sample from the subject after the one or more cycles of the first targeted drug therapy; or
(i2) administering a new treatment to the subject if the sample PCR cycle threshold value of the cancer-associated somatic mutation in the sample from the subject before treatment with the first targeted drug therapy is higher than the sample PCR cycle threshold value in the sample from the subject after the one or more cycles of the first targeted drug therapy, wherein the new treatment is surgery, chemotherapy, a second targeted drug therapy that targets the protein encoded by the nucleic acid having the cancer-associated somatic mutation, or any combination thereof.

4. The method of claim 3, wherein the first targeted drug therapy is a reversible tyrosine kinase inhibitor and the second targeted drug therapy is an irreversible kinase inhibitor.

5. The method of claim 3, wherein the first targeted drug therapy comprises administration of tyrosine kinase inhibitor selected from erlotinib or gefitinib.

6. The method of claim 3, wherein the sample is a plasma sample.

7. The method of claim 3, wherein the method further comprises performing a diagnostic procedure on the subject.

8. The method of claim 7, wherein the diagnostic procedure is a radiological evaluation.

9. The method of claim 3, wherein the solid tumor is lung cancer.

10. The method of claim 3, wherein the DNA that does not carry the cancer-associated somatic mutation is genomic DNA.

11. The method of claim 1, wherein the first targeted drug therapy comprises administration of tyrosine kinase inhibitor selected from erlotinib or gefitinib.

12. The method of claim 1, wherein the sample is a plasma sample.

13. The method of claim 1, wherein the method further comprises performing a diagnostic procedure on the subject.

14. The method of claim 13, wherein the diagnostic procedure is a radiological evaluation.

15. The method of claim 1, wherein the solid tumor is lung cancer.

16. The method of claim 1, wherein the DNA that does not carry the cancer-associated somatic mutation is genomic DNA.

* * * * *